US008063202B2

(12) United States Patent
Kajihara

(10) Patent No.: US 8,063,202 B2
(45) Date of Patent: Nov. 22, 2011

(54) PROCESS FOR PREPARING GLYCOPEPTIDES HAVING ASPARAGINE-LINKED OLIGOSACCHARIDES, AND THE GLYCOPEPTIDES

(75) Inventor: Yasuhiro Kajihara, Yokohama (JP)

(73) Assignees: Otsuka Chemical Co., Ltd., Osaka (JP); Yasuhiro Kajihara, Osaka (JP)

( * ) Notice: Subject to any disclaimer, the term of this patent is extended or adjusted under 35 U.S.C. 154(b) by 100 days.

(21) Appl. No.: 12/385,711

(22) Filed: Apr. 16, 2009

(65) Prior Publication Data

US 2009/0234095 A1    Sep. 17, 2009

Related U.S. Application Data

(62) Division of application No. 10/519,983, filed as application No. PCT/JP03/08551 on Jul. 4, 2003, now Pat. No. 7,943,763.

(30) Foreign Application Priority Data

Jul. 5, 2002 (JP) ................. 2002-196821
Nov. 29, 2002 (JP) ................. 2002-349166

(51) Int. Cl.
C08B 37/00 (2006.01)
C07H 5/04 (2006.01)
C07H 5/06 (2006.01)
(52) U.S. Cl. .................................................... 536/55.3
(58) Field of Classification Search .................. None
See application file for complete search history.

(56) References Cited

U.S. PATENT DOCUMENTS 5,527,901 A    6/1996  Ratcliffe et al. .............. 536/55.3
2003/0229013 A1   12/2003  Wu et al. ........................ 514/7

FOREIGN PATENT DOCUMENTS

| EP | 0 711 766 A1 | 5/1996 |
| JP | 10-259198 A | 9/1998 |
| JP | 11-255807 | 9/1999 |
| JP | 11-255807 A | 9/1999 |
| WO | 91/09975 A1 | 7/1991 |
| WO | 94/08711 A1 | 4/1994 |
| WO | 03/008431 A1 | 1/2003 |

OTHER PUBLICATIONS

Omenn et al. Journal of the American Chemical Society 90:23, Nov. 6, 1968.*
Matsuo, Ichiro et al., "Synthesis of a Glycopeptide Carrying a N-Linked Core Pentasaccharide," *Bioorganic & Medicinal Chemistry*, vol. 3, No. 11, pp. 1455-1463.
Unverzagt, Carlo, "Chemoenzymatic synthesis of a sialylated diantennary N-glycan linked to asparagine," *Carbohydrate Research*, 305 (1998), pp. 423-431.
Leger, D. et al., "Structure Determination of the Single Glycan of Rabbit Serotransferrin by Methylation Analysis and 360MHz $^1$HNMR Spectroscopy," *FEBS Letters*, vol. 93, No. 2, 1978, pp. 255-260.

Baenziger, Jacques U., "Structure of the Oligosaccharide of Human J Chain," *The Journal of Biological Chemistry*, vol. 254, No. 10, 1979, pp. 4063-4071.
Poola, Indravathamma et al., "Internaction of asparagine-linked oligosaccharides with an immobilized rice (*Oryza saliva*) lectin column," *Biochem. J.*, 250, (1988), pp. 117-124.
Meinjohanns, Ernst et al., "Novel Sequential Solid-Phase Synthesis of N-Linked Glycopeptides From Natural Sources," *J. Chem. Soc., Perkin Trans. I*, vol. 1, 1988, pp. 549-560.
Otvos, Jr., Laszlo et al., "Automated Solid-Phase Synthesis of Glycopeptides. Incorporation of Unprotected Mono- and Disaccharide Units of N-Glycoprotein Antennae Into T Cell Epitopic Peptides," *Tetrahedron Letters*, vol. 31, No. 41, 1990, pp. 5889-5892.
Urge, Laszlo et al., "Solid-Phase Synthesis of Glycopeptides: Synthesis of Nα-Fluorenylmethoxycarbonyl L-Asparagine Nβ-Glycosides," *Tetrahedron Letters*, vol. 32, No. 29, 1991, pp. 3445-3448.
Urge, Laszlo et al., "Fmoc-protected, gycosylated asparagines potentially useful as reagents in the solid-phase synthesis of N-glycopeptides," *Carbohydrate Research*, vol. 235, 1992, pp. 83-93.
Laczkó, Ilona et al., "Synthesis and Conformational Studies of N-Glycosylated Analogues of the HIV-1 Principle Neutralizing Determinant," Biochemistry, vol. 31, No. 17, 1992, pp. 4282-4288.
Urge, Laszlo et al., "Synthesis and Conformational Analysis of N-glycopeptides that Contain Extended Sugar Chains," *Tetrahedron*, vol. 50, No. 8, 1994, pp. 2373-2390.
Inazu, Toshiyuki et al., "Preparation of Fmoc-asparagine Derivatives Having Natural N-Linked Oligosaccharide, and Its Application to the Synthesis of Glycopeptides," *Peptide Science*, vol. 1998, 1999, pp. 153-156. Wang, Lai-Xi et al., "Combined Chemical and Enzymatic Synthesis of a C-Glycopeptide and Its Inhibitory Activity toward Glycoamidases," *J. Am. Chem. Soc.*, vol. 119, No. 46, 1997, pp. 11137-11146.
Honda, Takeshi et al., "Synthesis and Anti-Influenza Virus Activity 4-Guanidino-7-substituted Neu5Ac2en Derivatives," *Bioorganic & Medicinal Chemistry Letters*, vol. 12, No. 15, 2002, pp. 1921-1924.
Seitz, Oliver et al., "Chemoenzymatic Solution- and Solid-Phase Synthesis of O-Glycopeptides of the Mucin Domain of MAdCAM-1. A General Route to O-LacNAc, O-Sialyl-LacNAc, and O-Sialyl-Lewis -X Peptides," *J. Am. Chem. Soc.*, vol. 119, No. 38, 1997, pp. 8766-8776.

(Continued)

*Primary Examiner* — Layla Bland
(74) *Attorney, Agent, or Firm* — Osha • Liang LLP

(57) ABSTRACT

Glycopeptide having at least one asparagine-linked oligosaccharide at a desired position of the peptide chain obtained by:
(1) esterifying hydroxyl of a resin and carboxyl of ah amino acid having amino group nitrogen protected with a fat-soluble protective group (AGFPG),
(2) removing the protective group to form a free amino group,
(3) amidating the free amino group and carboxyl of an amino acid having AGFPG,
(4) removing the protective group,
(5) repeating the steps (3) and (4),
(6) amidating the free amino group and carboxyl of the asparagine portion of an asparagine-linked oligosaccharide having AGFPG,
(7) removing the protective group,
(8) amidating the free amino group and carboxyl of an amino acid having AGFPG,
(9) repeating steps (7) and (8),
(10) removing the protective group, and
(11) cutting off the resin with an acid;
glycopeptide obtained by transferring sialic acid or a derivative thereof to the above glycopeptide.

12 Claims, No Drawings

OTHER PUBLICATIONS

Filira, F. et al., "Synthesis of *O*-glycosylated tuftsins by utilizing threonine derivatives containing an unprotected monosaccharide moiety," *Int. J. Peptide Protein Res.*, vol. 36, No. 1, 1990, pp. 86-96.

Komba, Shiro et al., "Synthesis of Tumor Associated Sialyl-T-Glycopeptides and their Immunogenicity," *J. Peptide Sci.*, vol. 6, No. 12, 2000, pp. 585-593.

Bézay, Nicole et al., "Chemoenzymatic-Chemical Synthesis of a (2-3)-Sialyl T Threonine Building Block and Its Application to the Synthesis of the N-Terminal Sequence of Leukemia-Associated Leukosialin (CD 43)," *Angew. Chem. Int. Ed.*, vol. 40, No. 12., 2001, pp. 2292-2295.

Office Action issued May 13, 2010, by the U.S. Patent and Trademark Office in related U.S. Appl. No. 10/519,983 (11 pages).

Office Action issued Nov. 12, 2009, by the USPTO in related U.S. Appl. No. 10/519,983 (Kajihara, Yasuhiro) (13 pages).

Keil, Stefanie, et al., "Towards the Development of Antitumor Vaccines: A Synthetic Conjugate of a Tumor-Associated MUCI Glycopeptide Antigen and a Tetanus Toxin Epitope"; Agnew. Chem. Int. Ed. 2001, 40, No. 2; pp. 366-369.

Greene, Theodora W., et al., "Protective Groups in Organic Synthesis (Third Edition)"; John Wiley & Sons, Inc., 1999; pp. 415-419.

Yamamoto, Naoki, et al., "Solid-Phase Synthesis of Sialylglycopeptides through Selective Esterification of the Sialic Acid Residues of an Asn-Linked Complex-Type Sialyloligosaccharide"; Angew. Chem. 2003, 115; (published online Jun. 5, 2003); pp. 2641-2644.

Yamamoto, Naoki, et al., "Selective Esterification of the Sialic Acid of an Asn-linked Complex type Sialyl-undeca-oligosaccharide for the Solid Phase Synthesis of Sialylglycopeptide"; Angew. Chem. Int. Ed. Z50572 (11 pages).

Notice of Allowance issued by the U.S. Patent and Trademark Office on Jan. 10, 2011, in related U.S. Appl. No. 10/519,983 (8 pages).

* cited by examiner

PROCESS FOR PREPARING GLYCOPEPTIDES HAVING ASPARAGINE-LINKED OLIGOSACCHARIDES, AND THE GLYCOPEPTIDES

This application is a division of application Ser. No. 10/519,983, filed Jan. 4, 2005, now U.S. Pat. No. 7,943,763 which is a 371 of PCT/JP2003/008551 filed Jul. 4, 2003, which claims priority based on Japanese patent application Nos. 2002-196821 and 2002-349166 filed Jul. 5 and Nov. 29, 2002, respectively, and which are incorporated herein by reference.

TECHNICAL FIELD

The present invention relates to a process for preparing glycopeptides having asparagine-linked oligosaccharides, and to the glycopeptides which is obtainable by the process.

BACKGROUND ART

In recent years, molecules of oligosaccharides have attracted attention as third chain life molecules following nucleic acids (DNA) and proteins. The human body is a huge cell society comprising about 60 trillion cells, and the surfaces of all the cells are covered with oligosaccharide molecules. For example, ABO blood groups are determined according to the difference of oligosaccharides over the surfaces of cells.

Oligosaccharides function in connection with the recognition of cells and interaction of cells and are key substances for the establishment of the cell society. Disturbances in the cell society lead, for example, to cancers, chronic diseases, infectious diseases and aging.

For example, it is known that when cells develop cancer, changes occur in the structure of oligosaccharides. It is also known that *Vibrio cholerae*, influenza virus, etc. ingress into cells and cause infection by recognizing and attaching to a specific oligosaccharide.

Clarification of oligosaccharide functions leads to development of pharmaceuticals and foods based on novel principles, contributing to the prevention and therapy of diseases, and a wide variety of applications are expected of oligosaccharides.

Oligosaccharides are much more complex than nucleic acids or proteins in structure because of the diversity of arrangements of simple sugars, modes or sites of linkages, lengths of chains, modes of branches and overall structures of higher order. Accordingly, biological information derived from the structures thereof is more diversified than is the case with nucleic acids and proteins. Although the importance of research on oligosaccharides has been recognized, the complexity and variety of structures thereof have delayed progress in the research on oligosaccharides unlike the studies on nucleic acids and proteins.

Many of proteins present on the surfaces of cell membranes or in serum have oligosaccharides attached thereto as described above. The molecules wherein oligosaccharides are combined covalently with proteins are termed glycoproteins, which can be divided into two groups according to the difference in the mode of linkage between the oligosaccharide and the protein. Oligosaccharides of one type are asparagine-linked oligosaccharides (N-glycoside linkage type) wherein an amino group of the side chain of asparagine (Asn) is linked with the oligosaccharide. Oligosaccharides of the other type are mucin-linked oligosaccharides (O-glycoside linkage type) wherein the oligosaccharide is linked with the alcohol of serine (Ser) or threonine (Thr). All the asparagine-linked oligosaccharides have a basic skeleton comprising five sugar residues, and are divided into subgroups of high-mannose type, composite type and mixture type, according to the kind of the nonreducing terminal sugar residue of the oligosaccharide linked. On the other hand, the mucin-liked oligosaccharides are divided into four groups according to the difference of the basic skeleton.

The process for preparing peptides which is presently in wide use is the solid-phase synthesis process developed by R. B. Merrifield in 1963. The solid-phase synthesis process is such that amino acids are linked to a solid phase called a resin to provide a lengthened peptide chain. When completely lengthened, the peptide chain is cut off from the solid phase to obtain the desired product. As an application of this process, a glycopeptide chain can be prepared by incorporating an amino acid having an oligosaccharide linked thereto into the peptide chain to be lengthened.

Accordingly, glycopeptide chains are widely prepared by using amino acid-linked oligosaccharides wherein an oligosaccharide is linked with Asn or Ser(Thr) for the preparation of peptides. However, there are only a few examples of chemically preparing peptide chains having a great sugar chain despite of technical progress in chemical synthesis.

One of the problems to be encountered is insufficient absolute amounts of oligosaccharides to be linked with the asparagine residue. Methods of obtaining oligosaccharides include isolation of oligosaccharides only from glycoproteins which are present in the living body. However, hydrazine for use in cutting off oligosaccharides from glycoproteins is hazardous, presenting difficulty in preparing large quantities of oligosaccharides. Further there are in the living body many oligosaccharides which closely resemble in structure, and it is difficult to obtain a single oligosaccharide only. Further since decomposition of hydrazine releases the oligosaccharide from the asparagine residue, there arises a need to link the released oligosaccharide with the asparagine residue again, hence an increased number of steps needed.

In chemically synthesizing oligosaccharides, there are examples of preparing oligosaccharides wherein about 10 sugar residues are linked, whereas many of these cases are such that the desired oligosaccharide can be prepared in an amount of only several milligrams during one year. For this reason, difficulties are encountered in chemically preparing oligosaccharides.

The second of the problems is involved in the treatment conducted with use of TFA (trifluoroacetic acid) for cutting off the peptide chain from the solid phase. For example, sialic acid present at the nonreducing terminals of oligosaccharides is readily hydrolyzed under an acid condition, so that there is the possibility that the TFA treatment will cut off sialic acid from the glycopeptide prepared. Accordingly, there is almost no case wherein oligosaccharides having sialic acid are used for solid-phase synthesis. To solve this problem, a process has been reported wherein sialic acid is transferred to an oligosaccharide with sialic acid transferase after peptide synthesis. Although useful for introducing sialic acid, this process still has the problem that difficulty is encountered in preparing glycopeptides in large quantities because the transferase is expensive.

As will be described below, however, the present invention has made it possible to artificially prepare glycopeptides in large amounts. Accordingly, it becomes possible to industrially introduce sialic acid or derivatives thereof into oligosaccharides using the sialic acid transferase.

Although there are naturally occurring oligosaccharides which have sialic acid linked thereto, oligosaccharides having sialic acid derivatives linked thereto are naturally unavailable. Thus, it is through the use of the sialic acid transferase that sialic acid derivatives can be introduced into oligosaccharides in any way.

An object of the present invention is to provide a process capable of artificially and easily preparing a large amount of a glycopeptide having at least one asparagine-linked oligosaccharide or mucin-linked oligosaccharide at a desired position of the peptide chain thereof.

Another object of the present invention is to provide a process for easily preparing a sialylglycopeptide which comprises an asparagine-linked oligosaccharide having sialic acid and wherein the sialic acid is not cut off from the glycopeptide by an acid treatment.

Another object of the present invention is to provide a process for artificially and easily preparing a large quantity of a glycopeptide having at least one of various novel asparagine-linked oligosaccharides at a desired position of the peptide chain thereof, with sugar residues removed therefrom as desired.

Another object of the present invention is to provide a process for preparing a glycopeptide having sialic acid or a derivative thereof introduced into the peptide with use of a sialic acid transferase.

Still another object of the invention is to provide glycopeptides which is obtainable by the above processes for preparing glycopeptides.

DISCLOSURE OF THE INVENTION

The present invention provides a process for preparing a glycopeptide having at least one asparagine-linked oligosaccharide at a desired position of the peptide chain thereof, the process comprising:
(1) esterifying a hydroxyl group of a resin having the hydroxyl group and a carboxyl group of an amino acid having amino group nitrogen protected with a fat-soluble protective group,
(2) removing the fat-soluble protective group to form a free amino group,
(3) amidating the free amino group and a carboxyl group of an amino acid having amino group nitrogen protected with a fat-soluble protective group,
(4) removing the fat-soluble protective group to form a free amino group,
(5) repeating the steps (3) and (4) at least once,
(6) amidating the free amino group and a carboxyl group of the asparagine portion of an asparagine-linked oligosaccharide having amino group nitrogen protected with a fat-soluble protective group,
(7) removing the fat-soluble protective group to form a free amino group,
(8) amidating the free amino group and a carboxyl group of an amino acid having amino group nitrogen protected with a fat-soluble protective group,
(9) repeating the steps (7) and (8) at least once,
(10) removing the fat-soluble protective group to form a free amino group, and
(11) cutting off the resin with an acid.

The present invention provides a process for preparing a glycopeptide having at least two asparagine-linked oligosaccharides at a desired position of the peptide chain thereof which comprises the process wherein the steps (6) of amidating the free amino group and a carboxyl group of the asparagine portion of an asparagine-linked oligosaccharide having amino group nitrogen protected with a fat-soluble protective group, and (7) of removing the fat-soluble protective group to form a free amino group are additionally performed suitably.

The present invention provides a process for preparing a glycopeptide having at least one asparagine-linked oligosaccharide at a desired position of the peptide chain thereof wherein the steps (6) of amidating the free amino group and the carboxyl group of the asparagine portion of an asparagine-linked oligosaccharide having amino group nitrogen protected with a fat-soluble protective group, and (7) of removing the fat-soluble protective group to form a free amino group are performed as final steps.

The present invention provides a process for preparing a glycopeptide wherein the step (1) of esterifying a hydroxyl group of a resin having the hydroxyl group and a carboxyl group of an amino acid having amino group nitrogen protected with a fat-soluble protective group is performed in place of the step (6) or in addition to the step (6).

The present invention provides a process for preparing a glycopeptide wherein the asparagine-linked oligosaccharide of the step (6) has at least 6 sugar residues.

The present invention provides a process for preparing a glycopeptide wherein the asparagine-linked oligosaccharide of the step (6) has 9 to 11 sugar residues.

The present invention provides a process for preparing a glycopeptide wherein the asparagine-linked oligosaccharide of the step (6) has at least 6 sugar residues, and has a bifurcated oligosaccharide attached thereto.

The present invention provides a process for preparing a glycopeptide wherein the asparagine-linked oligosaccharide in (6) is an asparagine-linked disialooligosaccharide or an asparagine-linked monosialooligosaccharide in which the carboxyl group of the sialic acid is protected with a protective group.

The present invention provides a process for preparing a glycopeptide wherein the asparagine-linked oligosaccharide in (6) is an asparagine-linked asialooligosaccharide.

The present invention provides a process for preparing a glycopeptide wherein a mucin-linked oligosaccharide is used in place of a portion or the whole of the asparagine-linked oligosaccharide.

The present invention provides a glycopeptide which is obtainable by the above processes and which has at least one asparagine-linked oligosaccharide or mutin-linked oligosaccharide at a desired position of the peptide chain thereof.

The present invention provides a glycopeptide wherein the asparagine-linked oligosaccharide or the mutin-linked oligosaccharide has at least 6 sugar residues, and has a bifurcated oligosaccharide attached thereto.

The present invention provides a glycopeptide which is a glycopeptide having at least one oligosaccharide selected from among asparagine-linked disialooligosaccharide and asparagine-linked monosialooligosaccharide attached as the asparagine-linked oligosaccharide.

The present invention provides a process for preparing glycopeptide having at least one asparagine-linked oligosaccharide at a desired position of the peptide chain thereof and a residue of sialic acid or a derivative thereof at a terminal end thereof, the process comprising:
(1) esterifying a hydroxyl group of a resin having the hydroxyl group and a carboxyl group of an amino acid having amino group nitrogen protected with a fat-soluble protective group,
(2) removing the fat-soluble protective group to form a free amino group, (3) amidating the free amino group and a carboxyl group of an amino acid having amino group nitrogen protected with a fat-soluble protective group,
(4) removing the fat-soluble protective group to form a free amino group,
(5) repeating the steps (3) and (4) at least once,
(6) amidating the free amino group and a carboxyl group of the asparagine portion of an asparagine-linked oligosaccharide having amino group nitrogen protected with a fat-soluble protective group,
(7) removing the fat-soluble protective group to form a free amino group,
(8) amidating the free amino group and a carboxyl group of an amino acid having amino group nitrogen protected with a fat-soluble protective group,
(9) repeating the steps (7) and (8) at least once,
(10) removing the fat-soluble protective group to form a free amino group,
(11) cutting off the resin with an acid, and
(12) transferring sialic acid or a derivative thereof to the resulting glycopeptide using a sialic acid transferase.

The present invention provides a process for preparing a glycopeptide wherein a marker is reacted with the resin before the resin is cut off with the acid in step (11).

The present invention provides a process for preparing a glycopeptide wherein the marker is a dansyl halide.

The present invention provides a process for preparing 5-acetamido-3,5,7-trideoxy-7-fluoro-D-glycero-β-D-lacto-2-nonulopyranosidonic acid comprising reacting N-acetyl-4-deoxy-4-fluoro-D-mannosamine, sodium piruvate, bovine serum albumin and aldolase sialate.

The present invention provides a process for preparing 5-acetamido-3,5,7-trideoxy-7-fluoro-D-glycero-β-D-lacto-2-nonulopyranosidonic acid comprising hydrogenating benzyl 2-azido-2,4-dideoxy-4-fluoro-β-D-mannopyranoside in the presence of acetic anhydride to obtain N-acetyl-4-deoxy-4-fluoro-D-mannosamine, and subsequently reacting the product with sodium piruvate, bovine serum albumin and aldolase sialate.

The present inventor has already developed, as disclosed in Japanese Patent Application No. 2001-185685 (hereinafter referred to as the "prior application"), processes for preparing asparagine-linked oligosaccharides derivative, asparagine-linked oligosaccharides and oligosaccharides which processes are capable of producing various isolated asparagine-linked oligosaccharides derivative with greater ease and in larger quantities than conventionally, and further novel asparagine-linked oligosaccharides derivative, asparagine-linked oligosaccharides and oligosaccharides, wherein oligosaccharides deficient in sugar residues as desired are linked.

The processes of the prior application include:
(1) a process for preparing an asparagine-linked oligosaccharide derivative derived from an asparagine-linked oligosaccharide which process includes the steps of:
    (a) introducing a fat-soluble protective group into an asparagine-linked oligosaccharide or at least two asparagine-linked oligosaccharides included in a mixture comprising the oligosaccharide or said at least two oligosaccharides to obtain an asparagine-linked oligosaccharide derivative mixture, and
    (b) hydrolyzing the asparagine-linked oligosaccharide derivative mixture or asparagine-linked oligosaccharides derivative included in this mixture and subjecting the resulting mixture to chromatography to separate off asparagine-linked oligosaccharides derivative, (2) a process for preparing an asparagine-linked oligosaccharide derivative according to (1) which further includes the step (b') of hydrolyzing the asparagine-linked oligosaccharides derivative separated off by the step (b) with a sugar hydrolase,
(3) a process for preparing an asparagine-linked oligosaccharide derivative according to (1) or (2) wherein the mixture comprising the oligosaccharide or said at least two oligosaccharides includes a compound of the formula (A) below and/or a compound corresponding to said compound wherein at least one sugar residue is deficient,
(4) a process for preparing an asparagine-linked oligosaccharide derivative according to any one of (1) to (3) wherein the fat-soluble protective group is a fluorenylmethoxycarbonyl (Fmoc) group,
(5) a process for preparing an asparagine-linked oligosaccharide derivative according to any one of (1) to (3) wherein the step (a) is the step of introducing Fmoc group into the asparagine-linked oligosaccharide or said at least two asparagine-linked oligosaccharides having a sialic residue at a nonreducing terminal and included in the mixture, and introducing benzyl group into the sialic residue to obtain the asparagine-linked oligosaccharide derivative mixture,
(6) A process for preparing an asparagine-linked oligosaccharide including the steps of:
    (a) introducing a fat-soluble protective group into an asparagine-linked oligosaccharide or at least two asparagine-linked oligosaccharides included in a mixture comprising the oligosaccharide or said at least two oligosaccharides to obtain an asparagine-linked oligosaccharide derivative mixture,
    (b) hydrolyzing the asparagine-linked oligosaccharide derivative mixture or asparagine-linked oligosaccharides derivative included in this mixture and subjecting the resulting mixture to chromatography to separate off asparagine-linked oligosaccharides derivative, and
    (c) removing the protective group from the asparagine-linked oligosaccharides derivative separated off in the step (b) to obtain asparagine-linked oligosaccharides,
(7) a process for preparing an asparagine-linked oligosaccharide according to (6) which further includes:
    the step (b') of hydrolyzing the asparagine-linked oligosaccharides derivative separated off by the step (b) with a sugar hydrolase, and/or
    the step (c') of hydrolyzing the asparagine-linked oligosaccharides obtained by the step (c) with a sugar hydrolase,
(8) a process for preparing an asparagine-linked oligosaccharide according to (6) or (7) wherein the mixture comprising the oligosaccharide or said at least two oligosaccharides includes a compound of the formula (A) below and/or a compound corresponding to said compound wherein at least one sugar residue is deficient,
(9) a process for preparing an asparagine-linked oligosaccharide according to any one of (6) to (8) wherein the fat-soluble protective group is Fmoc group.
(10) a process for preparing an asparagine-linked oligosaccharide according to any one of (6) to (8) wherein the step (a) is the step of introducing Fmoc group into the asparagine-linked oligosaccharide or said at least two asparagine-linked oligosaccharides having a sialic residue at a nonreducing terminal and included in the mixture, and introducing benzyl group into the sialic residue to obtain the asparagine-linked oligosaccharide derivative mixture, etc.

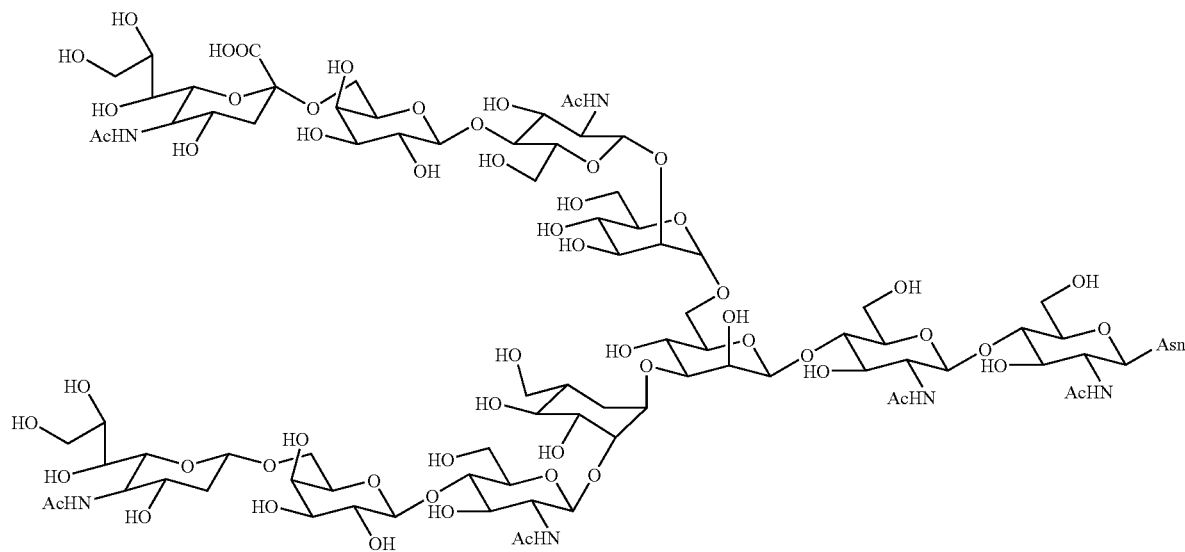
(A)

The above asparagine-linked oligosaccharide derivative is represented, for example, by the formula (6).

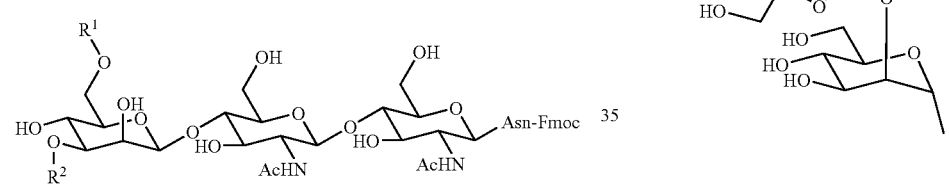
(6)

wherein $R^1$ and $R^2$ are each a hydrogen atom or a group represented by one of the formula (2) to (5), and may be the same or different except that $R^1$ and $R^2$ are each the group of the formula (3).

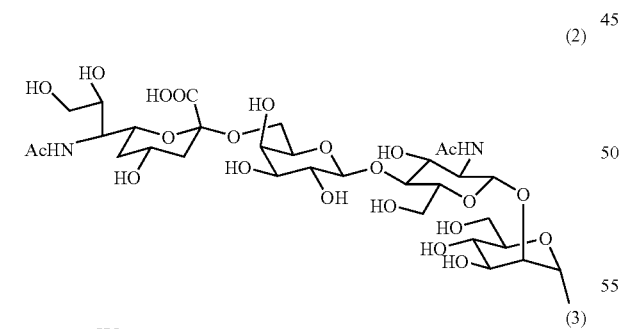
(2)

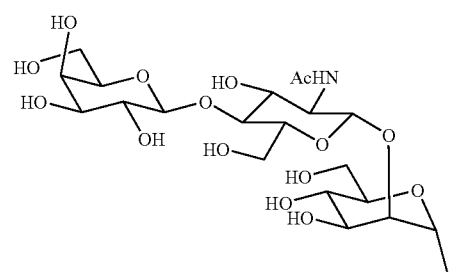
(3)

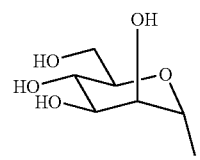
(4)

(5)

Another asparagine-linked oligosaccharide derivative is represented, for example, by the formula (7).

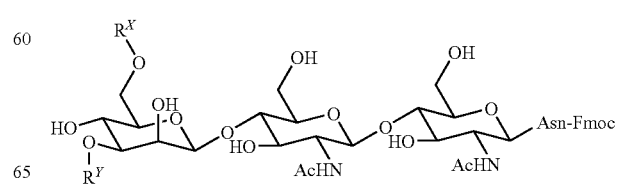
(7)

wherein one of $R^x$ and $R^y$ is a group represented by the formula (8), and the other is a hydrogen atom or a group represented by one of the formulae (2) to (5) and (8).

(8)

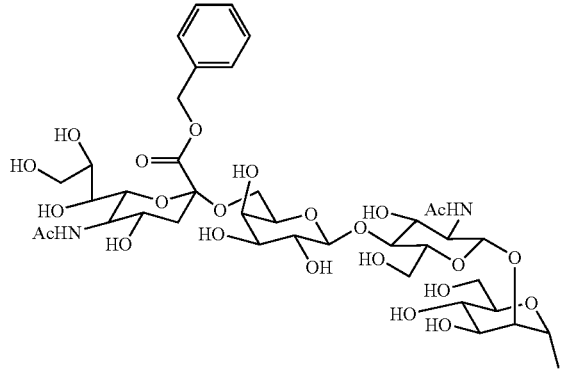

The above asparagine-linked oligosaccharide is represented, for example, by the formula (1).

(1)

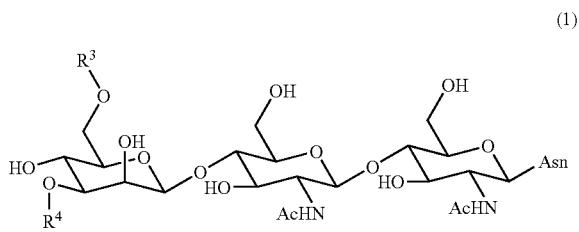

wherein $R^3$ and $R^4$ are each a hydrogen atom or a group represented by one of the formula (2) to (5), and may be the same or different except that $R^3$ and $R^4$ are each the group of the formula (2) or the formula (3).

Since a detailed description is given in the prior application about the preparation of these asparagine-linked oligosaccharide derivatives and asparagine-linked oligosaccharides, reference will be made to the application. However, what is disclosed in the prior application will be described to some extent. The process of the prior application for preparing asparagine-linked oligosaccharides derivative is distinctly characterized in that a fat-soluble protective group is introduced into (linked with) a asparagine-linked oligosaccharide derived from a naturally occurring glycoprotein, preferably asparagine-linked oligosaccharides included in a mixture of asparagine-linked oligosaccharides obtained from oligosaccharides capable of linking to asparagine, to obtain a mixture of asparagine-linked oligosaccharides derivative, followed by separation of the mixture into individual asparagine-linked oligosaccharides derivative. The term an "asparagine-linked oligosaccharide" as used herein refers to an oligosaccharide having asparagine linked thereto. Further the term "oligosaccharides capable of linking to asparagine" refers to a group of oligosaccharides wherein N-acetylglucosamine present at a reducing terminal is attached by N-glucoside linkage to the acid amino group of asparagine (Asn) in the polypeptide of a protein and which has Man(β1-4)GlcNac (β1-4)GlcNac as the mother nucleus. The term an "asparagine-linked oligosaccharide derivative" refers to an asparagine-linked oligosaccharide wherein a fat-soluble protective group is attached to asparagine residue. Further "AcHN" in the structural formulae of compounds refers to an acetamido group.

As described previously, oligosaccharides derived from naturally occurring glycoproteins are a mixture of oligosaccharides which are randomly deficient in the sugar residue at the nonreducing terminal. The present inventors have unexpectedly found that the introduction of a fat-soluble protective group into an oligosaccharide derived from a naturally occurring glycoprotein, preferably into asparagine-linked oligosaccharides included in a mixture thereof, makes it possible to readily separate a mixture of asparagine-linked oligosaccharides derivative having the protective group introduced therein into individual asparagine-linked oligosaccharides derivative by a known chromatographic procedure. Consequently, asparagine-linked oligosaccharides derivative having different structures can be prepared individually in large quantities. For example, asparagine-linked oligosaccharides derivative which resemble in structure and which are conventionally difficult to separate can be separated from one another, and these compounds can be prepared easily in large quantities. Further a sugar hydrolase can be caused to act on the resulting asparagine-linked oligosaccharides derivative and thereby prepare various asparagine-linked oligosaccharides derivative.

Thus, introducing a fat-soluble protective group into asparagine-linked oligosaccharides provides derivatives and makes it possible to separate the asparagine-linked oligosaccharides derivative from one another. Presumably this is attributable to the fact that the introduction of the fat-soluble protective group gives improved fat solubility to the whole asparagine-linked oligosaccharides derivative to ensure remarkably improved interaction between the oligosaccharide and the reverse-phase column to be used favorably, consequently separating the asparagine-linked oligosaccharides derivative from one another by reflecting the difference of structure between the oligosaccharides with high sensitivity.

Further by removing the protective group from the asparagine-linked oligosaccharides derivative obtained, various asparagine-linked oligosaccharides can be artificially prepared easily in large amounts according to the prior application.

The process of the present invention provides the desired glycopeptides using various asparagine-linked oligosaccharides obtained by the prior application.

In the process of the present invention, (1) subjected to an esterifying reaction are a hydroxyl group of a resin having the hydroxyl group and a carboxyl group of an amino acid having amino group nitrogen protected with a fat-soluble protective group.

Since the amino group nitrogen of the amino acid is protected with a fat-soluble protective group, the hydroxyl group of the resin is reacted with the carboxyl group of the amino acid, with self-condensation of the amino acid prevented.

Next, (2) the fat-soluble protective group is removed from the resulting ester to form a free amino group,
(3) the free amino group is amidated with a carboxyl group of a desired amino acid having amino group nitrogen protected with a fat-soluble protective group,
(4) the fat-soluble protective group is removed to form a free amino group, and
(5) the steps (3) and (4) are repeated at least once to thereby obtain a peptide having a desired number of desired amino acids as linked and having the resin attached to one end thereof and a free amino group at the other end thereof.

Next, (6) the free amino group is amidated with a carboxyl group of the asparagine portion of an asparagine-linked oligosaccharide having amino group nitrogen protected with a fat-soluble protective group, (7) the fat-soluble protective group is removed to form a free amino group, (8) the free amino group is amidated with a carboxyl group of a desired amino acid having amino group nitrogen protected with a fat-soluble protective group, (9) the steps (7) and (8) are repeated at least once, and

(10) the fat-soluble protective group is removed to form a free amino group and thereby obtain a glycopeptide having a desired number of desired amino acids as linked and having the resin attached to one end thereof, a free amino group at the other end thereof and an asparagine-linked oligosaccharide at an intermediate position.

(11) The resin is cut off with an acid, whereby a glycopeptide can be prepared which has an asparagine-linked oligosaccharide at a desired position of the peptide chain thereof.

Furthermore, a glycopeptide having at least two asparagine-linked oligosaccharides at a desired position of the peptide chain thereof can be prepared by suitably adding the step (6) of amidating the free amino group and a carboxyl group of the asparagine portion of an asparagine-linked oligosaccharide having amino group nitrogen protected with a fat-soluble protective group. At this time, a glycopeptide having at least two kinds of asparagine-linked oligosaccharides at a desired position of the peptide chain thereof can be prepared by using a different asparagine-linked oligosaccharide.

Alternatively, the asparagine-linked oligosaccharide can be introduced into an end portion of the peptide chain.

Furthermore, a mucin-linked oligosaccharide can be used in place of a portion or whole of the asparagine-linked oligosaccharide.

The resin having a hydroxyl group for use in the present invention may usually be a resin having hydroxyl useful for solid-phase synthesis. Examples of resins usable are Wang resin (product of Merk), HMPA-PEGA resin (product of Merk), etc.

All amino acids are usable as such. Examples of amino acids usable are serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe) tryptophan (Trp) and proline (Pro).

Examples of fat-soluble protective groups are 9-fluorenylmethoxycarbonyl (Fmoc) group, tert-butyloxycarbonyl (Boc) group, benzyl group, allyl group, allyloxycarbonyl group, acetyl group and like carbonate-type or amide-type protective groups. The fat-soluble protective group, e.g., Fmoc group, can be introduced by adding 9-fluorenylmethyl-N-succinimidyl carbonate and sodium hydrogencarbonate to the contemplated compound for reaction. The reaction is conducted at 0 to 50° C., preferably at room temperature, for about 1 to about 5 hours.

The above amino acid can be protected with a fat-soluble protective group by the method described above. The above protected amino acid can be those available commercially. Examples are Fmoc-Ser, Fmoc-Asn, Fmoc-Val, Fmoc-Leu, Fmoc-Ile, Fmoc-Ala, Fmoc-Tyr, Fmoc-Gly, Fmoc-Lys, Fmoc-Arg, Fmoc-His, Fmoc-Asp, Fmoc-Glu, Fmoc-Gln, Fmoc-Thr, Fmoc-Cys, Fmoc-Met, Fmoc-Phe, Fmoc-Trp and Fmoc-Pro.

Usable as esterifying catalysts are dehydrating condensation agents such as 1-mesitylenesulfonyl-3-nitro-1,2,4-triazole (MSNT), dicyclohexylcarbodiimide (DCC) and diisopropylcarbodiimide (DIPCDI). The esterifying reaction is conducted preferably by placing a resin, for example, into a solid-phase column, washing the resin with a solvent and thereafter adding a solution of amino acid in a solvent to the resin. Examples of solvents for washing are dimethylformamide (DMF), 2-propanol, methylene chloride, etc. Examples of solvents for dissolving amino acids are dimethyl sulfoxide (DMSO), DMF, methylene chloride, etc. The reaction is conducted at 0 to 50° C., preferably at room temperature, for about 10 to about 30 hours, preferably about 15 minutes to about 24 hours.

Preferably, the unreacted hydroxyl group remaining on the solid phase at this time is acetylated, for example, with acetic anhydride for capping.

The fat-soluble protective group can be removed, for example, by a treatment with a base. Examples of bases to be used are piperidine, morpholine, etc. This treatment is conducted preferably in the presence of a solvent. Examples of solvents usable are DMSO, DMF, methanol, etc.

The reaction of amidating the free amino group with a carboxyl group of a desired amino acid having amino group nitrogen protected with the fat-soluble group is conducted, preferably in the presence of an activator and a solvent.

Examples of useful activators are dicyclohexylcarbodiimide (DCC), 1-ethyl-3-(3-dimethylaminopropyl)carbodiimide hydrochloride (WSC/HCl), diphenylphosphorylazide (DPPA), carbonyldiimidazole (CDI), diethylcyanophosphonate (DEPC), benzotriazole-1-yloxy-trispyrrolidinophosphonium (DIPCI), benzotriazole-1-yloxy-trispyrrolidino-phosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazole-1-yl)-1,1,3,3-tetramethyluronium hexafluorophosphate (HBTU), O-(7-azabenzotriazole-1-yl)-1,1,3,3-tetramethyluronium hexafluorophosphonate (HATU), O-benzotriazole-1-yl-1,1,3,3-tetramethyluronium tetrafluoroborate (TBTU), 3,4-dihydro-3-hydrodi-4-oxa-1,2,3-benzotriazine (Dhbt).

The activator is used in an amount of 1 to 20 equivalents, preferably 1 to 10 equivalents, more preferably 1 to 5 equivalents, based on an amino acid having amino group nitrogen protected with a fat-soluble protective group.

Examples of useful solvents are DMSO, DMF, methylene chloride, etc. It is desired that the reaction be conducted at 0 to 50° C., preferably at room temperature, for about 10 to about 30 hours, preferably about 15 minutes to about 24 hours. It is desired that the unreacted hydroxyl group remaining on the solid phase at this time be acetylated, for example, with acetic anhydride for capping. The fat-soluble protective group can be removed in the same manner as described above.

The peptide chain is cut off from the resin, preferably by a treatment with an acid. Examples of acids to be used are trifluoroacetic acid (TFA), hydrogen fluoride (HF), etc.

According to the invention, a glycopeptide having at least two asparagine-linked oligosaccharides at a desired position of the peptide chain thereof can be prepared by suitably additionally performing the steps (6) of amidating the free amino group and a carboxyl group of the asparagine portion of an asparagine-linked oligosaccharide having amino group nitrogen protected with a fat-soluble protective group, and (7) of removing the fat-soluble protective group to form a free amino group.

Further according to the invention, a glycopeptide having at least one asparagine-linked oligosaccharide at a desired position of the peptide chain thereof can be prepared by performing as final steps the steps (6) of amidating the free amino group and the carboxyl group of the asparagine portion of an asparagine-linked oligosaccharide having amino group nitrogen protected with a fat-soluble protective group, and (7) of removing the fat-soluble protective group to form a free amino group.

Further according to the invention, a glycopeptide having an asparagine-linked oligosaccharide at an end portion can be prepared by performing the step (1) of esterifying a hydroxyl group of a resin having the hydroxyl group and a carboxyl group of an amino acid having amino group nitrogen protected with a fat-soluble protective group, in place of the step (6) or in addition to the step (6).

The asparagine-linked oligosaccharides to be used in the present invention can be those having a desired number of sugar residues. An asparagine-linked oligosaccharide or mucin-linked oligosaccharide is especially usable which has at least six sugar residues and which has not been used conventionally. This is a unique feature of the invention. It is also possible to use asparagine-linked oligosaccharides having 9 to 11 sugar residues.

It is further possible to use asparagine-linked oligosaccharides of the bifurcated type which has at least six sugar residues. For example, the asparagine-linked oligosaccharide to be used can be an asparagine-linked disialooligosaccharide or asparagine-linked monosialooligosaccharide. Glycopeptides incorporating such an asparagine-linked disialooligosaccharide or asparagine-linked monosialooligosaccharide are preferred glycopeptides of the invention.

The asparagine-linked oligosaccharide to be used can be an asparagine-linked disialooligosaccharide or asparagine-linked monosialooligosaccharide wherein the carboxyl group of sialic acid is protected with a protective group.

In the case of the asparagine-linked oligosaccharide or mucin-linked oligosaccharide for use in the invention, the oligosaccharide may have its hydroxyl protected. Examples of protective groups useable are acetyl, triethylsilyl, etc. Preferably, the protective group is one which can be treated with an acid simultaneously when the resin is cut off from the glycopeptide prepared. For example, triethylsilyl is useful as such.

In the case where the asparagine-linked oligosaccharide is an asparagine-linked disialooligosaccharide or asparagine-linked monosialooligosaccharide, there is a likelihood that the sialic acid will be cut off with an acid, so that such oligosaccharides wherein the carboxyl group of sialic acid is protected with a protective group are desirable since the sialic acid is then prevented from being cut off. Examples of protective groups to be used are benzyl, allyl, diphenylmethyl group, etc.

The reaction for introducing a protective group into the carboxyl group of sialic acid can be conducted in a known manner, for example, as disclosed in "Protective Groups in Organic Chemistry," John Wiley & Sons INC., New York 1991, ISBN 0-471-62301-6.

According to the invention, derivatives of sialic acid are those wherein the hydroxyl group attached to the carbon atom at the 7-position, 8-position or 9-position of the sialic acid is replaced by a hydrogen atom or halogen atom. Examples of halogen atoms are fluorine, chlorine, bromine and the like, among which fluorine is preferred.

The sialic acid transferase to be used in the present invention can be those generally available commercially. A suitable transferase is selectable in accordance with the kind of contemplated sialic acid or sialic acid derivative and the mode of linkage. Examples of useful transferases are those derived from a rat recombinant and rat liver. Sialytase may be used for pH adjustment to shift the equilibrium and effect a transfer reaction for sialic acid or a derivative thereof.

The glycopeptides of the invention are very useful in the field of development of pharmaceuticals. For example, vaccines for cancers are an example of application to the development of drugs. It is known that cells developing cancer produce an oligosaccharide which is not found in the living body. It is also known that when chemically prepared and given to the human body as a vaccine, such an oligosaccharide inhibits the growth of cancer. If the desired glycopeptide can be produced according to the invention, it is possible to prepare a vaccine which is effective for treating cancer. The glycopeptide obtained by the invention can further be made into derivatives by attaching novel sugar residues thereto through combinations of chemical reactions and reactions of sugar transferases for the preparation of novel vaccines.

Glycopeptides exhibit higher solubility in water than peptides which are not combined with oligosaccharides, while they are highly stable when in the form of aqueous solutions and when present in blood.

The sialic acid at the nonreducing terminal, when made into a derivative, prevents the decomposition of the oligosaccharide itself, thereby giving enhanced stability to the glycopeptide.

Furthermore, the sialic acid at the nonreducing terminal, as made into a derivative is a nonnatural-type oligosaccharide and can therefore be effective for the preparation of vaccines.

BEST MODE OF CARRYING OUT THE INVENTION

The present invention will be described below with reference to examples, to which the invention is not limited.

Used in the following examples are Fmoc-Val, Fmoc-Leu, Fmoc-Leu-Opfp, Fmoc-Ala, Fmoc-Ala-Opfp, Fmoc-Val-Opfp, Fmoc-Ser(Bzl)-OH and Fmoc-Ser(OtBu) which are known substances. Commercial products are used as these substances. For example, Opfp in Leu-Opfp stands for leucine (Leu) having the carboxyl group thereof protected with pentafluorophenyl (pfp), Ser(Bzl)-OH for serine (Ser) having the hydroxyl thereof protected with benzyl (Bzl), and Ser (OtBu)-OH for serine (Ser) having the hydroxyl thereof protected with t-butyl (tBu).

REFERENCE EXAMPLE 1

Preparation of Asparagine-linked Disialooligosaccharide (10)

A 500 mg quantity of roughly purified SGP (sialylglycopeptide) and 10 mg (319 μmols) of sodium azide were dissolved in 25 ml of tris-hydrochloric acid-calcium chloride buffer solution (0.05 mol/l of TRIZMA BASE, 0.01 mol/l of calcium chloride, pH=7.5). To the solution was added a solution of 50 mg of actinase E (protease, product of Kaken Seiyaku) in 5 ml of tris-hydrochloric acid-calcium chloride buffer solution, followed by standing at 37° C. The solution was freeze-dried 115 hours later. The residue was purified by gel filtration column chromatography twice, giving 252 mg of the desired product, i.e., Asparagine-linked disialooligosaccharide (10).

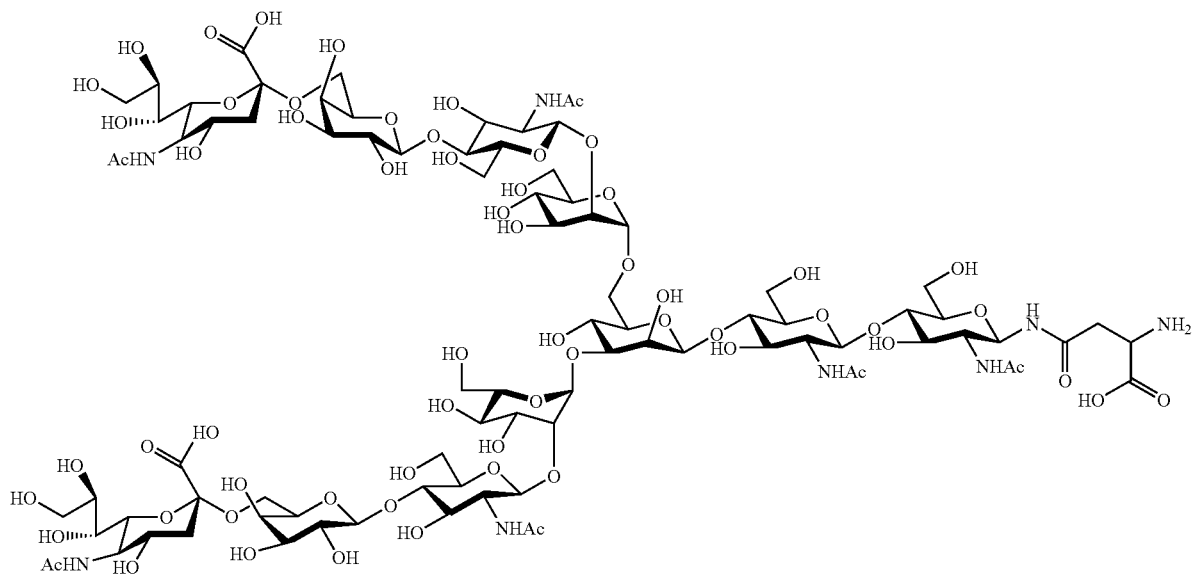

(10)

$^1$H-NMR (30° C.) δ 5.13 (s, 1H, Man4-H-1), 5.07 (d, 1H, J=9.5 Hz, GlcNAc1-H-1), 4.95 (s, 1H, Man4'-H-1), 4.77 (s, 1H, Man3-H-1), 4.61 (d, 1H, J=7.6 Hz, GlcNAc2-H-1), 4.60 (d, 2H, J=7.6 Hz, GlcNAc5, 5'-H-1), 4.44 (d, 2H, J=8.0 Hz, Gal6, 6'-H-1), 4.25 (bd, 1H, Man3-H-2), 4.20 (bdd, 1H, Man4-H-2), 4.12 (bd, 1H, Man4'-H-2), 2.94 (dd, 1H, J=4.5 Hz, 17.2 Hz, Asn-βCH), 2.85 (dd, 1H, J=7.0 Hz, 17.2 Hz, Asn-βCH), 2.67, 2.66 (dd, 2H, J=4.6 Hz, 12.4 Hz, NeuAc7, 7'-H-3$_{eq}$), 2.07 (s, 3H, Ac), 2.06 (s, 6H, Ac×2), 2.02 (s, 6H, Ac×2), 2.01 (s, 3H, Ac), 1.71 (dd, 2H, J=12.4 Hz, 12.4 Hz, NeuAc7, 7'-H-3$_{ax}$).

REFERENCE EXAMPLE 2

Preparation of Asparagine-linked Disialooligosaccharide (11) Wherein Amino Group Nitrogen of Asparagine is Protected with Fmoc Group An 80 mg quantity (0.034 mmol) of the asparagine-linked disialooligosaccharide obtained in Reference Example 1 was dissolved in a solution of 2.7 ml of distilled water and 4.1 ml of acetone, and to the solution were added 34.7 mg (0.103 mmol) of 9-fluorenylmethyl-N-succinimidyl carbonate (Fmoc-OSn) and 11.5 mg (0.137 mmol) of sodium hydrogencarbonate. The mixture was stirred at room temperature for 2 hours. After the completion of reaction was recognized by TLC, the resulting solution was concentrated in a vacuum to remove acetone. The residue was applied to a column (ODS column) filled with a silica gel having octadecylsilyl group attached thereto) for purification, affording 60.1 mg of the desired product, i.e., Fmoc-asparagine-linked disialooligosaccharide (11) in a yield of 68%.

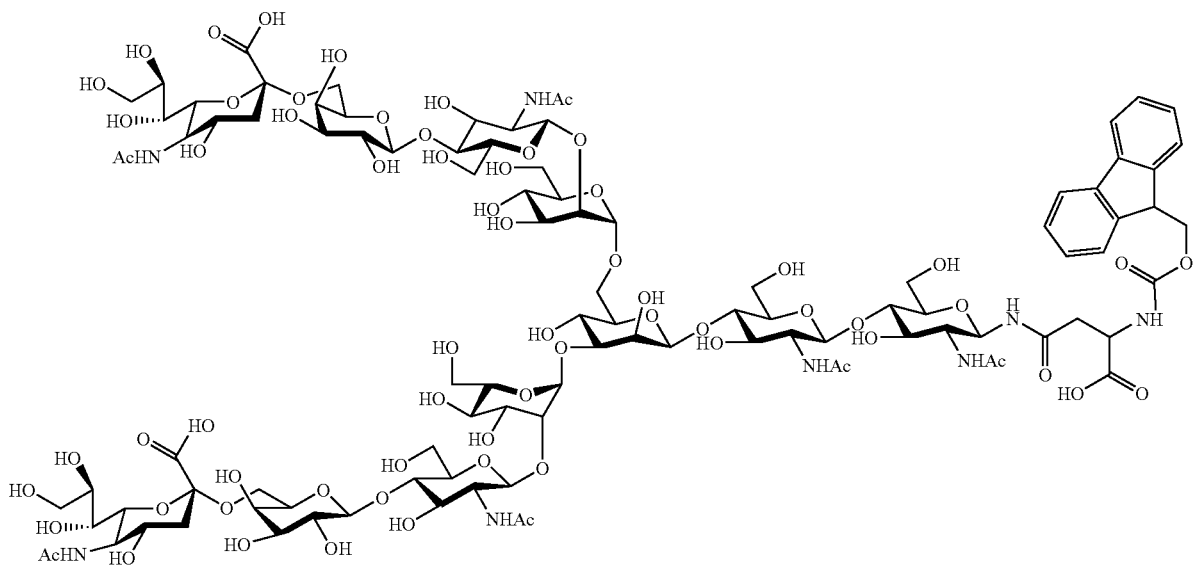

(11)

$^1$H-NMR (30° C.) 8.01 (2H, d, J=7.5 Hz, Fmoc), 7.80 (2H, d, J=7.5 Hz, Fmoc), 7.60 (2H, dd, J=7.5 Hz, Fmoc), 7.53 (2H, dd, J=7.5 Hz, Fmoc), 5.23 (1H, s, Man4-H$_1$), 5.09 (1H, d, J=9.4 Hz, GlcNAc1-H$_1$), 5.04 (1H, s, Man4'-H$_1$), 4.86 (1H, s, Man3-H$_1$), 4.70~4.66 (m, GlcNAc2-H$_1$ GlcNAc5, 5'-H$_1$), 4.54 (2H, d, J=7.9 Hz, Gal6, 6'-H$_1$), 4.44 (1H, d, FmocCH), 4.34 (1H, bd, Man3-H$_2$), 4.29, (1H, bd, Man4'-H$_2$), 4.20 (1H, bd, Man4-H$_2$), 2.77 (2H, dd, NeuAc7, 7'-H$_{3eq}$), 2.80 (1H, bdd, Asn-βCH), 2.62 (1H, bdd, Asn-βCH), 2.14 (18H, s×6, -Ac), 1.80 (2H, dd, NeuAc7, 7'-H$_{3ax}$)

REFERENCE EXAMPLE 3

Preparation of Asparagine-Linked Disialooligosaccharide (12) Wherein Amino Group Nitrogen of Asparagine is Protected with Fmoc Group, and Carboxyl Group of Sialic Acid is Protected with Benzyl Group A cold aqueous solution of Fmoc-asparagine-linked bifurcated disialooligosaccharide (20 mg) was passed through a column [φ0.5 cm×5 cm] of Dowex-50Wx8(H$^+$), and the eluate of aqueous solution was freeze-dried.

The Fmoc-asparagine-linked bifurcated disialooligosaccharide obtained was dissolved in cold water at 4° C., an aqueous solution of Cs$_2$CO$_3$ (2.5 mg/ml) was added to the solution to obtain an adjusted pH of 5 to 6, and the oligosaccharide solution was freeze-dried. The resulting sample of Fmoc-disialooligosaccharide was dissolved in dry DMF (1.3 ml), benzyl bromide (5.1 μl) was added to the solution, and the mixture was stirred at room temperature under an argon stream for 45 hours. After the completion of reaction was recognized by TLC, the reaction mixture was cooled to 0° C., and 10 ml of diethyl ether was added to the mixture to separate out the desired product. The product was filtered with filter paper. Distilled water was added to the remaining desired product, and a filtrate was obtained from the mixture and subsequently concentrated in a vacuum. The residue obtained was purified by an ODS column to obtain 18.2 mg (85% in yield) of the desired product, i.e., Fmoc-asparagine-linked disialooligosaccharide (12).

(12)

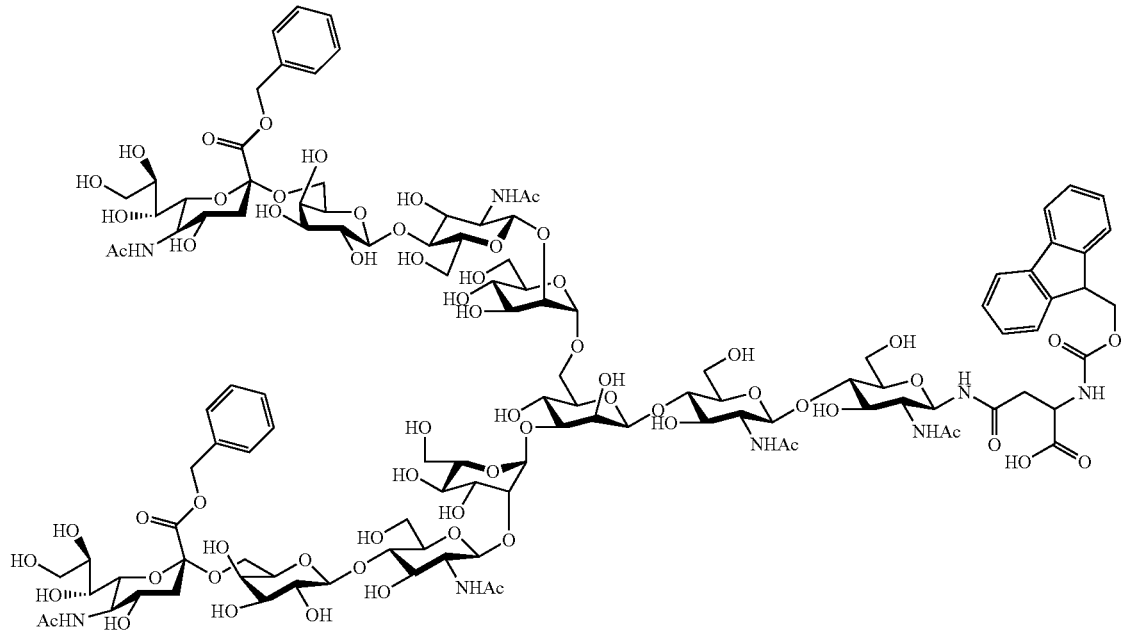

$^1$H-NMR (30° C.), 7.90 (d, 2H, Fmoc), 7.70 (d, 2H, Fmoc), 7.53-7.40 (m, 9H, Bn, Fmoc), 5.36 (d, 2H, J=11.6, Hz, CH$_2$), 5.30 (d, 2H, J=11.6 Hz, CH$_2$), 5.12 (s, 1H, Man4-H$_1$), 4.99 (d, 1H, J=9.7 Hz, GlcNAc1-H$_1$), 4.93 (s, 1H, Man4'-H$_1$), 4.75 (s, 1H, Man3-H$_1$), 4.57 (m, 3H, GlcNAc2-H$_1$, GlcNAc5, 5'-H$_1$), 4.32 (d, 2H, Gal6, 6'-H$_1$), 4.24 (d, 1H, Man3-H$_2$), 4.18 (d, 1H, Man4'-H$_2$), 4.10 (1H, d, Man4-H$_2$), 2.72 (bd, 1H, Asn-βCH), 2.67 (dd, 2H, NeuAc7, 7'-H$_{3eq}$), 2.51 (bdd, 1H, Asn-βCH), 2.06 (s, 3H, Ac), 2.03, 2.01 (each s, each 6H, Ac×2), 1.89 (s, 3H, Ac), 1.83 (2H, dd, J=12.2, 12.2 Hz, NeuAc7, 7'-H$_{3ax}$)

HRMS Calcd for C$_{117}$H$_{165}$N$_8$Na$_2$O$_{66}$[M+Na$^+$] 2783.9597, found 2783.9501

REFERENCE EXAMPLE 4

Asparagine-linked monosialooligosaccharide was prepared according to Japanese Patent Application No. 2001-185685.

REFERENCE EXAMPLE 5

Preparation of HOOC-Val-Leu-Leu-Ala-NH$_2$ (13)

I: Introduction into Resin

Wang resin (1.6 g) was placed into a solid-phase synthesis column, and the resin was fully washed with methylene chloride and then with methanol and dried. A 409.2 mg quantity (1.2 mmols) of Fmoc-Val and 121.5 mg (0.9 mmol) of 1-hydroxybenzotriazole hydrate (HOBt.H$_2$O) were dissolved in 4.5 ml of N,N-dimethylacetamide (DMA), 247.5 mg (1.2 mmols) of dicyclohexylcarbodiimide (DCC) was added to the solution, and the mixture was stirred at 0° C. for 15 minutes to obtain an amino acid solution. The resin was swollen with DMF. The amino acid solution was placed into the solid-phase synthesis column and stirred at room temperature for 17 hours. The resin was thereafter washed with methylene chloride, then with isopropanol and thereafter with methanol, and dried.

The dried resin was swollen with DMF in a column, about 10 ml of a 20% piperidine/DMF solution was thereafter added to the resin, followed by stirring at room temperature for 15 minutes to remove the protective Fmoc group and obtain resin-Val-NH$_2$. The resin was then washed with DMF and dried.

II: Lengthening Peptide Chain

The dried resin (resin-Val-NH$_2$) was swollen with DMF in a column, 318.6 mg (0.9 mmol) of Fmoc-Leu and 121.5 mg (0.9 mmol) of HOBt.H$_2$O were thereafter added to the resin, and DMF was further added in an amount to immerse the resin. With addition of 138.5 µl (0.9 mmol) of diisopropylcarbodiimide (DIPCDI), the mixture was stirred at room temperature for 2 hours. The resin was thereafter washed with DMF and dried.

The dried resin was swollen with DMF in a column, about 10 ml of a 20% piperidine/DMF solution was thereafter added to the resin, followed by stirring at room temperature for 15 minutes to remove the protective Fmoc group and obtain resin-Val-Leu-NH$_2$. The resin was then washed with DMF and dried.

The dried resin was swollen with DMF in a column, 318.6 mg (0.9 mmol) of Fmoc-Leu and 121.5 mg (0.9 mmol) of HOBt.H$_2$O were added to the resin, and DMF was further added in an amount to immerse the resin. With addition of 138.5 µl (0.9 mmol) of DIPCDI, the mixture was stirred at room temperature for 2 hours. The resin was thereafter washed with DMF and dried.

The dried resin was swollen with DMF in a column, about 10 ml of a 20% piperidine/DMF solution was thereafter added to the resin, followed by stirring at room temperature for 15 minutes to remove the protective Fmoc group and obtain resin-Val-Leu-Leu-NH$_2$. The resin was then washed with DMF and dried.

The dried resin was swollen with DMF in a column, 293.4 mg (0.9 mmol) of Fmoc-Ala and 121.5 mg (0.9 mmol) of HOBt.H$_2$O were added to the resin, and DMF was further added in an amount to immerse the resin. With addition of 138.5 µl (0.9 mmol) of DIPCDI, the mixture was stirred at room temperature for 2 hours. The resin was thereafter washed with DMF and dried.

The dried resin was swollen with DMF in a column, about 10 ml of a 20% piperidine/DMF solution was added to the resin, followed by stirring at room temperature for 15 minutes to obtain resin-Val-Leu-Leu-Ala-NH$_2$ by removing the protective Fmoc group. The resin was then washed with DMF and dried.

III: Separation from Resin

Preparation of HOOC-Val-Leu-Leu-Ala-NH$_2$

A 5% aqueous solution of TFA was added to the dried resin, and the mixture was stirred at room temperature for 3 hours. The solution was thereafter transferred to an egg-shaped flask, and diethyl ether was added to the solution with the flask placed in ice to precipitate the desired product, followed by filtration.

$^1$H-NMR (30° C.) 8.56 (1H, d, J=6.5 Hz, Leu-2NH), 8.42 (1H, d, J=7.4 Hz, Leu-1NH), 8.25 (1H, d, J=8.3 Hz, Val NH), 4.34 (1H, d, J=6.7 Hz, Val-α), 4.16 (1H, d, J=7.1 Hz, Ala-α), 2.27 (1H, ddd, Val-β), 1.69~1.58 (m, 11H, Leu-1, Leu-2), 1.59 (3H, d, J=7.2 Hz, Ala-β), 1.01~0.96 (m, 25H, Leu-1, Leu-2, Val)

(13)

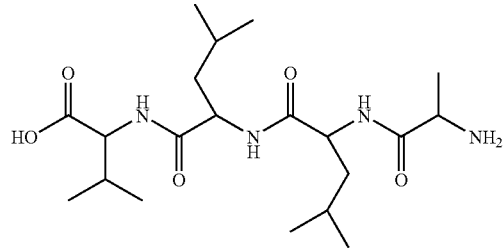

EXAMPLE 1

The resin (17 mg) in the form of dry resin-Val-Leu-Leu-Ala-NH$_2$ prepared in Reference Example 4 and before separation from the solid phase is placed into Eppen tube. A 35 mg quantity (14.8 µmols) of Dibenzyl-Fmoc-asparagine-linked disialooligosaccharide (12) obtained in Reference Example 3 and 0.64 mg (2.7 µmols) of O-(7-azabenzotriazol-1-yl)-1,1,3,3-tetramethyluronium hexafluorophosphonate (HATU) were added to the resin, and 150 µl of DMF was added. With addition of 0.31 µl of diisopropylethylamine (DIPEA), the mixture was stirred at room temperature for 24 hours. The resulting mixture was thereafter washed with DMF and dried.

The dried resin was swollen with DMF in an Eppen tube, about 1 ml of a 20% piperidine/DMF solution was thereafter added to the resin, followed by stirring at room temperature for 15 minutes to remove the protective Fmoc group and obtain resin-Val-Leu-Leu-Ala-Asn(oligo)-NH$_2$. The resin was then washed with DMF and dried. Asn(oligo) mentioned stands for dibenzyl-asparagine-linked disialooligosaccharide obtained by removing the Fmoc group from the Dibenzyl-Fmoc-asparagine-linked disialooligosaccharide (12) obtained in Reference Example 3.
(Separation from Solid Phase)
Preparation of HOOC-Val-Leu-Leu-Ala-Asn(oligo)-NH$_2$ An aqueous solution (95%) of trifluoroacetic acid (TFA) was added to the above dried resin, followed by stirring at room temperature for 3 hours. The solution was thereafter transferred to an Eppen tube, diethyl ether was added to the solution with the tube placed in ice to precipitate the desired product. The precipitate was dissolved in 0.1% aqueous solution of TFA, and the solution was purified by a reverse phase column chromatography. (YMC-Pack ODS-A 250×3.0 mm, flow rate 0.45 ml/min, developing solvent A: 0.1% TFA aqueous solution, B: 0.1% TFA acetonitrile:water=90:10, gradient only A 10 min, A100%→B100% 30 min).

The structure of Asn(oligo) is shown below.

An 80 mg quantity (180 μmols) of Fmoc-Ser(Bzl)-OH and 19 mg (135 μmols) of HOBt.H$_2$O were dissolved in 10 ml of DMF, 37 mg (180 μmols) of DCC was added to the solution, and the mixture was stirred at 0° C. for 15 minutes to obtain an amino acid solution. A resin was swollen with DMF. The amino acid solution was placed into a solid-phase synthesis column, followed by stirring at room temperature for 17 hours. The resin was thereafter washed with methylene chloride, then with isopropanol and thereafter with methanol, and dried.

The dried resin was swollen with DMF in a column, about 2.0 ml of a 20% piperidine/DMF solution was thereafter added to the resin, followed by stirring at room temperature for 15 minutes to remove the protective Fmoc group and obtain resin-Ser-NH$_2$. The resin was then washed with isopropanol and DMF and dried.

(14)

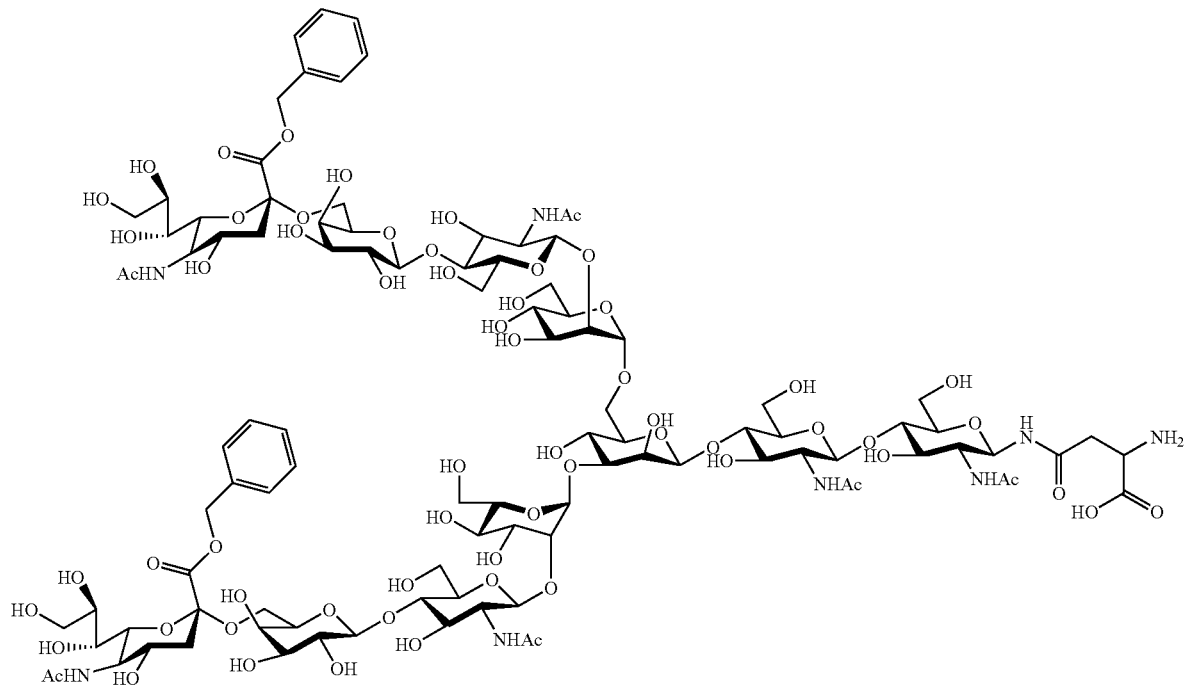

50

$^1$H-NMR (30° C.) 7.59~7.55 (m, 10H, Bn), 5.45 (4H, dd, Bn-CH$_2$×2), 5.23 (1H, s, Man4-H$_1$), 5.15 (1H, d, GlcNAc1-H$_1$), 5.03 (1H, s, Man4'-H$_1$), 4.87 (1H, s, Man3-H$_1$), 4.67 (3H, d, GlcNAc2-H$_1$, GlcNAc5, 5'-H$_1$), 4.42 (2H, d, Gal6, 6'-H$_1$), 4.34 (1H, d, Man3-H$_2$), 4.28 (1H, d, Man4'-H$_2$), 4.20 (1H, d, Man4-H$_2$), 2.82 (2H, dd, J=6.68 Hz, NeuAc7, 7'-H$_{3eq}$), 2.65 (1H, dd, J=16.69 Hz, 6.83 Hz, Asn-βCH), 2.13 (18H, s×6, -Ac), 1.94 (2H, dd, J=12.24 Hz, NeuAc7, 7'-H$_{3ax}$), 1.41~1.26 (m, 25H, Leu-1, Leu-2, Val)

EXAMPLE 2

Preparation of HOOC-Ser-Ser-Asn(oligo)-NH$_2$

I: Introduction into Resin

PEGA resin (50 mg) was placed into a solid phase synthesis column and thoroughly washed with methylene chloride and then with methanol and dried.

II: Lengthening Peptide Chain

The dried resin was swollen with DMF in a column, 40.0 mg (89.8 μmols) of Fmoc-Ser(Bzl)-OH and 12 mg (89.8 μmols) of HOBt.H$_2$O were thereafter added to the resin, and 2.0 ml of DMF was further added. With addition of 14 μl (89.8 μmols) of DIPCDI, the mixture was stirred at room temperature for 2 hours. The resin was thereafter washed with DMF and dried.

The dried resin was swollen with DMF in a column, about 2.0 ml of a 20% piperidine/DMF solution was thereafter added to the resin, followed by stirring at room temperature for 15 minutes to remove the protective Fmoc group and obtain resin-Ser-Ser-NH$_2$. The resin was then washed with isopropanol and DMF and dried.

The dried resin was swollen with dimethyl sulfoxide (DMSO) in a column, 13.5 mg (5.7 μmols) of Dibenzyl-Fmoc-asparagine-linked disialooligosaccharide (12)

obtained in Reference Example 3, as dissolved in DMF, was transferred to the column. To the mixture were added 1.6 mg (6.8 µmols) of HATU and 0.83 µl of DIPEA, and the resulting mixture was stirred at room temperature for 24 hours. The resin was thereafter washed with isopropanol and DMF and dried.

The dried resin was swollen in an Eppen tube, about 1 ml of a 20% piperidine/DMF solution was thereafter added to the resin, followed by stirring at room temperature for 15 minutes to remove the protective Fmoc group and obtain resin-Val-Ser-Ser-Asn(oligo)-$NH_2$. The resin was then washed with DMF and dried. The above Asn(oligo) was the same as that in Example 1.

III: Separation from Solid Phase

A 95% TFA aqueous solution was added to the dried resin, followed by stirring at room temperature for 3 hours. The reaction mixture was purified by reverse phase column chromatography. (YMC-Pack ODS-A 250×3.0 mm, flow rate 0.35 ml/min, developing solvents A: 0.1% TFA aqueous solution, B: 0.1% TFA acetonitrile:water=90:10, gradient A 100%→B 100% 120 min).

$^1$H-NMR (30° C.) 7.60~7.45 (m, 20H, Bn), 5.35 (4H, dd, J=11.8 Hz, Bn-$CH_2$—), 5.21 (1H, s, Man4-$H_1$), 5.13 (1H, d, J=9.2 Hz, GlcNAc1-$H_1$), 5.03 (1H, s, Man4'-$H_1$), 4.34 (1H, d, Man3-$H_2$), 4.28 (1H, d, Man4'-$H_2$), 4.20 (1H, d, Man4-$H_2$), 2.82 (2H, dd, J=6.68 Hz, NeuAc7, 7'-$H_{3eq}$), 2.13 (18H, s×6, -Ac), 1.93 (2H, dd, J=12.24 Hz, NeuAc7, 7'-$H_{3ax}$)

EXAMPLE 3

Preparation of HOOC-Ser-Ser-Asn(disialooligo)-Val-Leu-Leu-Ala-$NH_2$

Asn(disialooligo) in the desired glycopeptide mentioned above means a disialooligoasparagine having sialic acid not protected with benzyl group.

Into a solid-phase synthesis column was placed 50 mg of HMPA-PEGA resin, which was thoroughly washed with $CH_2Cl_2$ and DMF.

Fmoc-Ser(OtBu)-OH, 1-mesitylenesulfonyl-3-nitro-1,2,4-triazole (MSNT) and N-methylimidazole were dissolved in $CH_2Cl_2$, and the solution was stirred for 5 minutes and thereafter placed into the solid-phase synthesis column containing the resin, followed by stirring at room temperature for 3 hours. The resin was thereafter washed with methylene chloride, isopropanol and DMF and dried. The unreacted amino ? group on the solid phase was thereafter acetylated using a 20%-DMF solution of acetic anhydride for 20 minutes for capping. The resin was washed with DMF and stirred along with a 20% piperidine/DMF solution for 20 minutes to remove the protective Fmoc group, whereby resin-Ser-$NH_2$ was obtained. The product was washed with DMF and dried.

Next, Fmoc-Ser(OtBu)-OH was used with $HOBt.H_2O$ and DIPCDI for condensation.

Subsequently, Dibenzyl-Fmoc-asparagine-linked disialooligosaccharide (12) obtained in Reference Example 3 was dissolved in a 1:1 solvent mixture of DMSO and DMF, and the solution, HATU and DIPEA were stirred at room temperature for 24 hours for condensation. The resulting resin was washed with DMF and thereafter stirred along with 10% acetic anhydride/2-propanol:methanol=: for 20 minutes for capping. The resin was washed with 2-propanol and DMF, and thereafter stirred along with 20% piperidine/DMF for 20 minutes to remove the protective Fmoc group. The resin was washed with DMF.

The resulting resin, and valine (Val), leucine (Leu), leucine (Leu) and alanine (Ala) were similarly subjected to condensation, followed by removal of the protective Fmoc group to obtain resin-Ser-Ser-Asn(dibenzyldisialooligo)-Val-Leu-Leu-Ala-$NH_2$. Asn(dibenzyldisialooligo) mentioned means a disialooligoasparagine having sialic acid protected with benzyl group.

Used as the amino acids of valine (Val), leucine (Leu), and alanine (Ala) were each Fmoc-AA-Opfp (AA=amino acid) wherein the carboxyl group was pfp-esterified, and 3,4-dihydro-4-oxo-1,2,3-benzotriazin-3-yl (Dhbt) was used for condensation. All condensation reactions were conducted in a DMF solution.

The resin resulting from condensation was thoroughly dried, and thereafter stirred along with a 95% aqueous solution of TFA at room temperature for 3 hours to cut off the resin. The resin was filtered off. The reaction mixture was concentrated in a vacuum at room temperature, thereafter dissolved in water and freeze-dried. The resulting product was dissolved in an aqueous solution of sodium hydroxide having a pH of 11 to hydrolyze the benzyl ester for the removal of benzyl group, followed by neutralization with acetic acid. The product was freeze-dried as it was, and purified by HPLC to obtain the desired product, i.e., HOOC-Ser-Ser-Asn(disialooligo)-Val-Leu-Leu-Ala-$NH_2$.

(YMC-Pack ODS-A 250×3.0 mm, developing solvents A: 0.1% TFA aqueous solution, B: 0.1% TFA acetonitrile:water=90:10, gradient A 100% 0.35 ml/min→B 100% 0.40 ml/min 90 min, flow rate 0.35 ml/min to 0.40 ml/min).

$^1$H-NMR (30° C.) δ 5.22 (s, 1H, Man4-H1), 5.11 (d, 1H, GlcNAc1-H1), 5.04 (s, 1H, Man4'-H1), 4.86 (1H, Asnα), 4.70 (bd, 3H, GlcNAc2, 5, 5'-H1), 4.62-4.57 (m, 2H, Serα× 2), 4.53 (d, 2H, Gal6, 6'-H1), 4.52-4.48 (m, 2H, Leuα×2), 4.34 (bs, 1H, Man3-H2), 4.28 (bs, 1H, Man-4-H2), 4.21-4.15 (m, 3H, Man4'-H2, Valα, Alaα), 2.98 (dd, 1H, Asnβ), 2.86 (dd, 1H, Asnβ), 2.75 (bdd, 2H, NeuAc7, 7'-H3eq), 2.16-2.10 (Ac×6, Valβ), 1.82 (dd, 2H, NeuAc7, 7, —H3ax), 1.76-1.68 (bd, 6H, Leuβ$CH_2$×2, LeuγCH×2), 1.60 (d, 3H, Alaβ$CH_3$), 1.03-0.97 (m, 18H, Leu-$CH_3$×4, Val-$CH_3$×2)

EXAMPLE 4

Preparation of HOOC-Ser-Ser-Asn(Disialooligo)-Val-Leu-Leu-Ala-Asn(asialooligo)-Val-Leu-Leu-Ala-$NH_2$ Asn(asialooligo) in the desired glycopeptide above is an asparagine-linked oligosaccharide shown below.

(15)

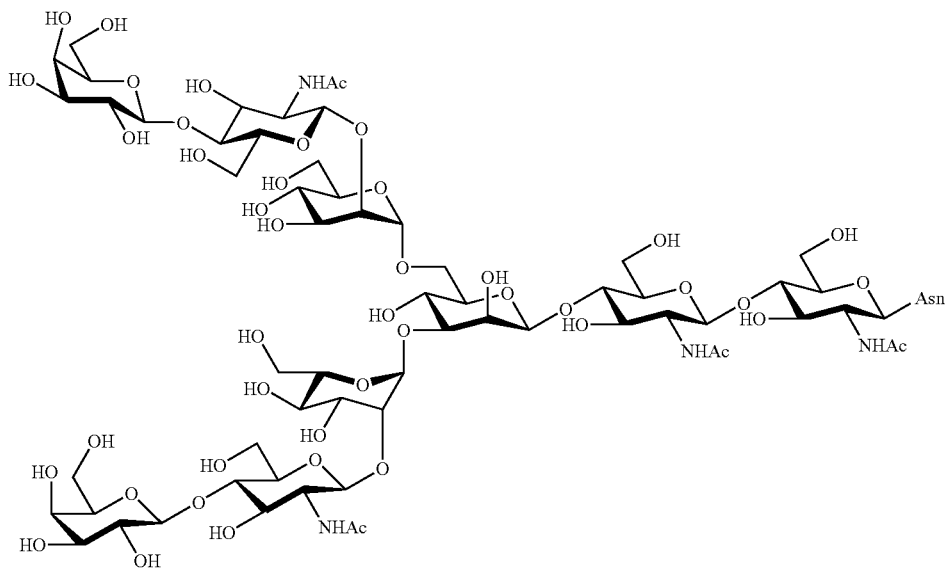

Resin-Ser-Ser-Asn(dibenzyldisialooligo)-Val-Leu-Leu-Ala-NH$_2$ before being separated from the solid phase, and Asn(asialooligo), valine (Val), leucine (Leu), leucine (Leu) and alanine (Ala), were subjected to condensation. The resulting peptide chain was cut off from the solid phase in the same manner as in Example 3, followed by the removal of the benzyl group, affording a glycopeptide in the form of HOOC-Ser-Ser-Asn(disialooligo)-Val-Leu-Leu-Ala-Asn(asialooligo)-Val-Leu-Leu-Ala-NH$_2$.

Used as the amino acids of valine (Val), leucine (Leu) and alanine (Ala) were each Fmoc-AA-Opfp (AA=amino acid) wherein the carboxyl group was pfp-esterified, and 3,4-dihydro-4-oxo-1,2,3-benzotriazin-3-yl (Dhbt) was used for condensation. All condensation reactions were conducted in a DMF solution. The resulting resin was stirred at room temperature for 20 minutes with addition of a 20% piperidine/DMF solution to remove the protective Fmoc group.

After the introduction of the amino acid (Val) to be positioned subsequent to the asparagine-liked oligosaccharide, a 20% acetic anhydride/2-propanlol:methanol=1:1 solution was used for capping the unreacted amino group of asparagine-linked oligosaccharide, and then the protective Fmoc group was removed. The resin was washed with isopropanol and DMF and dried. The condensation of Fmoc-asparagine-linked asialooligosaccharide was conducted in the same manner as the condensation of benzyl-Fmoc-asparagine-liked disialooligosaccharide of Example 3.

Shown below is data as to $^1$H-NMR (30° C.) of the glycopeptide obtained which is in the form of HOOC-Ser-Ser-Asn(disialooligo)-Val-Leu-Leu-Ala-Asn(asialooligo)-Val-Leu-Leu-Ala-NH$_2$. δ 5.22, 5.21 (each s, each 1H, Man4-H1, ManD-H1), 5.11 (d, 2H, GlcNAc1-H1, GlcNAcA-H1), 5.03, 5.01 (each s, each 1H, Man4'-H1, ManD'-H-1), 4.86 (2H, Asnα), 4.69-4.66 (GlcNAc2, B, 5, 5', E, E'-H1), 4.61-4.48 (Leuα×4, Serα×2, Gal6, 6', F, F'-H1), 4.33 (bs, 2H, Man3, C—H2), 4.28 (bs, 2H, Man4, D-H2), 4.20 (bs, 2H, Man4', D'-H2), 4.20-4.17 (Valα×2, Alaα×2), 3.00 (dd, 2H, Asnβ×2), 2.83 (dd, 2H, Asnβ×2), 2.76 (dd, 2H, NeuAc7, 7'-H3eq), 1.82 (dd, 2H, NeuAc7, 7'-H3ax), 2.16-2.10 (Ac×10, Valβ), 1.70-1.60 (m, Leuβ, γ), 1.60, 1.49 (each d, each 3H, Alaβ), 1.02-0.96 (m, 36H, Val-CH$_3$×4, Leu-CH$_3$×8)

REFERENCE EXAMPLE 6

The asparagine-linked oligosaccharide represented by Asn (asialooligo) was prepared according to Examples of Japanese Patent Application No. 2001-185685. NMR data as to the product is given below.

$^1$H-NMR (30° C.) δ 5.12 (s, 1H, Man4-H-1), 5.07 (d, 1H, J=9.7 Hz, GlcNAc1-H-1), 4.92 (s, 1H, Man4'-H-1), 4.76 (s, 1H, Man3-H-1), 4.62 (d, 1H, J=8.0 Hz, GlcNAc2-H-1), 4.58 (d, 2H, J=7.8 Hz, GlcNAc5, 5'-H-1), 4.47 (d, 2H, J=7.9 Hz, Gal6, 6'-H-1), 4.24 (bd, 1H, Man3-H-2), 4.19 (bdd, 1H, J=3.2 Hz, 1.4 Hz, Man4'-H-2), 4.12 (bdd, 1H, J=3.2 Hz, 1.4 Hz, Man4-H-2), 2.93 (dd, 1H, J=4.5 Hz, 17.0 Hz, Asn-βCH), 2.93 (dd, 1H, J=6.8 Hz, 17.0 Hz, Asn-βCH), 2.08 (s, 3H, Ac), 2.05 (s, 6H, Ac×2), 2.01 (s, 3H, Ac)

Also, Fmoc-asparagine-linked asialooligosaccharide was obtained in the same manner as in Reference Example 2. NMR data thereof is given below.

$^1$H-NMR (D$_2$O, 30° C.) δ 7.99 (2H, d, Fmoc), 7.79 (2H, d, Fmoc), 7.55 (4H, m, Fmoc), 5.12 (1H, s, Man4-H1), 5.06 (1H, d, GlcNAc1-H1), 4.93 (1H, s, Man4'-H1), 4.82 (1H, s, Man3-H1), 4.69 (1H, d, GlcNAc2-H1), 4.67 (2H, d, GlcNAc5, 5'-H1), 4.53 (2H, d, Gal6, 6'-H1), 4.34 (1H, d, Man3-H2), 4.27 (1H, d, Man4'-H2), 4.19 (1H, d, Man4-H2), 3.03 (1H, bdd, Asn-βCH), 3.00 (1H, bdd, Asn-βCH), 2.15 (12H, s×4, -Ac)

REFERENCE EXAMPLE 7

Preparation of Benzyl 3,6-O-pivaloyl-β-D-galactopyranoside (18)

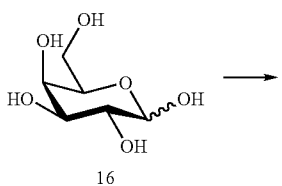

-continued

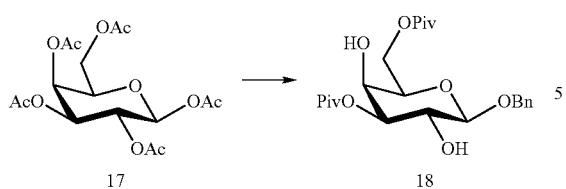

(1) Preparation of Compound (17)

Sodium acetate (5 g, 69 mmols) was dissolved in acetic anhydride (60 ml), the solution was heated, and D-galactose (16) (10 g, 55 mmols) was thereafter added in small portions to the solution. The mixture was reflux with heating for 2 hours, and the completion of reaction was thereafter recognized by TLC (toluene:ethyl acetate=5:1). The reaction mixture was returned to room temperature and then poured into 300 cc of ice water. The resulting precipitate was collected by filtration. The precipitate was dissolved in ethanol (14 ml) for recrystallization, giving 9.0 g of Compound (17) (41% in yield).

(2) Preparation of Compound (18)

Compound (17) (4.3 g, 11 mmols) was dissolved in methylene chloride (120 ml), and the solution was thereafter cooled to −20° C. under an argon stream. Subsequently, tin tetrachloride (3.1 g, 12 mmols) was added to the solution, the mixture was stirred for 20 minutes, benzyl alcohol (2.3 g, 22 mmols) was then added to the mixture, and the reaction temperature was returned to room temperature. After the completion of reaction was recognized by TLC (hexane:ethyl acetate=1:1), the reaction mixture was poured into a saturated aqueous solution of sodium hydrogencarbonate, followed by extraction with methylene chloride. The methylene chloride layer was dried over anhydrous magnesium sulfate, then filtered and concentrated in a vacuum. The residue was dried in a desiccator, thereafter dissolved in distilled methanol (80 ml), sodium methoxide (431 mg, 5.5 mmols) was added to the solution, and the mixture was stirred under an argon stream. After the completion of reaction was recognized by TLC (ethyl acetate:methanol:water=10:5:1), the reaction mixture was neutralized with a cation-exchange resin IR-120(+) to terminate the reaction. The resin was filtered off for removal, and the filtrate was concentrated in a vacuum. The residue was dried in a desiccator, thereafter dissolved in pyridine (44 ml), and the reaction mixture was cooled to 0° C. Pivaloyl chloride (4.6 g, 38.5 mmols) was added to the reaction mixture, and the mixture was returned to room temperature and stirred under an argon stream for 1 hour. After the completion of reaction was recognized by TLC (hexane:ethyl acetate=2:1), the reaction mixture was cooled to 0° C., and methanol was thereafter added to the mixture to terminate the reaction. The reaction mixture was concentrated as it was in a vacuum, the residue was then dissolved in ethyl acetate, the solution was washed with a saturated aqueous solution of sodium chloride and water, and dried over anhydrous magnesium sulfate to evaporate off the ethyl acetate. After the magnesium sulfate was removed by filtration, the filtrate was concentrated in a vacuum. The residue was purified by silica gel column chromatography (developing solvent: hexane:ethyl acetate=2:1), giving Compound (18) (2.8 g, yield 58%).

REFERENCE EXAMPLE 8

Preparation of Benzyl 2-O-chloroacetyl-4-deoxy-4-fluoro-3,6-di-O-pivaloyl-β-D-glucopyranoside (20)

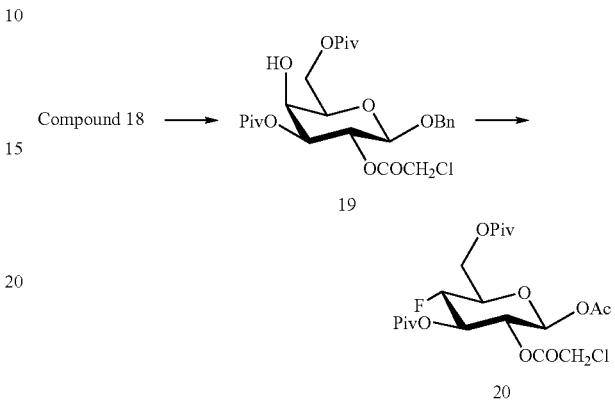

(1) Preparation of Benzyl 2-O-chloroacetyl-3,6-di-O-pivaloyl-β-D-galactopyranoside (19)

Compound 18 (200 mg, 0.455 mmols) was dissolved in dichloromethane (7.8 ml) and pyridine (1.3 ml), chloroacetic anhydride (155 mg, 0.91 mmol) was added to the solution, and the mixture was reacted with stirring at −15° C. under an argon stream for 15 minutes. After the completion of reaction was recognized, the chloroacetic anhydride was quenched with methanol (5 ml), and the reaction mixture was azeotropically boiled with toluene three times for concentration in vacuum. The residue was extracted with ethyl acetate, and the extract was washed with a saturated aqueous solution of sodium chloride. The organic layer was dried over anhydrous magnesium sulfate, followed by filtration and concentration. The residue was purified by silica gel column chromatography (ethyl acetate:hexane=1:4), giving Compound (19) (in an amount of 172 mg, 73.5% in yield).

$^1$H-NMR (400 MHz, CDCl$_3$) δ 7.37-7.29 (m, 5H, Ph), 5.39 (dd, 1H, $J_{1,2}$=8.0 Hz, $J_{2,3}$=10.4 Hz, H-2), 4.89 (dd, 1H, $J_{3,4}$=3.4 Hz, H-3), 4.89, 4.62 (2d, 2H, J=12.5 Hz, OCH$_2$Ph), 4.53 (d, 1H, H-1), 4.37 (dd, 1H, $J_{6a,6b}$=11.5 Hz, $J_{6a,5}$=6.0 Hz, H-6a), 4.32 (dd, 1H, $J_{6b,5}$=6.6 Hz, H-6b), 4.00 (m, 1H, H-4), 3.92 (s, 2H, COCH$_2$Cl), 3.75 (dd, 1H, H-5), 1.23, 1.19 [2s, 18H, COC(CH$_3$)$_3$]

$^{13}$C-NMR (400 MHz, CDCl$_3$) δ 178.33, 177.57, 165.92, (C=O), 136.66, 128.48, 128.07, 127.89 (Ph), 99.16 (C-1), 72.82 (C-3), 72.35 (C-5), 70.92 (C-2), 70.49 (OCH$_2$Ph), 67.29 (C-4), 62.30 (C-6), 40.40 (COCH$_2$Cl), 38.95, 38.80 [COC(CH$_3$)$_3$], 27.14, 26.98 [COC(CH$_3$)$_3$]

$^1$H-NMR and $^{13}$C-NMR were measured using Bruker's AVANCE 400 (mentioned as 400 MHz). When the solvent was deuteriochloroform, trimethylsilane was used as internal standard. When other deuteriated solvents were used, the peak of the solvent was used as a reference. Chemical shifts were indicated by δ (ppm), and the coupling constants by J (Hz). Used for silica gel chromatography were Merck Silicage 160, 70-230 mesh or 230-400 mesh, and spherical silica gel which was Silica Gel 60 (Spherical), product of Kanto Chemical Co., Ltd. Used for detecting reactions (for TLC)

was DC-Platten Kieselgel 60 F254 (Artl, 05715), product of E. Merk. The columns used for high performance chromatography (HPLC) were COSMOSIL 5C$_{18}$-AR Packed Column [ϕ4.6×150 mm], product of Nakaraitesuku Co., Ltd. The spectrophotofluorometer used was FP-210 Spectrofluorometer, product of JASCO.

(2) Preparation of Benzyl 2-O-chloroacetyl-4-deoxy-4-fluoro-3,6-di-O-pivaloyl-β-D-glucopyranoside (20)

Compound (19) (300 mg, 0.583 mmol) was dissolved in dichloromethane (5.8 ml), and diethylaminosulfatrifluoride (DAST) was added to the solution with stirring under an argon stream at −15° C. The mixture was returned to room temperature 10 minutes after the addition of DAST and reacted for 1 hour. Disappearance of the material was confirmed by TLC, the DAST was quenched with methanol (3 ml), and the reaction mixture was concentrated in a vacuum. The residue was purified by silica gel chromatography (ethyl acetate:hexane=1:6), giving Compound (20) (in an amount of 211 mg, yield 70%).

$^{1}$H-NMR (400 MHz, CDCl$_{3}$) δ 7.37-7.27 (m, 5H, Ph), 5.31 (ddd, 1H, J$_{3, F}$=14.3 Hz, J$_{3, 4}$=9.69 Hz, J$_{2, 3}$=9.63 Hz, H-3), 5.04 (dd, 1H, J$_{1, 2}$=7.93 Hz, H-2), 4.86 (d, 1H, J=12.2 Hz, OCH$_{2}$Ph), 4.60 (d, 1H, H-1), 4.59 (d, 1H, OCH$_{2}$Ph), 4.44 (ddd, 1H, J$_{4, 5}$=9.04 Hz, J$_{4, F}$=50.6 Hz, H-4), 4.43 (ddd, 1H, J$_{6a, 6b}$=12.1 Hz, J$_{6a, 5}$=2.41 Hz, J$_{6a, F}$=2.23 Hz, H-6a), 4.24 (ddd, 1H, J$_{6b, 5}$=5.67 Hz, J$_{6b, F}$=1.28 Hz, H-6b), 3.93 (s, 2H, OCOCH$_{2}$Cl), 3.75 (m, 1H, H-5), 1.25, 1.18 [2s, 18H, OCOC(CH$_{3}$)$_{3}$]
$^{13}$C-NMR (400 MHz, CDCl$_{3}$) δ 177.94, 117.43, 165.88 (C=O), 136.34, 128.55, 138.23, 127.92 (Ph), 98.68 (C-1), 87.35 (d, J$_{4, F}$=188.62 Hz, C-4), 72.65 (d, J$_{2, F}$=7.96 Hz, C-2), 72.05 (d, J$_{3, F}$=20.02 Hz, C-3), 71.49 (d, J$_{5, F}$=23.09 Hz, C-5), 70.80 (OCH$_{2}$Ph), 62.12 (C-6), 40.30 (OCOCH$_{2}$Cl), 38.87 [OCOC(CH$_{3}$)$_{3}$], 27.17, 26.92 [OCOC(CH$_{3}$)$_{3}$]

REFERENCE EXAMPLE 9

Preparation of Benzyl 2-azido-2,4-dideoxy-4-fluoro-3,6-di-O-pivaloyl-β-D-mannopyranoside (22)

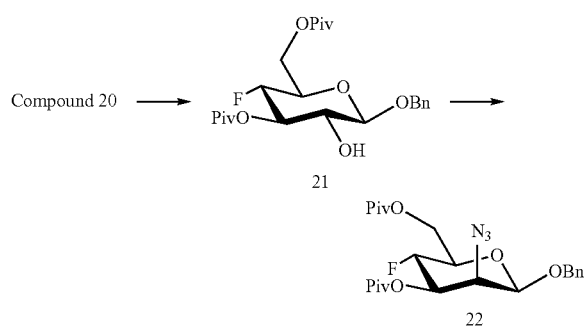

(1) Preparation of Benzyl 4-deoxy-4-fluoro-3,6-di-O-pivaloyl-β-D-glucopyranoside (21)

Compound (20) (625 mg, 1.21 mmols) was dissolved in methanol (24.2 ml), and sodium methoxide (13.1 mg, 0.6 mmol) was added to the solution with stirring under an argon stream at −15° C. Disappearance of the material was confirmed by TLC 30 minutes later, and the reaction mixture was neutralized (pH 6-7) with a cation-exchange resin IR-120(+).

After the resin was filtered off, the filtrate was concentrated in a vacuum. The residue was purified by silica gel chromatography (ethyl acetate:hexane=1:4), giving Compound (21) (in an amount of 395 mg, yield 74%).

$^{1}$H-NMR (400 MHz, CDCl$_{3}$) δ 7.38-7.29 (m, 5H, Ph), 5.18 (ddd, 1H, J$_{3, F}$=14.8 Hz, J$_{3, 4}$=9.51 Hz, J$_{2, 3}$=8.99 Hz, H-3), 4.90 (d, 1H, J=11.7, OCH$_{2}$Ph), 4.63 (d, 1H, OCH$_{2}$Ph), 4.47 (ddd, 1H, J$_{5, 6a}$=2.43 Hz, J$_{6a, F}$=2.2 Hz, H-6a), 4.47 (d, 1H, J$_{1, 2}$=7.7 Hz, H-1), 4.38 (ddd, 1H, J$_{4, 5}$=8.96 Hz, J$_{3, 4}$=9.67 Hz, J$_{4, F}$=50.8 Hz, H-4), 4.23 (ddd, 1H, J$_{6a, 6b}$=12.0 Hz, J$_{6b, 5}$=6.05 Hz, J$_{6b, F}$=1.26 Hz, H-6b), 3.75 (m, 1H, H-5), 3.54 (m, 1H, J$_{2, OH}$=2.70 Hz, H-2), 1.27, 1.26 [2s, 18H, OCOC(CH$_{3}$)$_{3}$]
$^{13}$C-NMR (400 MHz, CDCl$_{3}$) δ 178.17, 177.94 (C=O), 136.54, 128.54, 128.17, 128.12 (Ph), 101.31 (C-1), 87.45 (d, J$_{4, F}$=187.39 Hz, C-4), 74.17 (d, J$_{3, F}$=18.88 Hz, C-3), 72.45 (d, J$_{2, F}$=7.56 Hz, C-2), 71.45 (d, J$_{5, F}$=23.26 Hz, C-5), 71.09 (OCH$_{2}$Ph), 62.44 (C-6), 38.90, 38.85 [OCOC(CH$_{3}$)$_{3}$], 27.14, 26.99 [OCOC(CH$_{3}$)$_{3}$]

(2) Preparation of Benzyl 2-azido-2,4-dideoxy-4-fluoro-3,6-di-O-pivaloyl-β-D-mannopyranoside (22)

To a solution of pyridine (22.2 µl, 0.274 mmol) in dichloromethane (370 µl) was added dropwise trifluoromethanesulfonic anhydride (46 µl, 0.274 mmol) at 0° C., and 15 minutes later, a solution of Compound (21) in dichloromethane (1 ml) was added dropwise to the mixture at 0° C. Disappearance of the material was confirmed by TLC, and the reaction mixture was diluted with dichloromethane. The organic layer was washed with a saturated aqueous solution of sodium hydrogencarbonate, saturated sodium chloride aqueous solution and water, dried over anhydrous magnesium sulfate and thereafter concentrated. The residue was further dried by a vacuum pump, and then dissolved in benzene (1 ml). Sodium azide (13 mg, 0.206 mmol) and tetraammonium chloride (57 mg, 0.206 mmol) were added to the solution under an argon stream at room temperature, and the mixture was reacted at 40° C. The disappearance of the material was confirmed by TLC, and the reaction mixture was thereafter concentrated in a vacuum. The residue was subjected to extraction with ethyl acetate, and the extract was washed with a saturated sodium chloride aqueous solution and water, dried over anhydrous magnesium sulfate and thereafter concentrated. The residue was purified by silica gel column chromatography (ethyl acetatae:hexane=1:4), affording Compound (22) (in an amount of 30.4 mg, 95% in yield).

$^{1}$H-NMR (400 MHz, CDCl$_{3}$) δ 7.39-7.32 (m, 5H, Ph), 4.99 (ddd, 1H, J$_{3, F}$=13.18 Hz, J$_{3, 4}$=9.27 Hz, J$_{2, 3}$=3.87 Hz, H-3), 4.93 (d, 1H, J=12.07 Hz, OCH$_{2}$Ph), 4.67 (d, 1H, J$_{1, 2}$=1.18 Hz, H-1), 4.63 (d, 1H, OCH$_{2}$Ph), 4.51 (ddd, 1H, J$_{6a, 6b}$=11.95 Hz, J$_{6a, 5}$=2.54 Hz, J$_{6a, F}$=2.08 Hz, H-6a), 4.23 (ddd, 1H, J$_{6b, 5}$=6.14 Hz, J$_{6b, F}$=1.14 Hz, H-6b), 4.08 (m, 1H, H-2), 3.64 (m, 1H, H-5), 1.26 [2s, 18H, OCOC(CH$_{3}$)$_{3}$]
$^{13}$C-NMR (400 MHz, CDCl$_{3}$) δ 178.01, 177.68 (C=O), 136.06, 128.63, 128.31, 128.14 (Ph), 97.25 (C-1), 85.51 (d, J$_{4, F}$=183.97, C-4), 72.01 (d, J$_{5, F}$=23.89, C-5), 71.73 (d, J$_{3, F}$=18.98, C-3) 70.57 (OCH$_{2}$Ph), 62.42 (C-2, C-6), 39.08, 38.90 [OCOC(CH$_{3}$)$_{3}$], 27.18, 26.95 [OCOC(CH$_{3}$)$_{3}$]

REFERENCE EXAMPLE 10

Preparation of
N-Acetyl-4-deoxy-4-fluoro-D-mannosamine 24

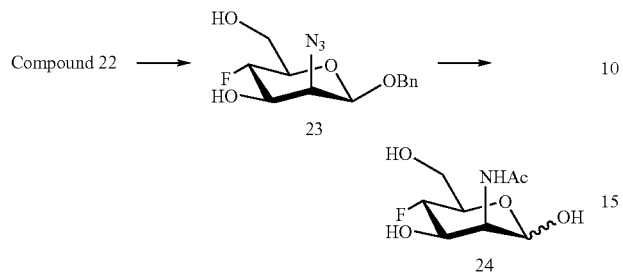

(1) Preparation of Benzyl 2-azido-2,4-dideoxy-4-fluoro-β-D-mannopyranoside (23)

Compound (22) (180 mg, 0.387 mmol) was dissolved in methanol (8 ml), sodium methoxide (922 mg, 9.67 mmols) was added to the solution, and the mixture was reacted with stirring at 40° C. TLC revealed 4.5 hours later that the reaction mixture collected into a spot, and the mixture was neutralized with a cation-exchange resin IR-120(+), followed by filtration and concentration. The residue was purified by silica gel column chromatography (ethyl acetate:hexane=1:1), giving Compound (23) (in an amount of 105.3 mg, 91.6% in yield).

$^1$H-NMR (400 MHz, CDCl$_3$) δ 7.40-7.31 (m, 5H, Ph), 4.96 (d, 1H, J=12.13 Hz, OCH$_2$Ph), 4.71 (d, 1H, J$_{1,2}$=1.33 Hz, H-1), 4.69 (d, 1H, OCH$_2$Ph), 4.49 (ddd, 1H, J$_{4,F}$=51.06 Hz, J$_{4,5}$=9.19 Hz, J$_{3,4}$=9.20 Hz, H-4), 4.02 (m, 1H, H-2), 3.93 (dddd, 1H, J$_{6a,6b}$=12.19 Hz, J$_{6a,5}$=2.31 Hz, J$_{6a,F}$=2.32 Hz, J$_{6a,OH}$=6.20 Hz, H-6a), 3.89-3.77 (m, 2H, H-3, H-6b), 3.39 (m, 1H, H-5)

$^{13}$C-NMR (400 MHz, CDCl$_3$) δ 136.39, 128.62, 128.24, 127.83 (Ph), 98.63 (C-1), 88.19 (d, J$_{4,F}$=178.91 Hz, C-4), 73.95 (d, J$_{5,F}$=25.48 Hz, C-5), 71.18 (OCH$_2$Ph), 71.16 (d, J$_{3,F}$=19.69 Hz, C-3), 64.48 (d, J$_{2,F}$=8.42 Hz, C-2), 61.39 (C-6)

(2) Preparation of N-Acetyl-4-deoxy-4-fluoro-D-mannosamine (24)

Compound (23) (105 mg, 0.353 mmol) was dissolved in methanol (7 ml), acetic anhydride (333 μl, 3.53 mols) was added to the solution, a catalytic amount of 10% Pd/C was thereafter added to the mixture, and the resulting mixture was stirred at room temperature after replacing the atmosphere in the reactor with hydrogen. TLC indicated disappearance of the material 2 hours later, followed by filtration with activated carbon and concentration. The residue was purified by silica gel column chromatography (ethyl acetate:methanol=5:1), giving Compound (24) (in an amount of 57 mg, 72% in yield).

$^1$H-NMR (400 MHz, D$_2$O) δ 5.23 (dd, 1H, J$_{1,2}$=2.69 Hz, J$_{1,F}$=1.44 Hz, H-1-α), 4.65 (ddd, 1H, J$_{4,F}$=50.94 Hz, J$_{3,4}$=9.06 Hz, J$_{4,5}$=9.58 Hz, H-4-α), 4.47 (m, 1H, H-2-α), 4.43 (ddd, 1H, J$_{3,F}$=14.28 Hz, J$_{2,3}$=4.9 Hz, H-3-α), 4.16 (m, 1H, H-5-α), 3.95 (m, 2H, H-6a-α, H-6b-α), 2.14 (s, 3H, NHCOCH$_3$-α)

$^{13}$C-NMR (400 MHz, D$_2$O) δ 175.27 (C=O-α), 93.46 (C-1-α), 88.30 (d, J$_{4,F}$=177.00 Hz, C-4-α), 69.91 (d, J$_{5,F}$=24.41 Hz, C-5-α), 67.60 (d, J$_{3,F}$=18.74 Hz, C-3-α), 60.36 (C-6), 54.12 (d, J$_{2,F}$=8.68 Hz, C-2-α), 22.31 (NHCOCH$_3$-α)

REFERENCE EXAMPLE 11

Preparation of 5-Acetamido-3,5,7-trideoxy-7-fluoro-D-glycero-β-D-galacto-2-nonulopyranosidonic acid (25)

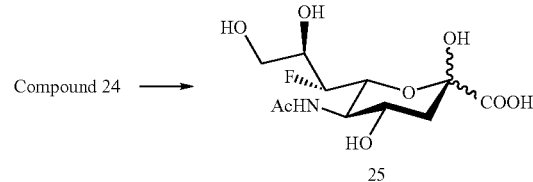

Compound (24) (50 mg, 0.224 mmol), sodium piruvate (123 mg, 1.12 mmols) and bovine serum albumin (5 mg) were dissolved in a sodium phosphate buffer solution (100 mM, pH 7.5, 3.4 ml), and aldolase sialate was thereafter added to the solution to start a reaction at room temperature. The reaction mixture was freeze-dried 24 hours later. The product was dissolved in a small amount of water and applied to an anion-exchange resin column (AG 1-X8, 200-400 mesh, formate form). After passing 300 ml of water through the column, the desired product was eluted with 1M formic acid, and the eluate was concentrated in a vacuum. The residue was purified by a gel filtration column (Sephadex G-15, water), giving Compound (25) (in an amount of 40 mg, 58.9% in yield).

$^1$H-NMR (400 MHz, D$_2$O) δ 4.61 (dd, 1H, J$_{7,8}$=8.97 Hz, J$_{7,F}$=45.56 Hz, H-7), 4.18 (dd, 1H, J$_{5,6}$=10.63 Hz, J$_{6,F}$=29.86 Hz, H-6), 4.15 (m, 1H, H-4), 4.07 (m, 1H, H-8), 4.02 (dd, 1H, J$_{4,5}$=100.10 Hz, H-5), 3.90 (ddd, 1H, J$_{9a9b}$=12.18 Hz, J$_{9a,8}$=2.77 Hz, J$_{9a,F}$=2.86 Hz, H-9a), 3.76 (ddd, 1H, J$_{9b,8}$=5.33 Hz, J$_{9b,F}$=2.06 Hz, H-9b), 2.40 (dd, 1H, J$_{3eq,3ax}$=13.00, J$_{3eq,4}$=4.88 Hz, H-3 eq), 2.15 (s, 3H, OCOCH$_3$), 2.00 (dd, 1H, J$_{3ax,4}$=11.70 Hz, H-3ax)

$^{13}$C-NMR (400 MHz, D$_2$O) δ 175.17, 173.68 (C=O), 96.01 (C-1), 89.12 (d, J$_{7,F}$=179.23 Hz, C-7), 69.67 (d, J$_{6,F}$=17.41 Hz, C-6), 68.31 (d, J$_{8,F}$=26.50 Hz, C-8), 67.26 (C-4), 62.70 (C-6), 52.17 (C-5), 39.19 (C-3), 22.61 (NHCOCH$_3$

REFERENCE EXAMPLE 12

Preparation of 5-Acetamido-3,5,8-trideoxy-8-fluoro-D-glycero-β-D-galacto-2-nonulopyranosidonic acid (27)

5-Acetamido-3,5,8-trideoxy-8-fluoro-D-glycero-β-D-galacto-2-nonulopyranosidonic acid (27) was prepared from Sialic acid (26) according to the scheme given below.

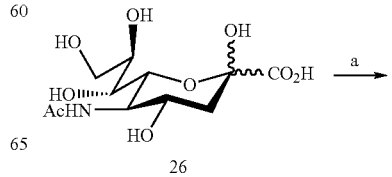

-continued

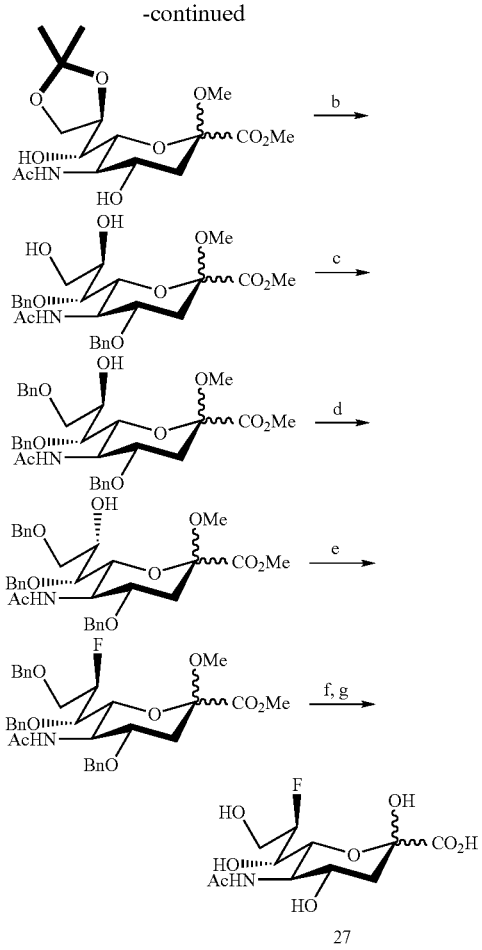

27

(a) (1) Dowex 50-X8, dist. MeOH, (2) Acetone dimethyl acetal, Camphor sulfonic acid, MeCN, y=73%;
(b) (1) BaO, Ba(OH)$_2$, BnBr, DMF, (2) CH$_2$N$_2$, (3) 60% AcOH, y=61.8%;
(c) (1) Dibutyltin oxide, toluene:MeOH=5:1, (2) tetra-n-butyl ammonium bromide, BnBr, toluene, y=74.3%;
(d) (1) DMSO, Oxalyl chloride, TEA, CH$_2$Cl$_2$, (2) BH$_3$NH$_3$, MeOH, y=73.2%;
(e) DAST, CH$_2$Cl$_2$, y=29.8%;
(f) Pd/C, AcOH, y=74.2%;
(g) (1) 0.3N NaOH, (2) Amberlyst 15H(+), 0.016N HCl, y=72.6%

(a) (1) Sialic acid (26) (1.02 g, 3.31 mmols) was dissolved in distilled methanol (150 ml), a cation-exchange resin, DOWex 50W-X8, (2.0 g) was added to the solution and the mixture was refluxed with heating for 24 hours for reaction. The end point of the reaction was confirmed by subjecting a portion of the reaction mixture to NMR spectroscopy. The reaction mixture was filtered, and methanol (100 ml) was added again to the resin, followed by stirring for 1 hour to collect the compound adsorbed by the resin. The resulting solution was filtered against, and the filtrate was combined with the filtrate obtained first, and the combined filtrate was concentrated in a vacuum to obtain a compound.

(2) The compound (5.05 g, 14.97 mmols) obtained above was dissolved in distilled acetone, and camphorsulfonic acid (498 mg, 2.14 mmols) was added to the solution with stirring under an argon stream at room temperature. Acetone dimethyl acetal (2.75 ml, 22.36 mmols) was thereafter added dropwise in small portions to the mixture to effect a reaction for 30 minutes. After the completion of reaction was confirmed, the reaction was terminated by the addition of triethylamine (2 ml), and the reaction mixture was concentrated in a vacuum. The residue was purified by silica gel column chromatography (ethyl acetate:methanol=20:1) to obtain acetonide derivative (α:β=1:10, yield 5.29 g).

(b) (1) The acetonide derivative (3.2 g, 8.48 mmols) obtained above was dissolved in N,N-dimethylformamide (43 ml), and barium oxide (9.3 g, 60.65 mmols) and barium hydroxide octahydrate (2.4 g, 7.61 mmols) were added to the solution. Subsequently, the mixture was stirred at room temperature, with benzyl bromide (10 ml, 84.1 mmols) added thereto. After the disappearance of the material was confirmed by TLC, the reaction mixture was diluted with dichloromethane and washed with a 1% formic acid aqueous solution and water, and the organic layer was dried over anhydrous magnesium sulfate. The magnesium sulfate was filtered off, and the organic layer was concentrated in a vacuum.

(2) The residue was dissolved in a solvent mixture of ethanol (25 ml) and benzene (50 ml), and a solution of diazomethane (42.5 mmols) in ether was added to the solution. The diazomethane used was produced by adding p-toluenesulfonyl-N-nitrous amide to a mixture solution of ether and ethanol, and adding a 50% & potassium hydroxide dropwise to the mixture. After the addition of the diazomethane, the mixture was reacted at room temperature for 10 minutes. After the disappearance of the material was confirmed by TLC, an excess of diazomethane was quenched with acetic acid (12 ml), followed directly by concentration in a vacuum.

(3) Subsequently, the residue was dissolved in a 60% aqueous solution of acetic acid, followed by a reaction at 60° C. for 12 hours. After the disappearance of the material was confirmed by TLC, the reaction mixture was concentrated in a vacuum. The residue was purified by silica gel column chromatography (ethyl acetate:methanol=15:1) to obtain a compound (α:β=1:24, yield 2.7 g).

(c) (1) The compound (1.08 g, 2.08 mmols) was dissolved in toluene (30 ml) and methanol (6.5 ml), dibutyl tin oxide (780 mg, 3.48 mmols) was added to the solution, and the mixture was reacted at 85° C. for 2 hours. The reaction mixture was thereafter concentrated in a vacuum, and the residue was azeotropically boiled with thoroughly dehydrated toluene three times.

(2) The residue was dissolved in toluene (24 ml) again, tetrabutylammonium bromide (1.00 g, 3.48 mmols) and benzyl bromide (977 ml, 10.4 mmols) were added to the solution, and the mixture was reacted at 80° C. for four hours. After the disappearance of the material was confirmed by TLC, the reaction mixture was returned to room temperature and concentrated in a vacuum. The residue was purified by silica gel column chromatography (ethyl acetate:hexane=4:1) to obtain a 4,7,9-benzyl compound (α:β=1:10, yield 1.15 g).

(d) (1) Oxalyl chloride (1.82 g, 14.3 mmols) was added to dichloromethane (13 ml), and the mixture was cooled to −78° C. A mixture solution of dimethyl sulfoxide (1.3 ml, 17.9 mmols) and dichloromethane (5 ml) was added to the mixture 15 minutes later, followed by stirring at −78° C. again. A solution of the 4,7,9-benzyl compound (2.18 mg, 3.59 mmols) obtained above in dichloromethane (18 ml) was slowly added to the resulting mixture 20 minutes later. The mixture was stirred at −78° C. for 20 minutes, triethylamine (4.00 ml, 28.7 mmols) was thereafter added to the mixture, followed by stirring for 10 minutes, and the reaction temperature was returned to room temperature. The appearance of the material was confirmed by TLC, the reaction mixture was then diluted with dichloromethane and washed with an aqueous solution of sodium hydrogencarbonate and saturated solution of sodium chloride, and the organic layer was dried over anhydrous magnesium sulfate. After the magnesium sulfate was removed by filtration, the organic layer was concentrated in a vacuum.

(2) The residue was directly dissolved in methanol (16 ml) without purification, the solution was cooled to −15° C., $BH_3NH_3$ (122 mg, 3.95 mmols) were added to the solution, and the reaction temperature was returned to room temperature. The disappearance of the material was confirmed by TLC, and the reaction mixture was thereafter concentrated as it was in a vacuum. The residue was purified by silica gel column chromatography (ethyl acetate:hexane=2:1), affording an 8-epimer (yield 1.05 g).

(e) The 8-epimer (533 mg, 0.87 mmols) obtained above was dissolved in dichloromethane (13 ml), followed by cooling to −15° C. under an argon stream. Dimethylaminosulfur trifluoride (580 ml, 3.51 mmols) was slowly added to the solution, followed by stirring for 30 minutes, and the reaction temperature was raised to 40° C., further followed by stirring for 16 hours. After the reaction was terminated by the addition of methanol, the reaction mixture was concentrated in a vacuum. The residue was purified by silica gel column chromatography (ethyl acetate:hexane=2:3), affording an 8-fluoro compound (yield 144 mg).

(f) The 8-fluoro compound (120 mg, 0.197 mmols) obtained above was dissolve in acetic acid (4 ml), 10% Pd/C (120 mg) was added to the solution under an argon stream, the atmosphere was replaced by hydrogen, and the mixture was thereafter stirred at room temperature. The completion of reaction was confirmed by TLC 2 hours later, the reaction mixture was filtered with activated carbon, and the filtrate was concentrated in a vacuum. The residue was purified by silica gel column chromatography (ethyl acetate:methanol=6:1) to obtain a compound (yield 57 mg).

(g) (1) The compound (50 mg, 0.147 mmol) obtained above was dissolved in methanol (2 ml), 0.3 N sodium hydroxide aqueous solution (2 ml) was added to the solution, and the mixture was stirred at room temperature. The completion of reaction was confirmed by TLC, and the reaction mixture was thereafter neutralized with IR-120(+). IR-120(+) was removed by filtration, and the filtrate was concentrated in a vacuum.

(2) The residue was dissolved as it was in 0.016 N hydrochloric aqueous solution (5 ml), Amberlyst 15(H+) (150 mg) was added to the solution, and the mixture was reacted at 75° C. for 24 hours. The completion of reaction was confirmed by NMR spectroscopy, and the reaction mixture was concentrated in a vacuum. The residue was placed on AG1xX8 (200-400 mesh, formate form), 150 ml of water was passed through the column, and a 1M formic acid aqueous solution was thereafter applied for elution, giving 8-fluorosialic acid (27) (yield 33 mg).

NMR data as to 8-fluorosialic acid is given below.

$^1$H-NMR (400 MHz, $D_2O$) δ 4.69 (dddd, 1H, $J_{8,F}$=48.7 Hz, $J_{8,9a}$=5.0 Hz, $J_{8,9b}$=3.5 Hz, H-8), 4.03 (ddd, 1H, $J_{4,5}$=10.0 Hz, $J_{3ax,4}$=11.1 Hz, $J_{3eq,4}$=4.7 Hz, H-4), 3.95 (dd, 1H, $J_{4,5}$=10.0 Hz, $J_{5,6}$=9.9 Hz, H-5), 3.94 (ddd, 1H, $J_{6,7}$=~0 Hz, $J_{7,8}$=6.8 Hz, $J_{7,F}$=14.0 Hz, H-7), 3.88 (ddd, 1H, $J_{9a,9b}$=13.3 Hz, $J_{9a,8}$=3.5 Hz, $J_{9b,F}$=28.0 Hz, H-9b), 3.86 (dd, 1H, $J_{5,6}$=9.9 Hz, $J_{6,7}$=~0 Hz, H-6), 3.72 (ddd, 1H, $J_{9a,9b}$=5.33 Hz, $J_{9a,8}$=5.0 Hz, $J_{9a,F}$=30.6 Hz, H-9a), 2.28 (dd, 1H, $J_{3eq,3ax}$=13.00, $J_{3eq,4}$= 4.6 Hz, H-3 eq), 2.05 (s, 3H, Ac), 1.87 (dd, 1H, $J_{3ax,4}$=11.1 Hz, $J_{3eq,3ax}$=13.00, H-3ax)

REFERENCE EXAMPLE 13

Preparation of 5-Acetamido-3,5,9-trideoxy-9-fluoro-D-glycero-β-D-galacto-2-nonulopyranosidonic acid (28)

5-Acetamido-3,5,9-trideoxy-9-fluoro-D-glycero-β-D-galacto-2-nonulopyranosidonic acid (28) was prepared from Sialic acid (26) according to the scheme given below.

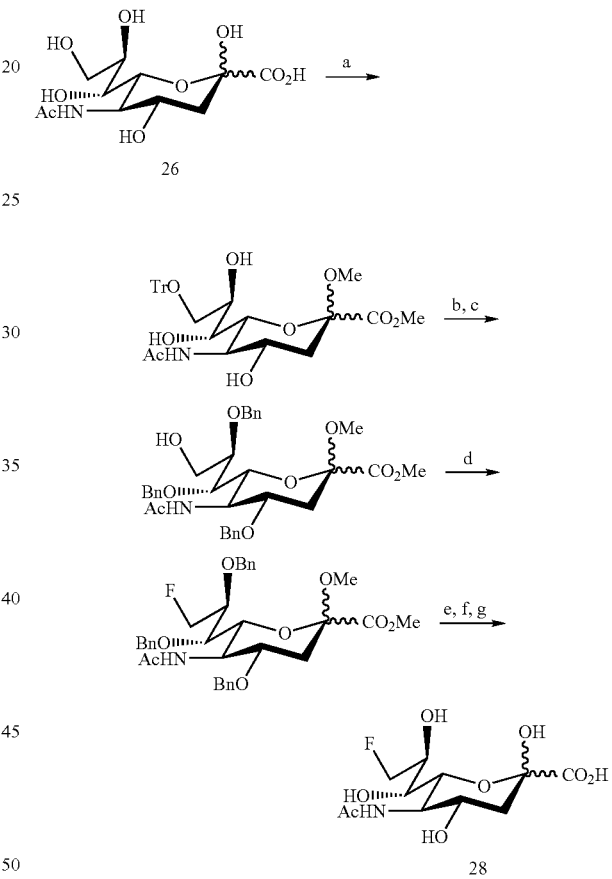

(a) (1) Dowex 50W-X8, MeOH, reflux, (2) TrCl, pyridine, 72%

(b) (1) BaO, Ba(OH), (2) DMF, (3) $CH_2CN_2$, 88%

(c) AcOH, 100° C., 78%

(d) (1) $Tf_2O$, pyridine, $CH_2Cl_2$, (2) TASF, $CH_2Cl_2$, 52%

(e) $H_2$, Pd/C(10%), AcOH, 86%

(f) NaOHaq.

(g) 0.02N HClaq., Amberlyst 15(H+), 86%

The above reactions were conducted according to the literature below.

T. Miyazaki, T. Sakakibara, H. Sato, Y. Kajihara; Chemoenzymatic Synthesis of the 9-Deoxy-9-fluoro-[3-

13C]-NeuAc-a-(2,6)-[U-13C]-Gal-b- Sequence on An Intact Glycoprotein. J. Am. Chem. Soc., 121, 1411-1412 (1999).

REFERENCE EXAMPLE 14

Preparation of CMP-7-fluorosialic acid Derivative

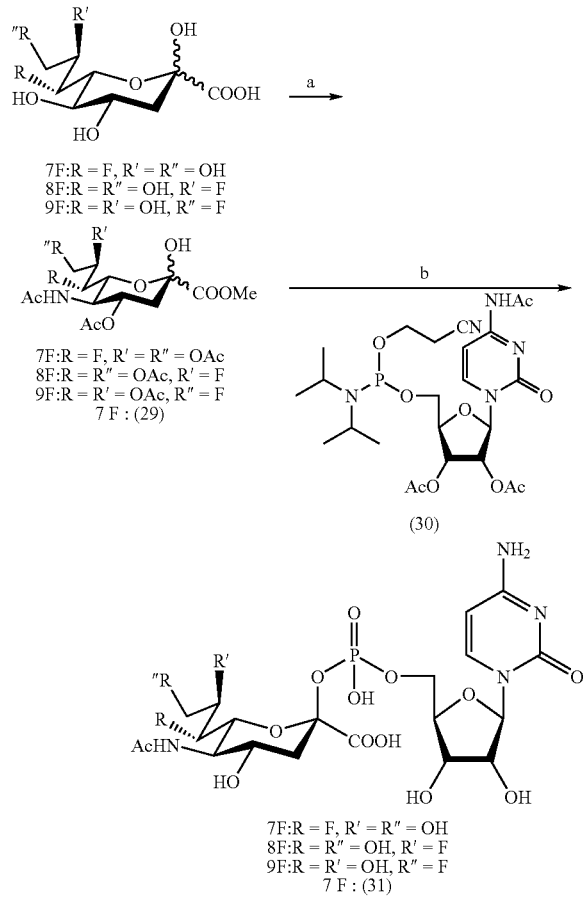

(a) (1) Dowex 50-X8, MeOH, (2) Ac$_2$O, 60% HClO$_4$;
(b) (1) 1H-Tetrazole, CH$_3$CN, (2) t-BuOOH, CH$_3$CN, (3) DBU, CH$_3$CN, (4) NaOMe, MeOH, H$_2$O A 0.074 mmol quantity of Compound (25), which is a fluorosialic acid derivative, was dissolved in distilled methanol (3 ml), Dowex-50W-X8 (65 mg) was added to the solution with stirring under an argon stream, and the mixture was reacted for 3 hours. After the completion of reaction was recognized, the reaction mixture was filtered and concentrated in a vacuum. The residue was dissolved in acetic anhydride (200 µl), a solution (22 µl) of acetic anhydride and 60% perchloric acid (15:1) was added to the solution with stirring at −20° C., and the mixture was reacted at 0° C. for 40 minutes. After the completion of reaction was recognized, the reaction mixture was diluted with ethyl acetate and washed with a saturated aqueous solution of sodium hydrogencarbonate. The organic layer was dried over anhydrous magnesium sulfate, followed by filtration and subsequent concentration in a vacuum to obtain a residue containing Compound (29). The residue and CMP-5'-phosphoamidite derivative (30) (136 mg, 0.23 mmol) were azeotropically boiled with respective portions of benzene three times, the residue was dissolved in distilled acetonitrile (100 µl) each time, and the resulting solutions were mixed together. To the resulting solution was added 1H-tetrazole (17 mg, 0.23 mmol) with stirring in ice water under an argon stream. The mixture was returned to room temperature 5 minutes later, followed by a further reaction for 10 minutes. After the completion of reaction was recognized, the reaction mixture was diluted with ethyl acetate and washed with a saturated aqueous solution of sodium hydrogencarbonate and saturated aqueous solution of sodium chloride. The organic layer was dried over anhydrous magnesium sulfate, followed by filtration and concentration at a temperature of up to 30° C. and further by azeotropic boiling with toluene twice to remove water. Distilled acetonitrile (400 µl) was added to the residue, and 2.5M t-BuOOH toluene solution (290 µl) was added dropwise to the mixture with ice cooling under an argon stream. The mixture was returned to room temperature 5 minutes later, followed by stirring for 20 minutes. After completion of reaction was recognized, dimethyl sulfide (53 µl) was added dropwise to the mixture, and the t-BuOOH was quenched. DBU (18 µl) was thereafter added dropwise to the mixture, followed by stirring at room temperature for 20 minutes. After the completion of reaction was recognized, methanol (0.67 ml), water (1.35 ml) and sodium methoxide (360 mg) were added to the reaction mixture, followed by reaction at room temperature for 16 hours. After the completion of reaction was recognized, the reaction mixture was subjected to extraction with water, and the extract was washed with dichloromethane. The aqueous layer was concentrated in a vacuum to about 8 ml at a temperature of up to 25□ C. The resulting aqueous solution was purified by gel column chromatography (developing solvent: 20 mM ammonia water, flow rate: 0.3 ml/min), giving CMP-fluoro-sialic acid derivative (31).

The NMR data of CMP-7"-deoxy-7"-fluoro-sialic acid (31) is given below.

$^1$H-NMR (400 MHz, 50 mM ND$_4$DCO$_3$ in D$_2$O), δ 8.04 (d, 1H, J$_{5,6}$=7.6 Hz, H-6), 6.20 (d, 1H, J$_{6,5}$=7.6 Hz, H-5), 6.06 (d, 1H, J$_{1',2'}$=4.5 Hz, H-1'), 4.54 (dd, 1H, J$_{7'',8''}$=9.5 Hz, J$_{7'',F}$=45.9 Hz, H-7"), 4.42~4.20 (m, 7H, H-2', H-3', H-4', H-5' a, H-5' b, H-6", H-8"), 4.16 (ddd, 1H, J$_{4'',3''eq}$=4.7 Hz, J$_{4'',3''ax}$=11.3 Hz, J$_{4,5}$=10.3 Hz, H-4"), 4.03 (dd, 1H, J$_{5'',4''}$=J$_{5'',6''}$=10.3 Hz, H-5"), 3.91 (ddd, 1H, J$_{9''a,9''b}$=12.2 Hz, J$_{9''a,8''}$=2.8 Hz, J$_{9''a,F}$=2.8 Hz, H-9" a), 3.75 (ddd, 1H, J$_{9''a,9''b}$=12.2 Hz, J$_{9''b,8}$=5.4 Hz, J$_{9''b,F}$=2.1 Hz, H-9" b), 2.61 (dd, 1H, J$_{3''eq,4''}$ = 4.7 Hz, J$_{gem}$=13.3 Hz, H-3" eq), 2.14 (s, 3H, Ac), 1.76 (ddd, 1H, J$_{3''ax,4''}$=11.5 Hz, J$_{gem}$=13.3 Hz, J$_{3''ax,P}$=5.6 Hz, H-3" ax)

REFERENCE EXAMPLE 15

Preparation of CMP-8"-deoxy-8"-fluoro-sialic acid

CMP-8"-deoxy-8"-fluoro-sialic acid was prepared in the same manner as in Reference Example 14 with the exception of using Compound (27) in place of Compound (25). NMR data is given below.

$^1$H-NMR (400 MHz, 50 mM ND$_4$DCO$_3$ in D$_2$O) δ 8.08 (d, 1H, J$_{5,6}$=7.6 Hz, H-6), 6.20 (d, 1H, J$_{6,5}$=7.6 Hz, H-5), 6.09 (d, 1H, J$_{1',2'}$=4.1 Hz, H-1'), 4.90 (m, 1H, H-8"), 4.42 (dd, 1H, J$_{3',2'}$=J$_{3',4'}$=4.9 Hz, H-3'), 4.39 (dd, 1H, J$_{2',1'}$=4.1 Hz, J$_{2',3'}$=4.9 Hz, H-2'), 4.31-4.28 (m, 3H, H-4', H-5' a, H-5' b), 4.15 (ddd, 1H, J$_{4'',3''eq}$=4.4 Hz, J$_{4'',3''ax}$=11.5 Hz, J$_{4,5}$=10.5 Hz, H-4"), 4.10-3.90 (m, 5H, H-5", H-6", H-7", H-9" a, H-9" b), 2.60 (dd, 1H, J$_{3''eq,4''}$=4.4 Hz, J$_{gem}$=13.1 Hz, H-3" eq), 2.13 (s, 3H, Ac), 1.77 (ddd, 1H, J$_{3''ax,4''}$=11.5 Hz, J$_{gem}$=13.1 Hz, J$_{3''ax,P}$=4.5 Hz, H-3" ax)

REFERENCE EXAMPLE 16

Preparation of CMP-9"-deoxy-9"-fluoro-sialic acid

CMP-9"-deoxy-9-fluoro-sialic acid was prepared in the same manner as in Reference Example 14 with the exception of using Compound (28) in place of Compound (25).

EXAMPLE 5

Preparation of HOOC-Ser-Ser-Asn (Asialooligo)-Val-Leu-Leu-Ala-NH-Dansyl

Into a solid-phase synthesis column was placed 370 mg of HMPA-PEGA resin, which was thoroughly washed with $CH_2Cl_2$ and DMF.

Fmoc-Ser (OtBu)-OH, 1-mesitylenesulfonyl-3-nitro-1,2,4-triazole (MSNT) and N-methylimidazole were dissolved in $CH_2Cl_2$, and the solution was stirred for 5 minutes and thereafter placed into the solid-phase synthesis column containing the resin, followed by stirring at room temperature for 3 hours. The resin was thereafter washed with methylene chloride, isopropanol and DMF and dried. The unreacted hydroxyl on the solid phase was thereafter acetylated using a 20% DMF solution of acetic anhydride for 20 minutes for capping. The resin was washed with DMF and stirred along with a 20% piperidine/DMF solution for 20 minutes to remove the protective Fmoc group, whereby resin-Ser-$NH_2$ was obtained. The product was washed with DMF and dried.

Next, Fmoc-Ser(OtBu)-OH was used with $HOBt.H_2O$ and DIPCDI for condensation.

Subsequently, Fmoc-asparagine-linked asialooligosaccharide was dissolved in a 1:1 solvent mixture of DMSO and DMF, and the solution, HATU and DIPEA were stirred at room temperature for 24 hours for condensation. The resulting resin was washed with DMF and thereafter stirred along with 10% acetic anhydride/2-propanol:methanol for 20 minutes for capping. The resin was washed with 2-propanol and DMF, and thereafter stirred along with 20% piperidine/DMF for 20 minutes to remove the protective Fmoc group. The resin was washed with DMF.

The resulting resin, and valine (Val), leucine (Leu), leucine (Leu) and alanine (Ala) were similarly subjected to condensation, followed by removal of the protective Fmoc group to obtain resin-Ser-Ser-Asn(asialooligo)-Val-Leu-Leu-Ala-$NH_2$.

Used as the amino acids of valine (Val), leucine (Leu), and alanine (Ala) were each Fmoc-AA-Opfp (AA=amino acid) wherein the carboxyl was pfp-esterified, and 3,4-dihydro-4-oxo-1,2,3-benzotriazin-3-yl (Dhbt) was used for condensation. All condensation reactions were conducted in a DMF solution. For fluorescence marking, the resin was reacted with dansyl chloride and diisopropylethylamine in DMF for 30 minutes. After the completion of dansylation, the resin was washed with DMF and $CH_2Cl_2$.

To the washed resin was added a 95% aqueous solution of TFA, followed by stirring at room temperature for 3 hours to cut off the resin. The resin was filtered off. The reaction mixture was concentrated in a vacuum at room temperature, thereafter dissolved in water and freeze-dried. The resulting product was purified by HPLC to obtain the desired product, i.e., HOOC-Ser-Ser-Asn(asialooligo)-Val-Leu-Leu-Ala-NH-Dansyl.

(YMC-Pack A-314 S-5 ODS 300×6.0 mm, developing solvents A: 0.1% TFA aqueous solution, B: 0.1% TFA acetonitrile:water=90:10, gradient A 100% 0.60 ml/min→B 100% 0.60 ml/min 60 min).

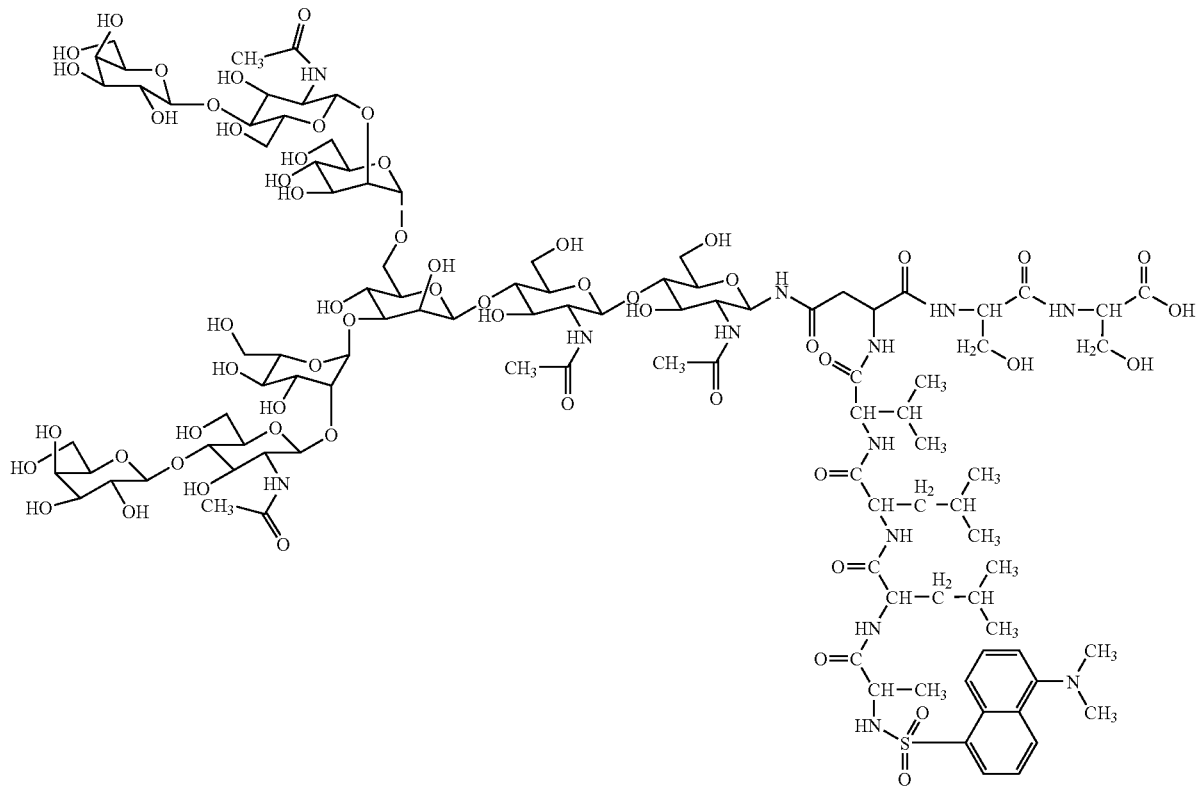

EXAMPLE 6

Preparation of HOOC-Ser-Ser-Asn(asialooligo)-Val-Leu-Leu-Ala-NH$_2$

HOOC-Ser-Ser-Asn (asialooligo)-Val-Leu-Leu-Ala-NH$_2$ was prepared in the same manner as in Example 5 with the exception of not conducting dansylation for fluorescence marking.

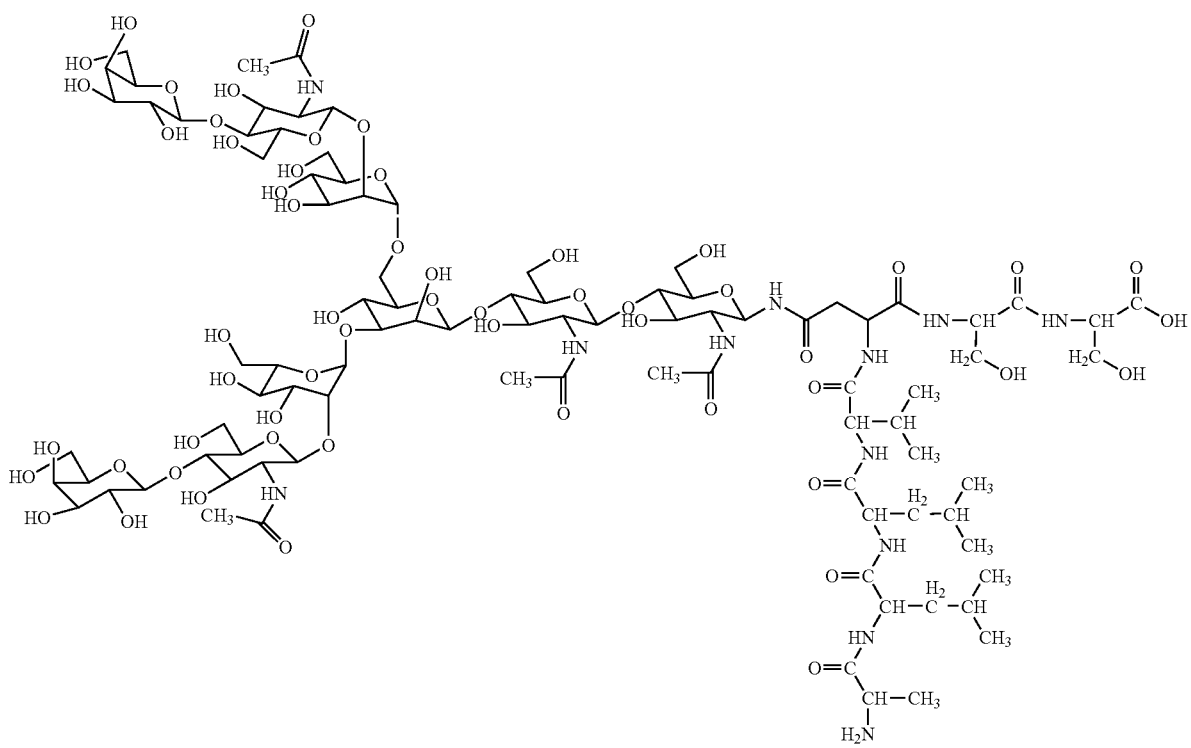

EXAMPLE 7

The sialic acid derivative of Reference Example 14 was transferred to the dansylated asialooligosaccharide peptide obtained in Example 5, using a sialic acid transferase.

Used as the sialic acid transferase was a commercial product derived from a rat recombinant and serving as an α2,3-transferase.

The enzymatic reaction was conducted using the CMP-sialic acid derivative in four equivalents of the dansylated asialooligosaccharide peptide, 50 mM cacodylic acid buffer (pH 5.0) serving as a reaction solvent, and a phosphoric acid hydrolase and bovine serum albumin as added to the solution to be reacted.

The reaction mixture obtained on completion of reaction was freeze-dried as it was. The dried product was purified by HPLC, giving a glycopeptide having a dansylated di-7-sialo derivative attached thereto, as given below.

(YMC-Pack A-314 S-5 ODS 300×6.0 mm, developing solvents A: 0.1% TFA aqueous solution, B: 0.1% TFA acetonitrile:water=90:10, gradient A 100% 0.60 ml/min→B 100% 0.60 ml/min 60 min)

43
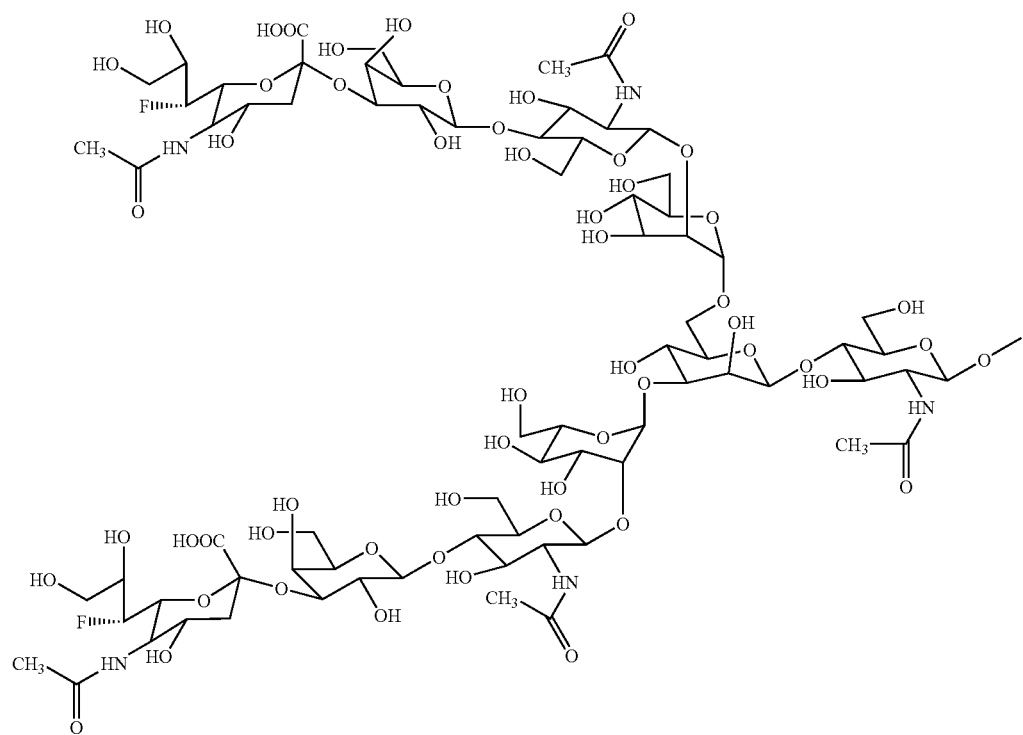
44
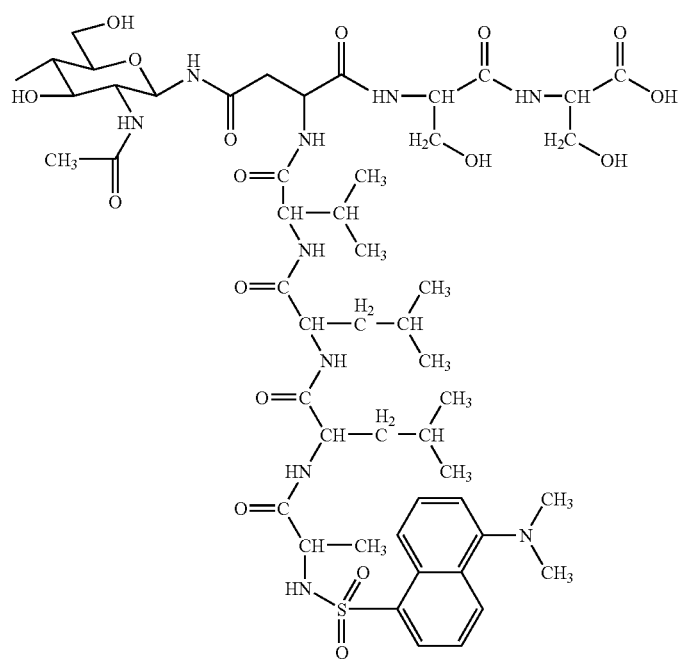

EXAMPLE 8
A glycopeptide having a dansylated di-7-sialo derivative as 2,6-linked thereto, shown below, was obtained in the same manner as in Example 7 with the exception of using as the sialic acid transferase a commercial product derived from rat liver and serving as an α2,6-transferase and using a cacodylic buffer adjusted to a pH of 6.0.
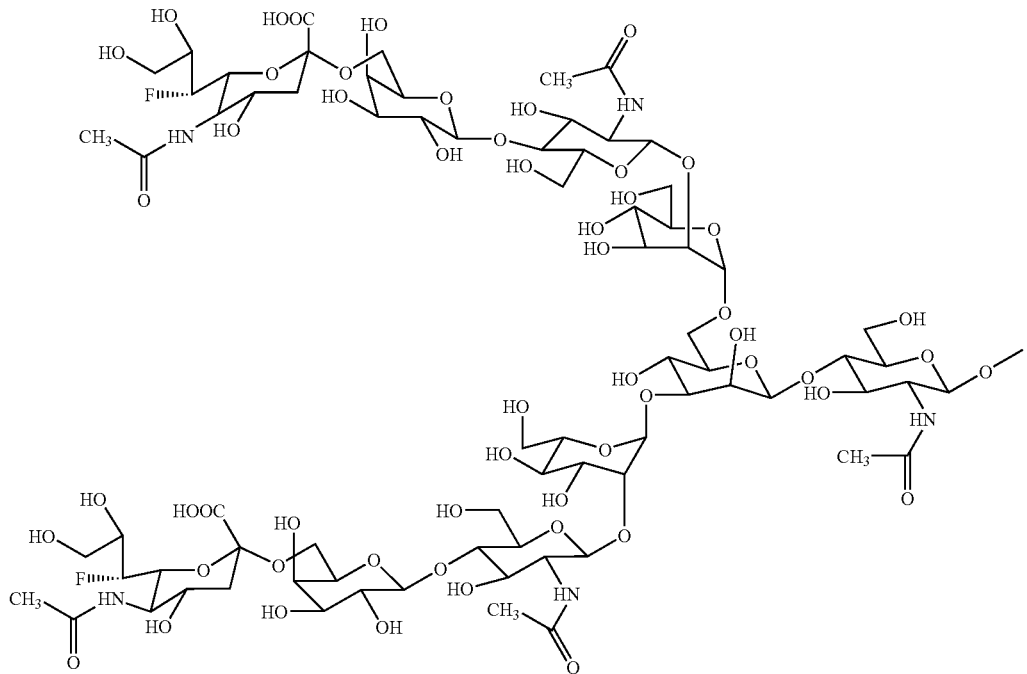
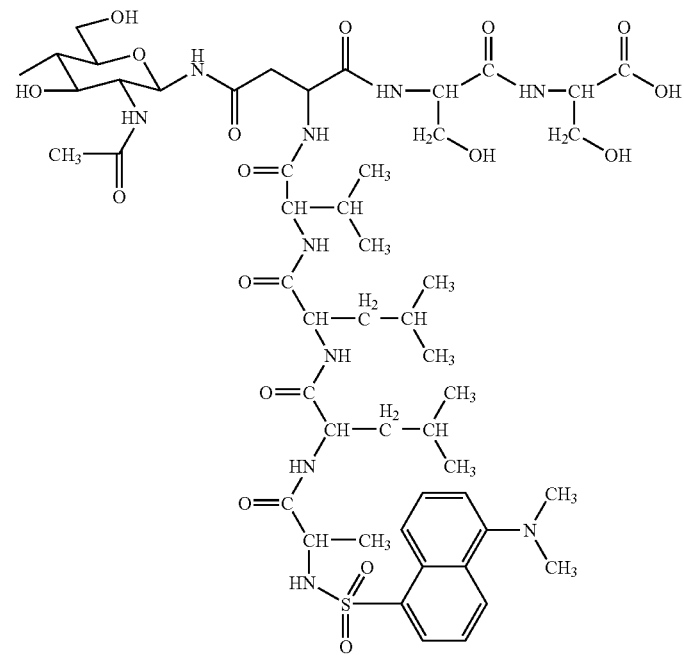

EXAMPLE 9
A glycopeptide having a di-8-sialo derivative as 2,3-linked thereto, shown below, was obtained in the same manner as in Example 7 with the exception of using the sialic acid derivative of Reference Example 15 instead of the sialic acid derivative of Reference Example 14.
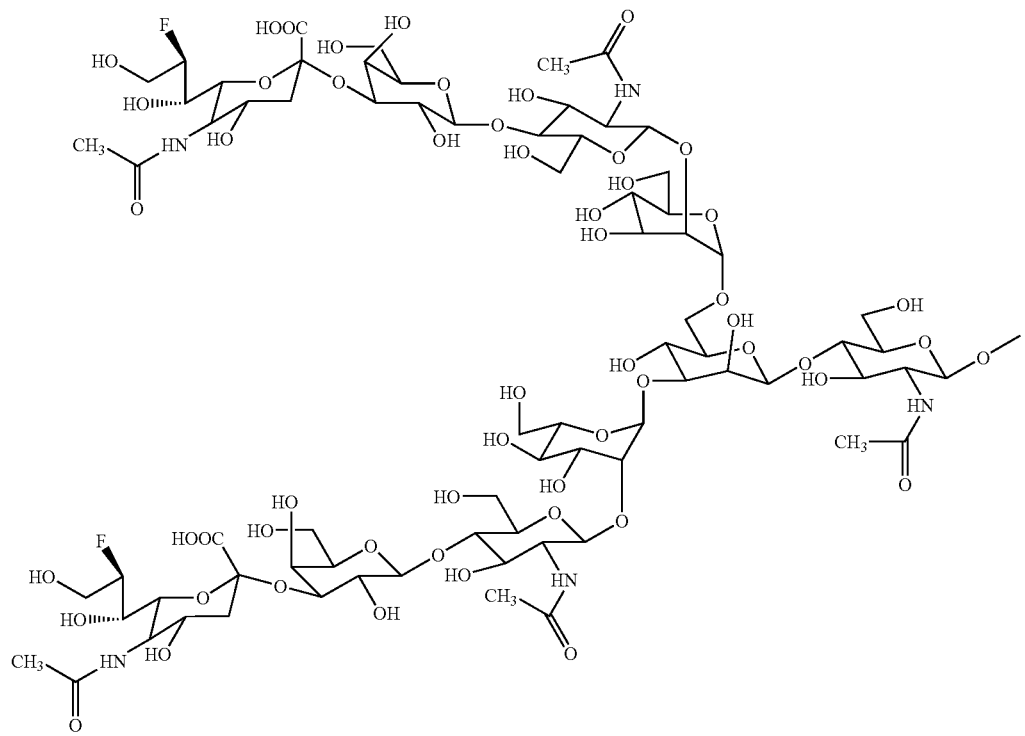
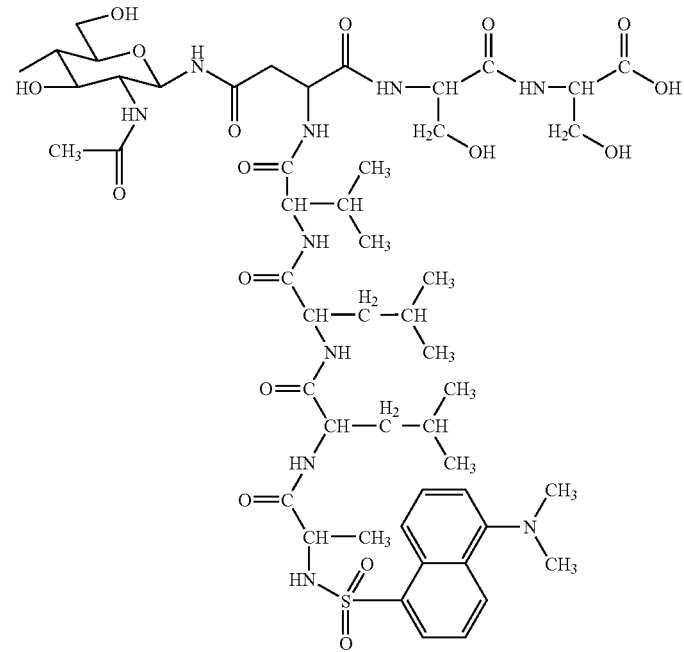

EXAMPLE 10
A glycopeptide having a di-8-sialo derivative as 2,6-linked thereto, shown below, was obtained in the same manner as in Example 8 with the exception of using the sialic acid derivative of Reference Example 15 instead of the sialic acid derivative of Reference Example 14.
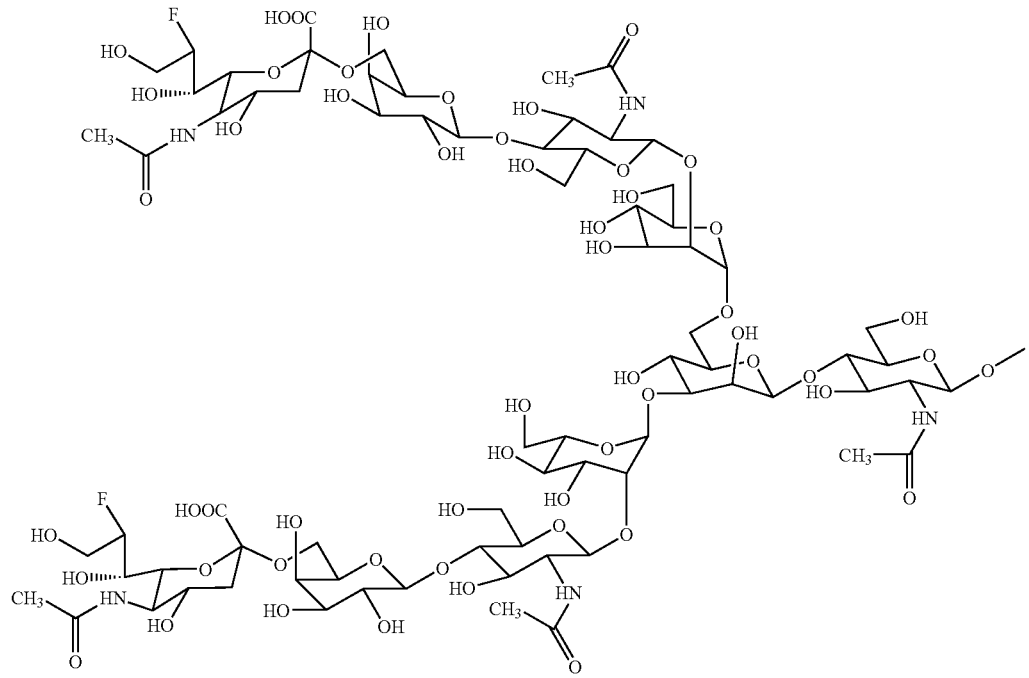
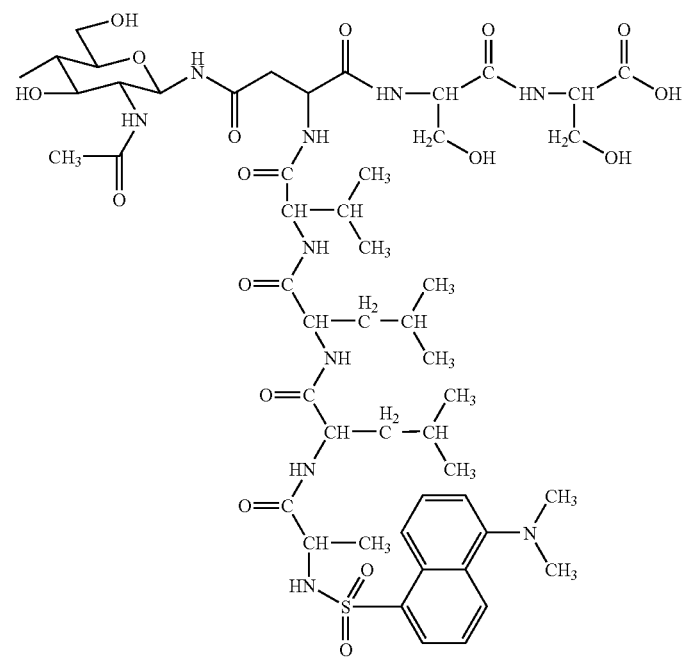

EXAMPLE 11
A glycopeptide having a di-9-sialo derivative as 2,3-linked thereto, shown below, was obtained in the same manner as in Example 7 with the exception of using the sialic acid derivative of Reference Example 16 instead of the sialic acid derivative of Reference Example 14.
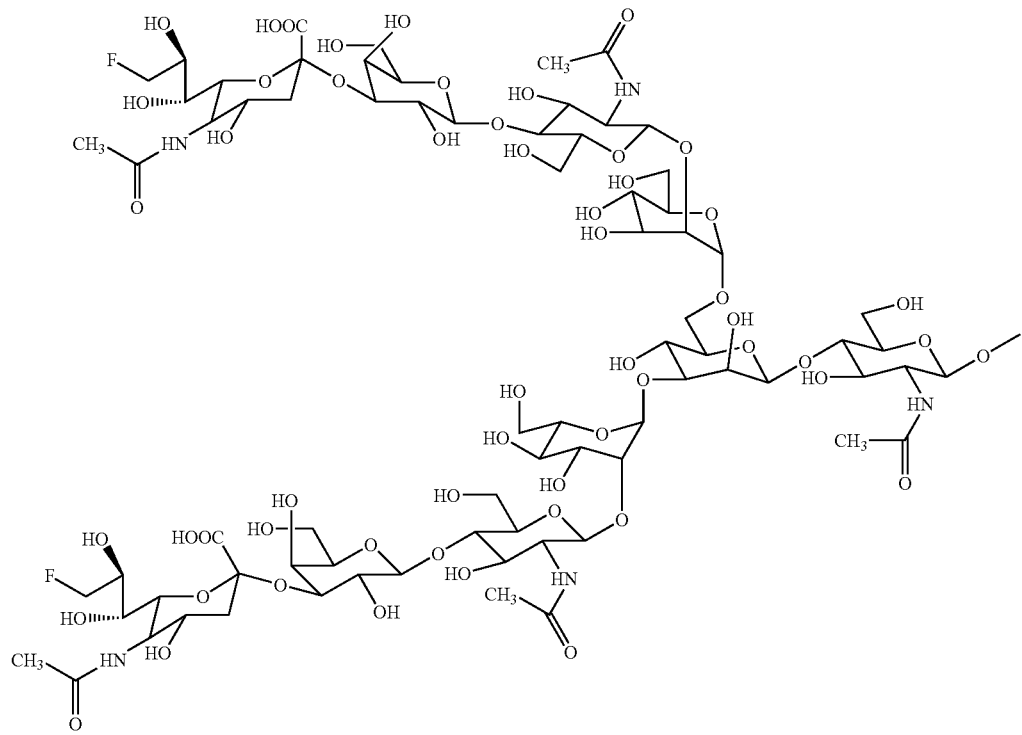
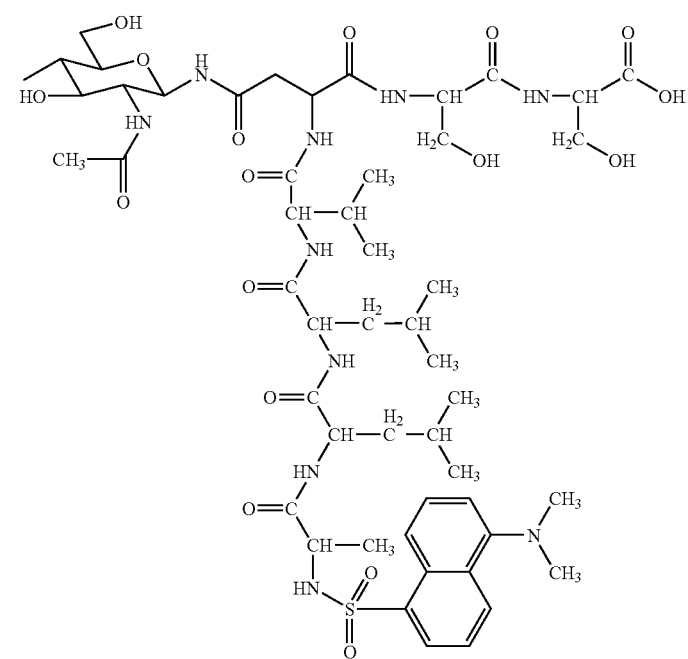

EXAMPLE 12
A glycopeptide having a di-9-sialo derivative as 2,6-linked thereto, shown below, was obtained in the same manner as in Example 8 with the exception of using the sialic acid derivative of Reference Example 16 instead of the sialic acid derivative of Reference Example 14.
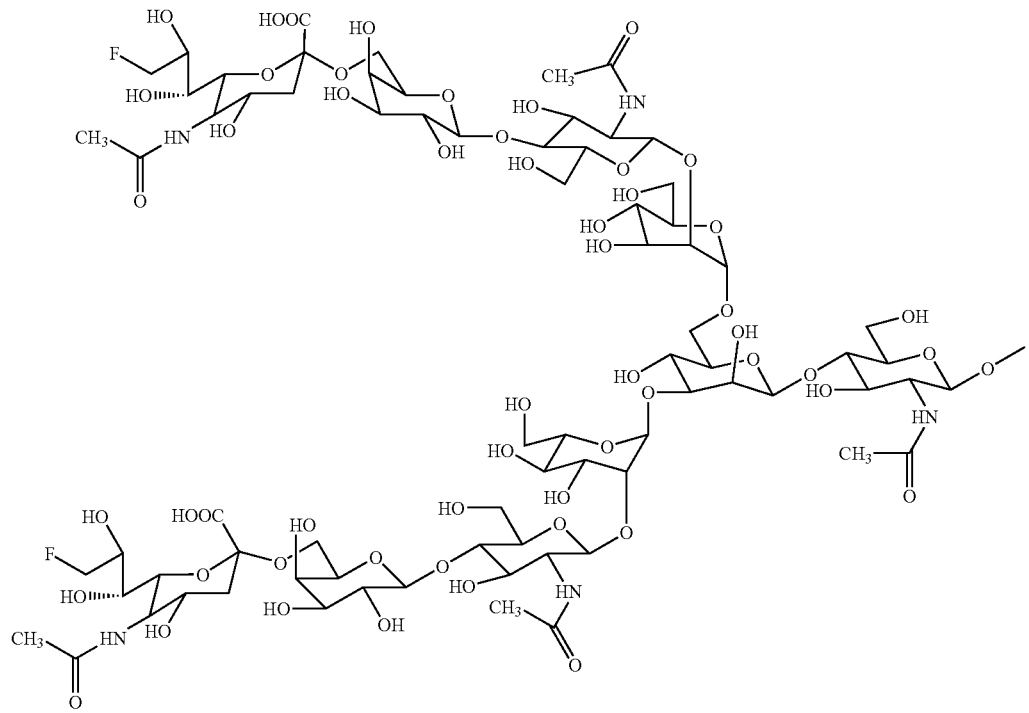
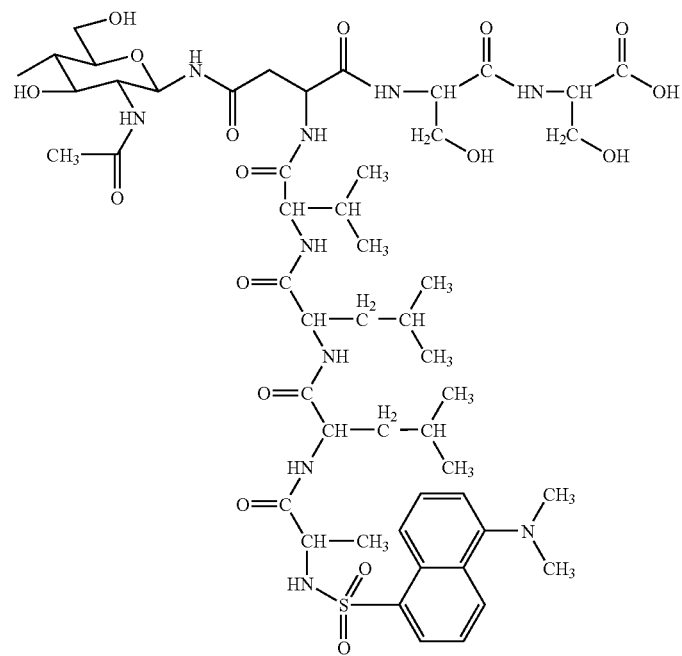

EXAMPLE 13
A glycopeptide having a di-7-sialo derivative as 2,3-linked thereto, shown below, was obtained in the same manner as in Example 7 with the exception of using the asialooligosaccharide peptide not dansylated and obtained in Example 6.
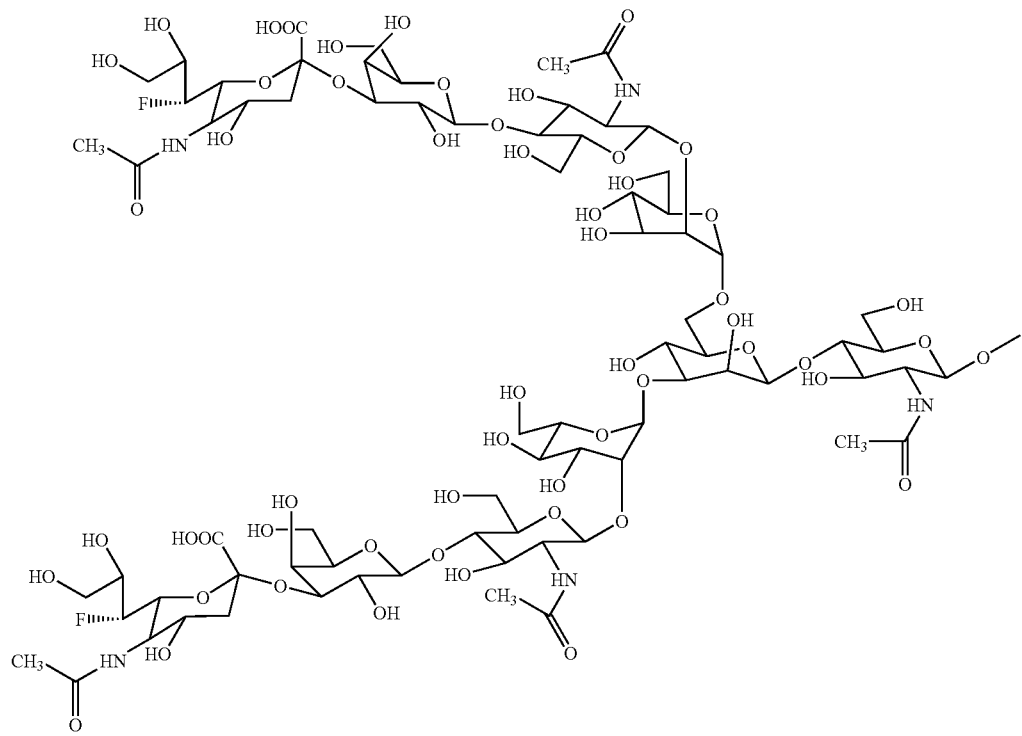
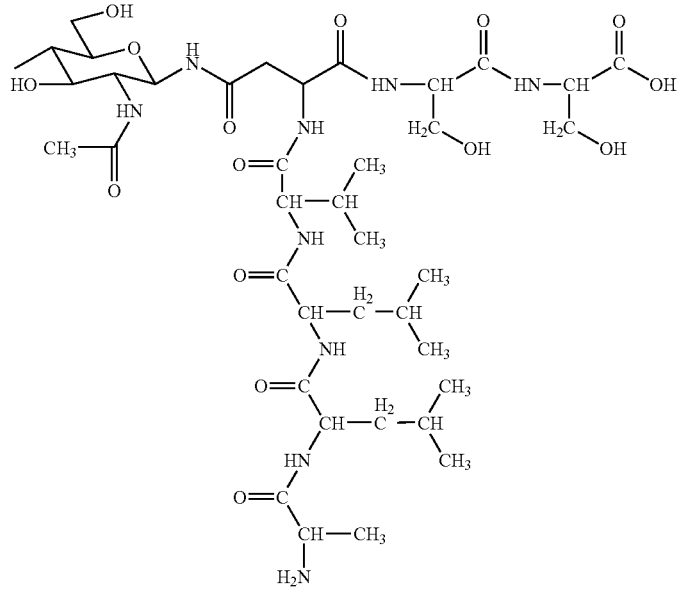

EXAMPLE 14
A glycopeptide having a di-7-sialo derivative as 2,6-linked thereto, shown below, was obtained in the same manner as in Example 8 with the exception of using the asialooligosaccharide peptide not dansylated and obtained in Example 6.
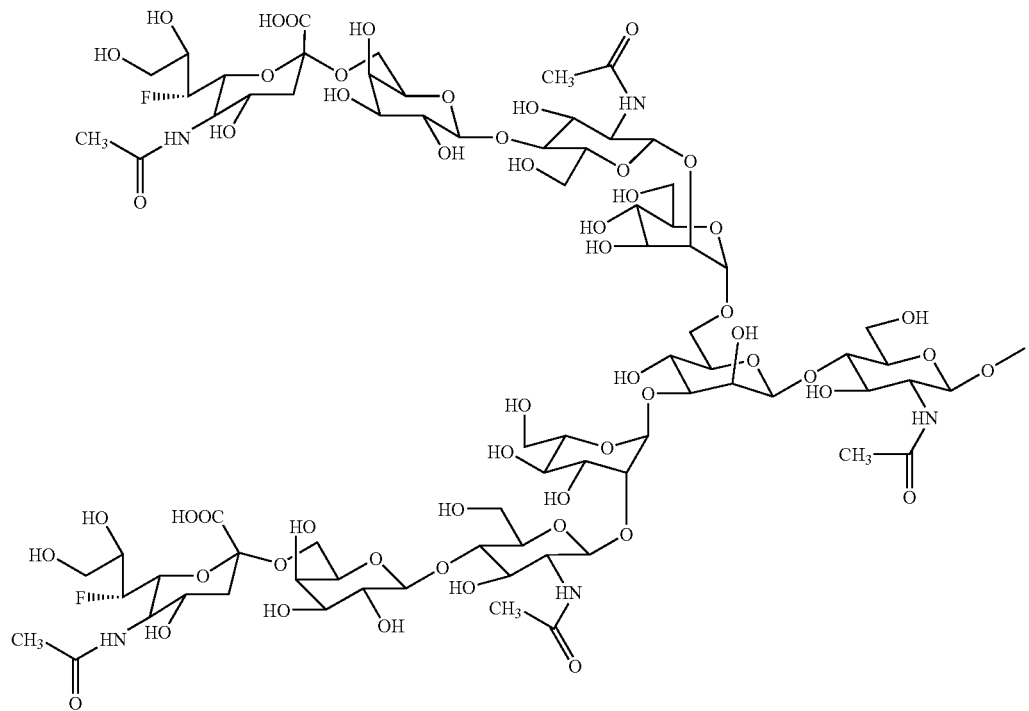
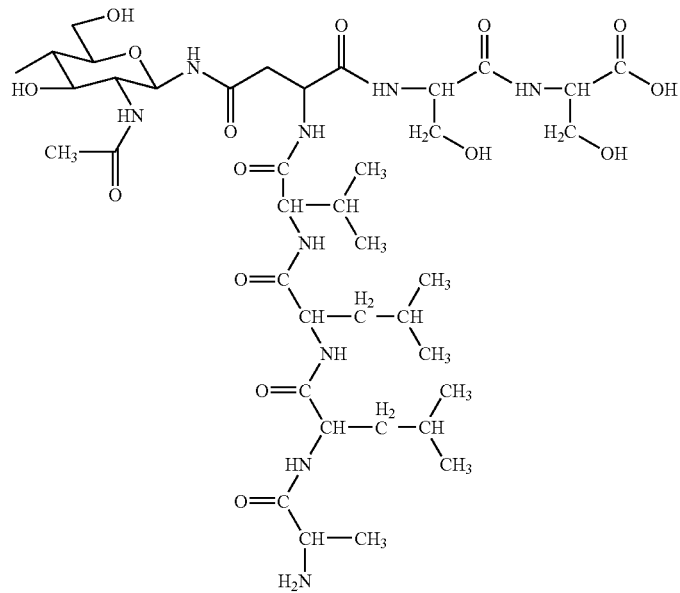

EXAMPLE 15
A glycopeptide having a di-8-sialo derivative as 2,3-linked thereto, shown below, was obtained in the same manner as in Example 9 with the exception of using the asialooligosaccharide peptide not dansylated and obtained in Example 6.
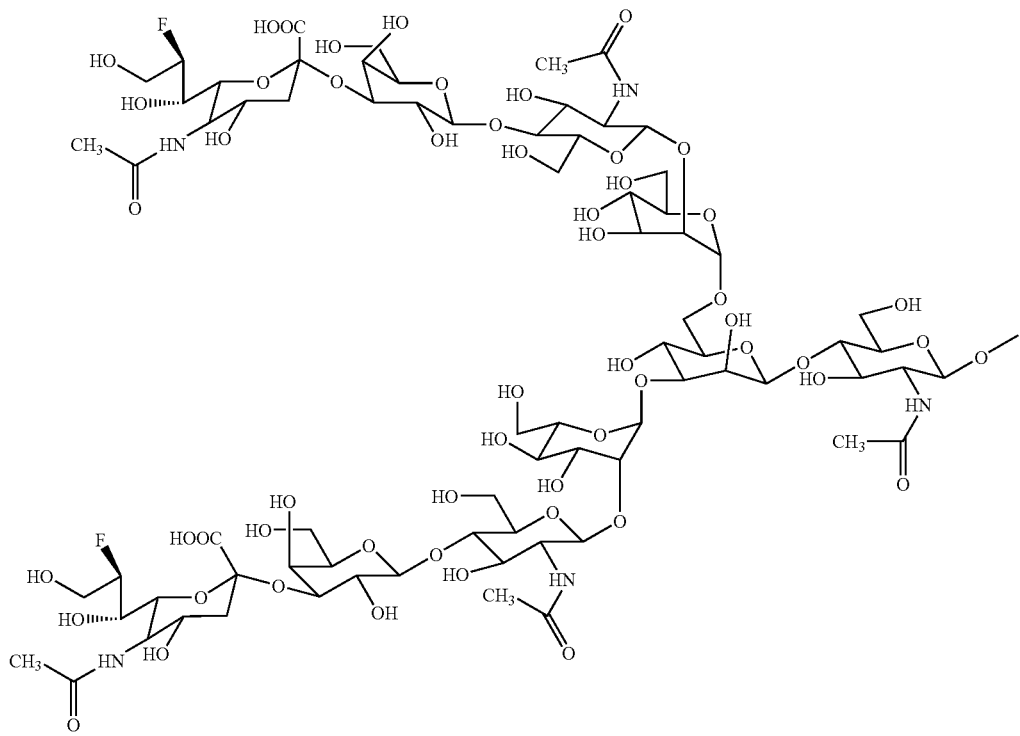
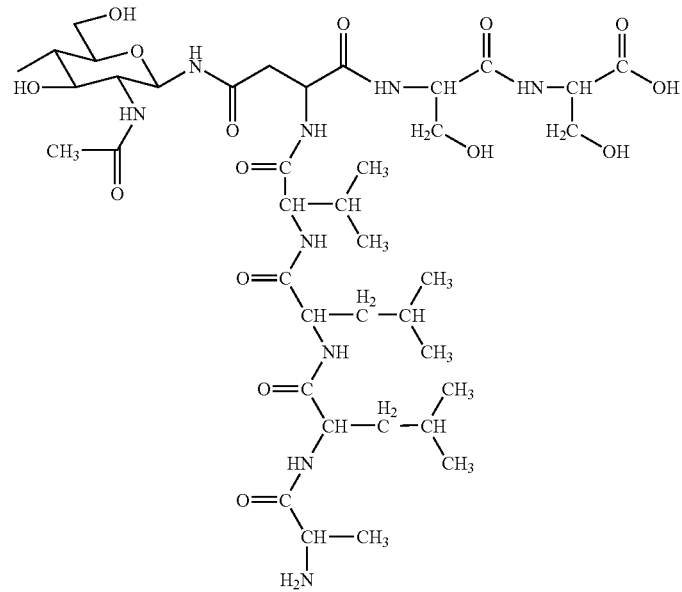

EXAMPLE 16
A glycopeptide having a di-8-sialo derivative as 2,6-linked thereto, shown below, was obtained in the same manner as in Example 10 with the exception of using the asialooligosaccharide peptide not dansylated and obtained in Example 6.
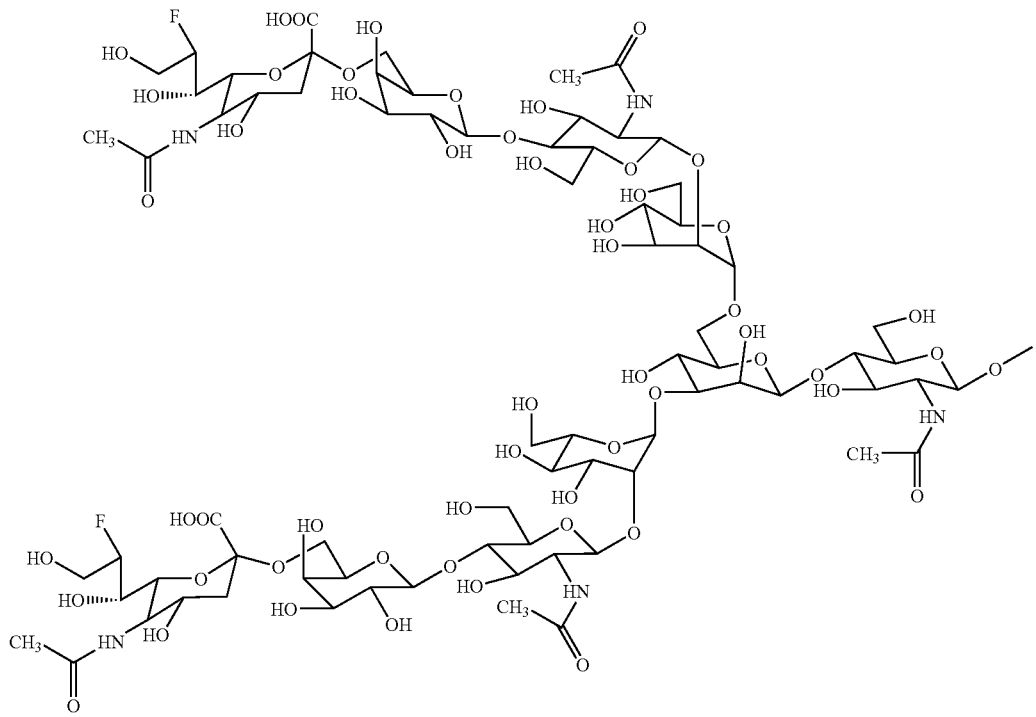
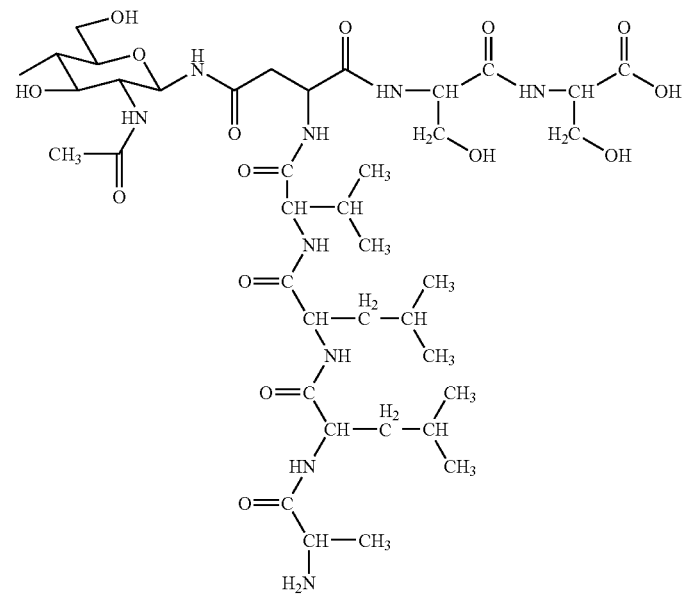

EXAMPLE 17
A glycopeptide having a di-9-sialo derivative as 2,3-linked thereto, shown below, was obtained in the same manner as in Example 11 with the exception of using the asialooligosaccharide peptide not dansylated and obtained in Example 6.
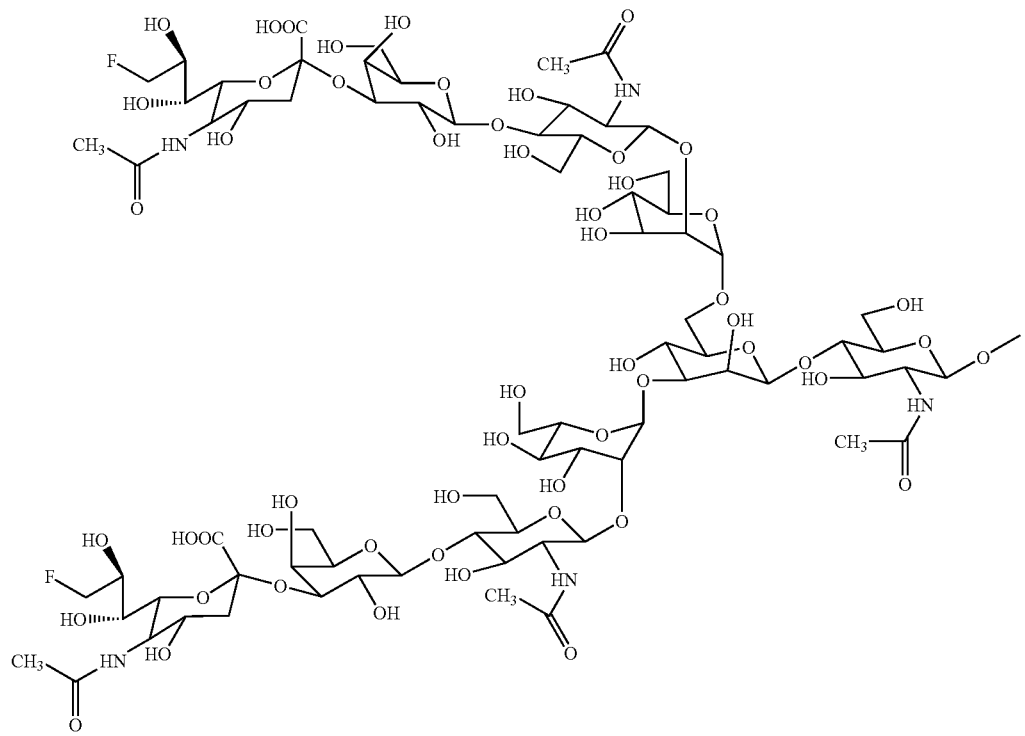
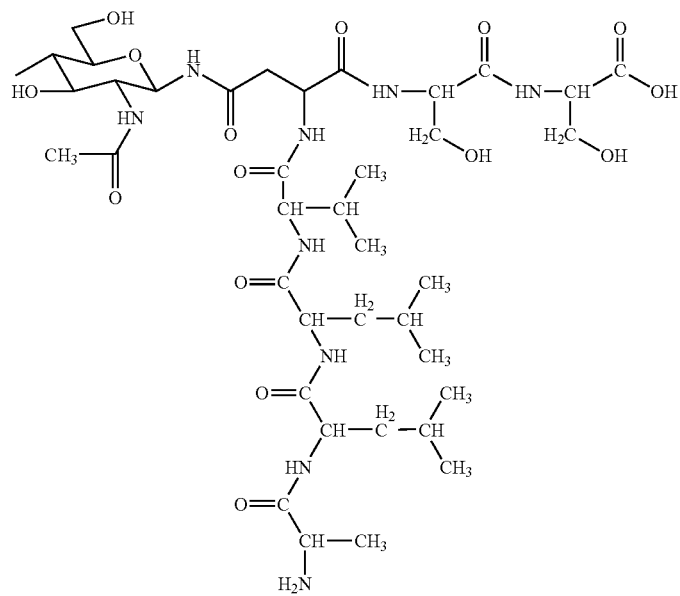

EXAMPLE 18

A glycopeptide having a di-9-sialo derivative as 2,6-linked thereto, shown below, was obtained in the same manner as in Example 12 with the exception of using the asialooligosaccharide peptide not dansylated and obtained in Example 6.

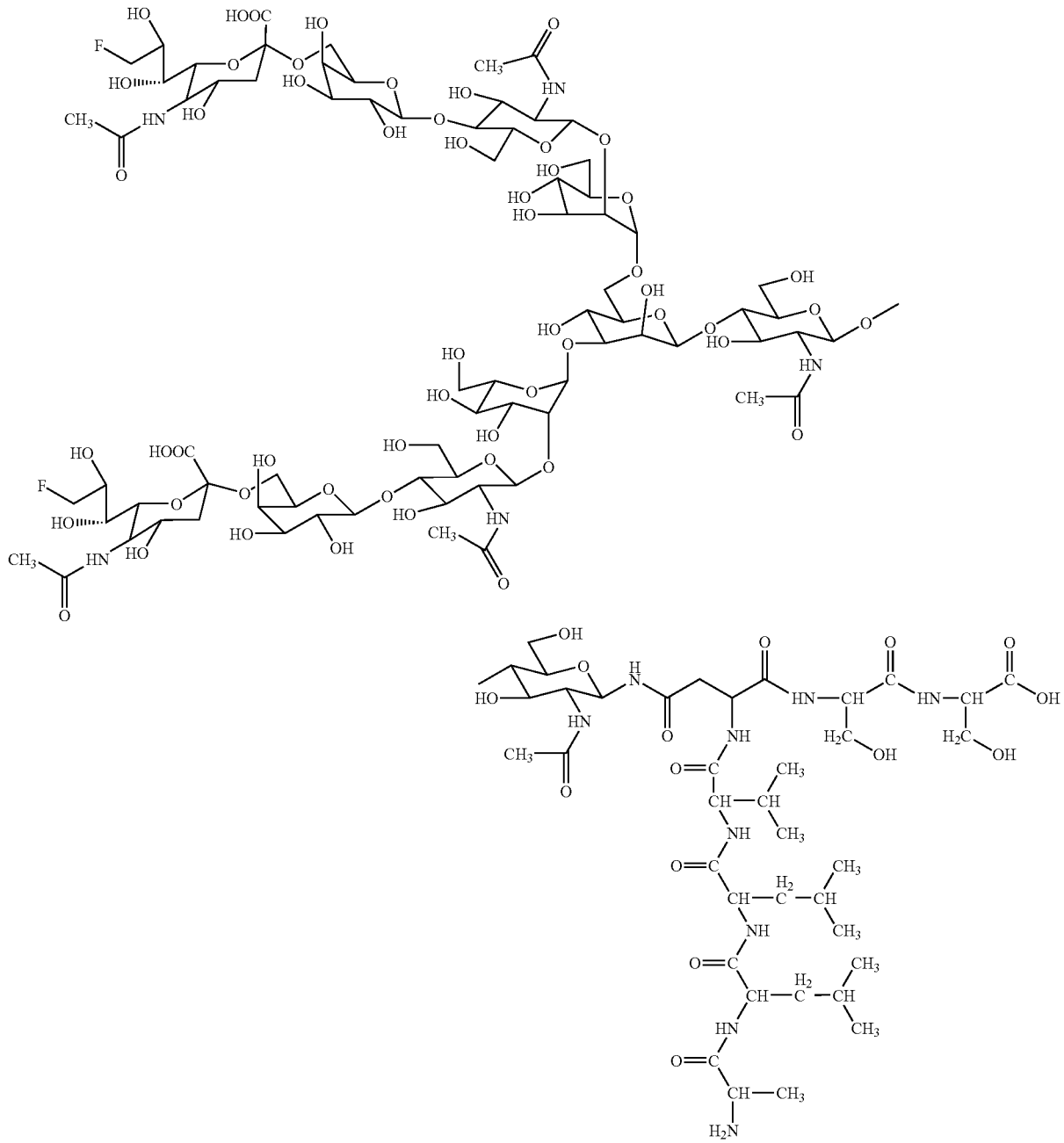

EXAMPLE 19

Preparation of HOOC-Ser-Thr-Thr-Asp-Asn(disialooligo)-Asp-Ile-Pro-NH$_2$

Asn(disialooligo) in the desired glycopeptide mentioned above means a disialooligoasparagine having sialic acid not protected with benzyl group.

Into a solid-phase synthesis column was placed 50 mg of HMPA-PEGA resin, which was thoroughly washed with $CH_2Cl_2$ and DMF.

Fmoc-Ser(OtBu)-OH, 1-mesitylenesulfonyl-3-nitro-1,2,4-triazole (MSNT) and N-methylimidazole were dissolved in $CH_2Cl_2$, and the solution was stirred for 5 minutes and thereafter placed into the solid-phase synthesis column containing the resin, followed by stirring at room temperature for 3 hours. The resin was thereafter washed with methylene chloride, isopropanol and DMF and dried. The unreacted hydroxyl group on the solid phase was thereafter acetylated using a 20% DMF solution of acetic anhydride for 20 minutes for capping. The resin was washed with DMF and stirred along with a 20% piperidine/DMF solution for 20 minutes to remove the protective Fmoc group, whereby resin-Ser-NH$_2$ was obtained. The product was washed with DMF and dried.

Next, Fmoc-Thr(OtBu)-OH, Fmoc-Thr (OtBu)-OH and Fmoc-Asp(OtBu)-OH were subjected to condensation in this order using HOBt.H$_2$O and PyBOP.DIPEA. After the condensation of the amino acids, the resulting reaction mixture was stirred along with a 20% piperidine/DMF (1:1) solution to remove the protective Fmoc group.

Subsequently, dibenzyl-Fmoc-asparagine-linked disialooligosaccharide was dissolved in a 1:1 solvent mixture of DMSO and DMF, and the solution, HATU and DIPEA were stirred at room temperature for 24 hours for condensation. The resulting resin was washed with DMF and thereafter stirred along with 10% acetic anhydride/2-propanol:methanol for 20 minutes for capping. The resin was washed with DMF, a solvent mixture of DMF and 2,6-lutidine (1:1) was then added to the resin, and TESOTf was further added in an amount of 3 equiv. wt per oligosaccharide hydroxyl group, followed by reaction for 1 hour to protect each oligosaccharide hydroxyl group with a TES (triethylsilyl) group.

The resin was washed with DMF and THF, and thereafter stirred along with 20% piperidine/DMF for 20 minutes to remove the protective Fmoc group. The resin was washed with THF.

The resulting resin, and aspartic acid (Asp), isoleucine (Ile) and proline (Pro) were subjected to condensation in THF solvent using HOBt.H$_2$O and PyBOP.DIPEA, and the protective Fmoc group was removed with a 20% piperidine/THF to obtain resin-Ser-Thr-Thr-Asp-Asn(TES-protected dibenzyl-disialooligo)-Asp-Ile-Pro-NH$_2$. Asn(TES-protected dibenzyldisialooligo) mentioned means a disialooligoasparagine having sialic acid with benzyl-protected carboxyl and having TES-protected oligosaccharide hydroxyl group.

The resin resulting from condensation was thoroughly dried, and thereafter stirred along with a 95% aqueous solution of TFA at room temperature for 3 hours to cut off the protective group for amino acid.TES and the resin. The resin was filtered off. The reaction mixture was concentrated in a vacuum at room temperature, thereafter dissolved in water and freeze-dried. The resulting product was dissolved in an aqueous solution of sodium hydroxide having a pH of 11 to hydrolyze the benzyl ester for the removal of benzyl group, followed by neutralization with acetic acid. The product was freeze-dried as it was, and purified by HPLC to obtain the desired product, i.e., HOOC-Ser-Thr-Thr-Asp-Asn(disialooligo)-Asp-Ile-Pro-NH$_2$.

(Mightsyl ODS-C18 250×20 mm, developing solvents A: 0.1% TFA aqueous solution, B: 0.1% TFA acetonitrile:water=90:10, gradient A 100% O→B 100% 60 min, flow rate 2.50 ml/min).

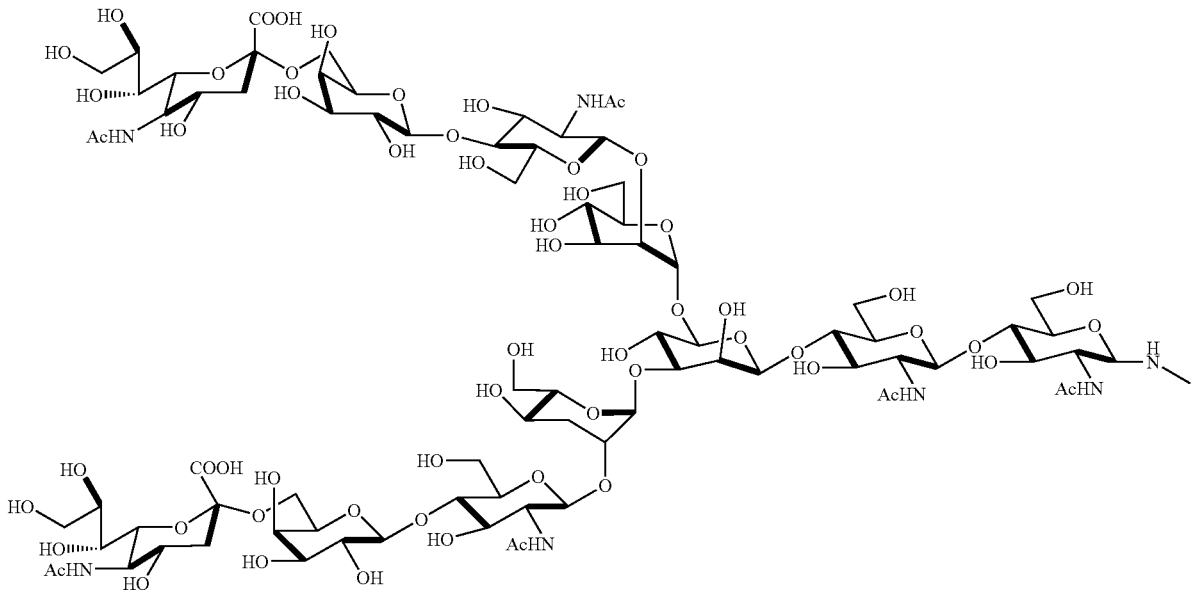

-continued

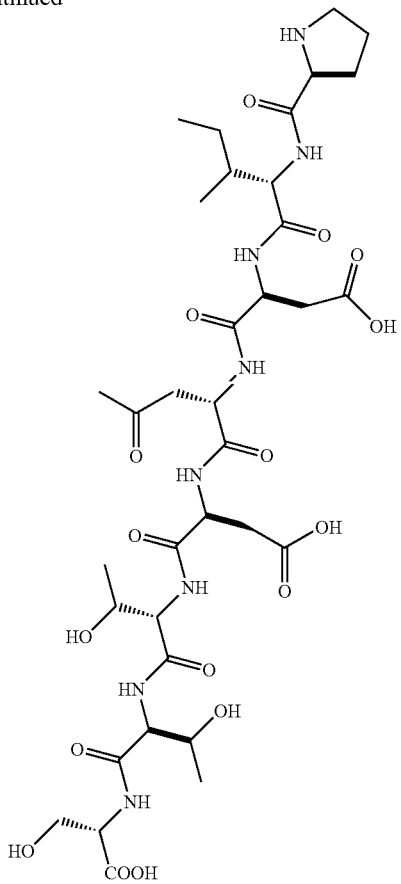

INDUSTRIAL APPLICABILITY

According to the present invention, it is possible to provide a process capable of artificially and easily preparing a large amount of a glycopeptide having at least one asparagine-linked oligosaccharide or mucin-linked oligosaccharide at a desired position of the peptide chain thereof.

Further, according to the present invention, it is possible to obtain a sialylglycopeptide which comprises an asparagine-linked oligosaccharide having sialic acid and wherein the sialic acid is not cut off from the glycopeptide by an acid treatment.

Further, according to the present invention, it is possible to obtain artificially and easily a large quantity of a glycopeptide having at least one of various novel asparagine-linked oligosaccharides at a desired position of the peptide chain thereof, with sugar residues removed therefrom as desired.

Further, according to the present invention, it is possible to obtain a glycopeptide having sialic acid or a derivative thereof introduced into the peptide with use of a sialic acid transferase.

The invention claimed is:

1. A process for preparing glycopeptide having at least one asparagine-linked oligosaccharide at a desired position of the peptide chain thereof and a residue of sialic acid or a derivative thereof at a terminal end thereof, the process comprising:
    a. esterifying a hydroxyl group of a resin having the hydroxyl group and a carboxyl group of an amino acid having amino group nitrogen protected with a fat-soluble protective group,
    b. removing the fat-soluble protective group to form a free amino group,
    c. amidating the free amino group and a carboxyl group of an amino acid having amino group nitrogen protected with a fat-soluble protective group,
    d. removing the fat-soluble protective group to form a free amino group,
    e. repeating the steps c and d at least once,
    f. amidating the free amino group and a carboxyl group of the asparagine portion of an asparagine-linked oligosaccharide having amino group nitrogen protected with a fat-soluble protective group,
    g. removing the fat-soluble protective group to form a free amino group,
    h. amidating the free amino group and a carboxyl group of an amino acid having amino group nitrogen protected with a fat-soluble protective group,
    i. repeating the steps g and h at least once,
    j. removing the fat-soluble protective group to form a free amino group,
    k. cutting off the resin with an acid, and
    l. transferring fluoro-sialic acid to the resulting glycopeptide using a sialic acid transferase and CMP-7-fluoro-sialic acid, CMP-8-fluoro-sialic acid, or CMP-9-fluoro-sialic acid.

2. A process for preparing a glycopeptide according to claim 1,
    wherein the asparagine-linked oligosaccharide of the step f of claim 1 has at least 6 sugar residues.

3. A process for preparing a glycopeptide according to claim 1, wherein the asparagine-linked oligosaccharide of the step f of claim 1 has 9 to 11 sugar residues.

4. A process for preparing a glycopeptide according to claim 1, wherein the asparagine-linked oligosaccharide of the step f of claim 1 has at least 6 sugar residues, and has a bifurcated oligosaccharide attached thereto.

5. A process for preparing a glycopeptide according to claim 1, wherein the asparagine-linked oligosaccharide in the step f is an asparagine-linked asialooligosaccharide.

6. A process for preparing a glycopeptide according to claim 1, wherein the fat-soluble protective group is 9-fluorenyl-methoxycarbonyl (Fmoc) group.

7. A process for preparing a glycopeptide according to claim 1 wherein a marker is reacted with the resin before the resin is cut off with the acid in step k.

8. A process for preparing a glycopeptide according to claim 7 wherein the marker is dansyl halide.

9. A process for preparing a glycopeptide having at least one asparagine-linked oligosaccharide at a desired position of the peptide chain thereof and a residue of a sialic acid or a derivative thereof at a terminal end thereof, the process comprising:
 a. esterifying a hydroxyl group of a resin having the hydroxyl group and a carboxyl group of an amino acid having amino group nitrogen protected with a fat-soluble protective group,
 b. removing the fat-soluble protective group to form a free amino group,
 c. amidating the free amino group and a carboxyl group of an amino acid having amino group nitrogen protected with a fat-soluble protective group,
 d. removing the fat-soluble protective group to form a free amino group,
 e. repeating the steps c and d at least once,
 f. amidating the free amino group and a carboxyl group of the asparagine portion of an asparagine-linked oligosaccharide having amino group nitrogen protected with a fat-soluble protective group,
 g. removing the fat-soluble protective group to form a free amino group,
 h. cutting off the resin with an acid, and
 i. transferring fluoro-sialic acid to the resulting glycopeptide using a sialic acid transferase and CMP-7-fluoro-sialic acid, CMP-8-fluoro-sialic acid, or CMP-9-fluoro-sialic acid.

10. A process for preparing a glycopeptide having at least one asparagine-linked oligosaccharide at a desired position of the peptide chain thereof and a residue of a sialic acid or a derivative thereof at a terminal end thereof, the process comprising:
 a. esterifying a hydroxyl group of a resin having the hydroxyl group and a carboxyl group of the asparagine portion of an asparagine-linked oligosaccharide having an amino group nitrogen protected with a fat-soluble protective group,
 b. removing the fat-soluble protective group to form a free amino group,
 c. amidating the free amino group and a carboxyl group of an amino acid having amino group nitrogen protected with a fat-soluble protective group,
 d. removing the fat-soluble protective group to form a free amino group,
 e. repeating the steps c and d at least once,
 f. cutting off the resin with an acid, and
 g. transferring fluoro-sialic acid to the resulting glycopeptide using a sialic acid transferase and CMP-7-fluoro-sialic acid, CMP-8-fluoro-sialic acid, or CMP-9-fluoro-sialic acid.

11. A process for preparing a glycopeptide having at least one asparagine-linked oligosaccharide at a desired position of the peptide chain thereof and a residue of a sialic acid or a derivative thereof at a terminal end thereof, the process comprising:
 a. esterifying a hydroxyl group of a resin having the hydroxyl group and a carboxyl group of an amino acid having amino group nitrogen protected with a fat-soluble protective group,
 b. removing the fat-soluble protective group to form a free amino group,
 c. amidating the free amino group and a carboxyl group of the asparagine portion of an asparagine-linked oligosaccharide having amino group nitrogen protected with a fat-soluble protective group,
 d. removing the fat-soluble protective group to form a free amino group,
 e. amidating the free amino group and a carboxyl group of an amino acid having amino group nitrogen protected with a fat-soluble protective group,
 f. removing the fat-soluble protective group to form a free amino group,
 g. repeating the steps e and f at least once,
 h. cutting off the resin with an acid, and
 i. transferring fluoro-sialic acid to the resulting glycopeptide using a sialic acid transferase and CMP-7-fluoro-sialic acid, CMP-8-fluoro-sialic acid, or CMP-9-fluoro-sialic acid.

12. A process for preparing a glycopeptide having at least one mucin-linked oligosaccharide at a desired position of the peptide chain thereof and a residue of a sialic acid or a derivative thereof at a terminal end thereof, the process comprising:
 a. esterifying a hydroxyl group of a resin having the hydroxyl group and a carboxyl group of an amino acid having amino group nitrogen protected with a fat-soluble protective group,
 b. removing the fat-soluble protective group to form a free amino group,
 c. amidating the free amino group and a carboxyl group of an amino acid having amino group nitrogen protected with a fat-soluble protective group,
 d. removing the fat-soluble protective group to form a free amino group,
 e. repeating the steps c and d at least once,
 f. amidating the free amino group and a carboxyl group of the resin or threonine portion of a mucin-linked oligosaccharide having amino group nitrogen protected with a fat-soluble protective group,
 g. removing the fat-soluble protective group to form a free amino group,
 h. amidating the free amino group and a carboxyl group of an amino acid having amino group nitrogen protected with a fat-soluble protective group,
 i. repeating the steps g and h at least once,
 j. removing the fat-soluble protective group to form a free amino group,
 k. cutting off the resin with an acid, and
 l. transferring fluoro-sialic acid to the resulting glycopeptide using a sialic acid transferase and CMP-7-fluoro-sialic acid, CMP-8-fluoro-sialic acid, or CMP-9-fluoro-sialic acid.

* * * * *

UNITED STATES PATENT AND TRADEMARK OFFICE
CERTIFICATE OF CORRECTION

PATENT NO. : 8,063,202 B2
APPLICATION NO. : 12/385711
DATED : November 22, 2011
INVENTOR(S) : Yasuhiro Kajihara Page 1 of 8

It is certified that error appears in the above-identified patent and that said Letters Patent is hereby corrected as shown below:

In Column 7, lines 45-55, should read:

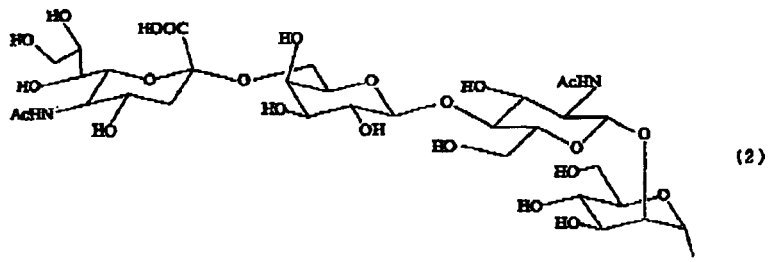

In Column 38 (line 30), reads: "25□C" and should read:

--25°C--.

Signed and Sealed this
Twenty-second Day of May, 2012

David J. Kappos
*Director of the United States Patent and Trademark Office*

CERTIFICATE OF CORRECTION (continued)

U.S. Pat. No. 8,063,202 B2

Page 2 of 8

In columns 43 and 44 (EXAMPLE 2), should read:

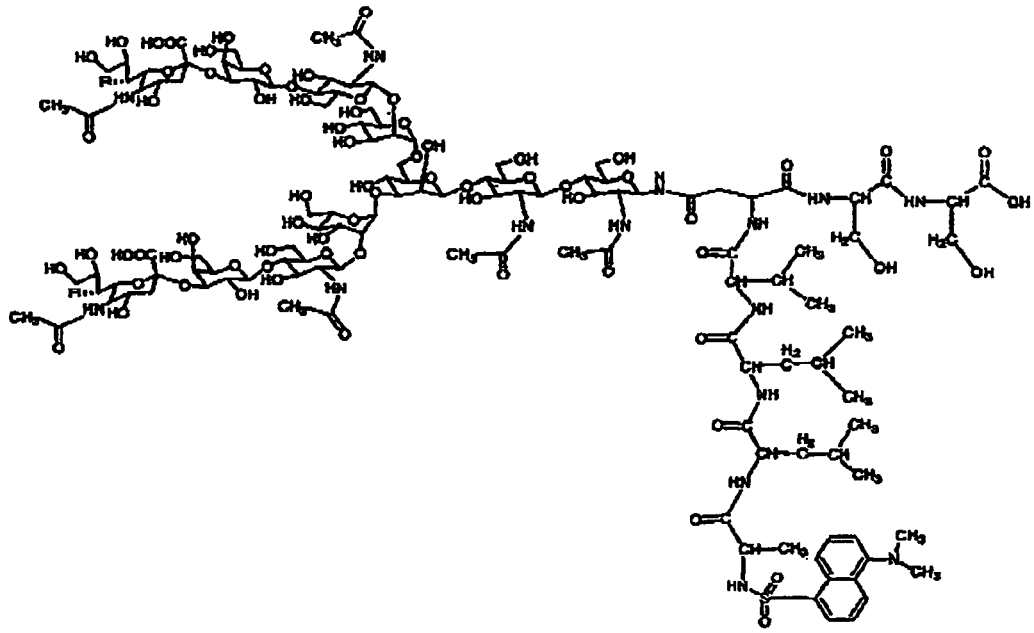

In columns 45 and 46 (EXAMPLE 2), should read:

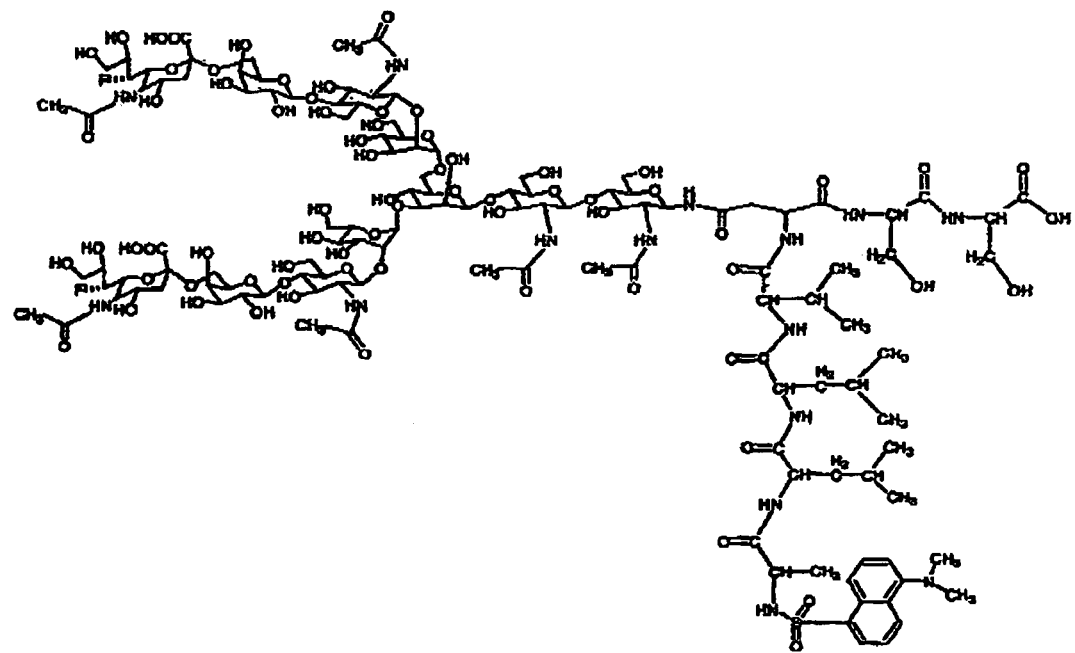

CERTIFICATE OF CORRECTION (continued)
U.S. Pat. No. 8,063,202 B2

Page 3 of 8

In columns 47 and 48 (EXAMPLE 2), should read:

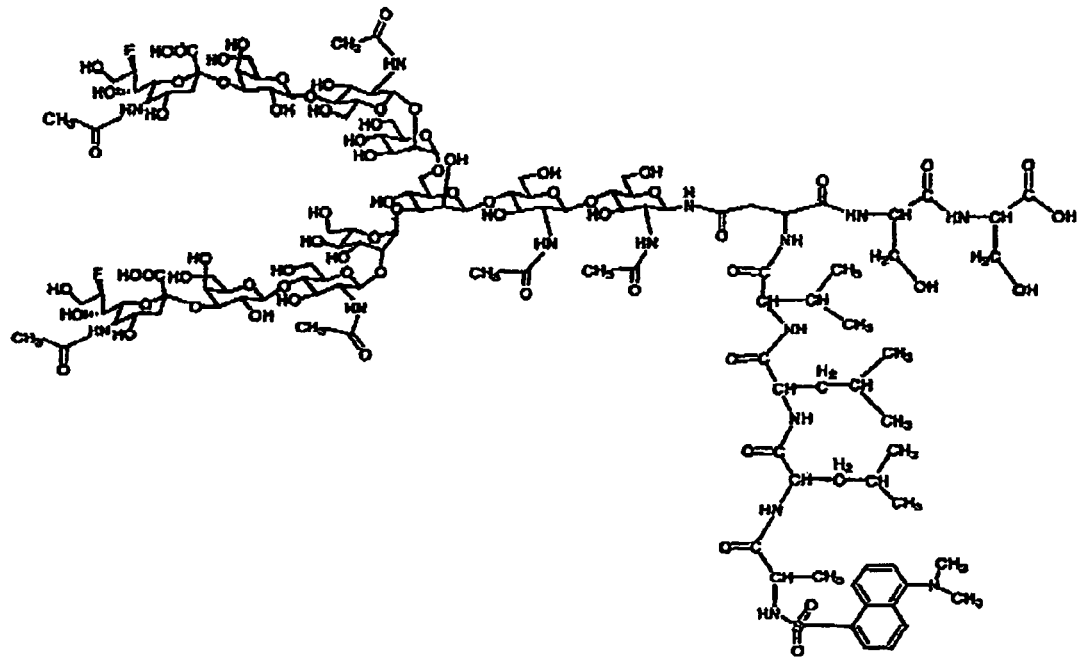

In columns 49 and 50 (EXAMPLE 2), should read:

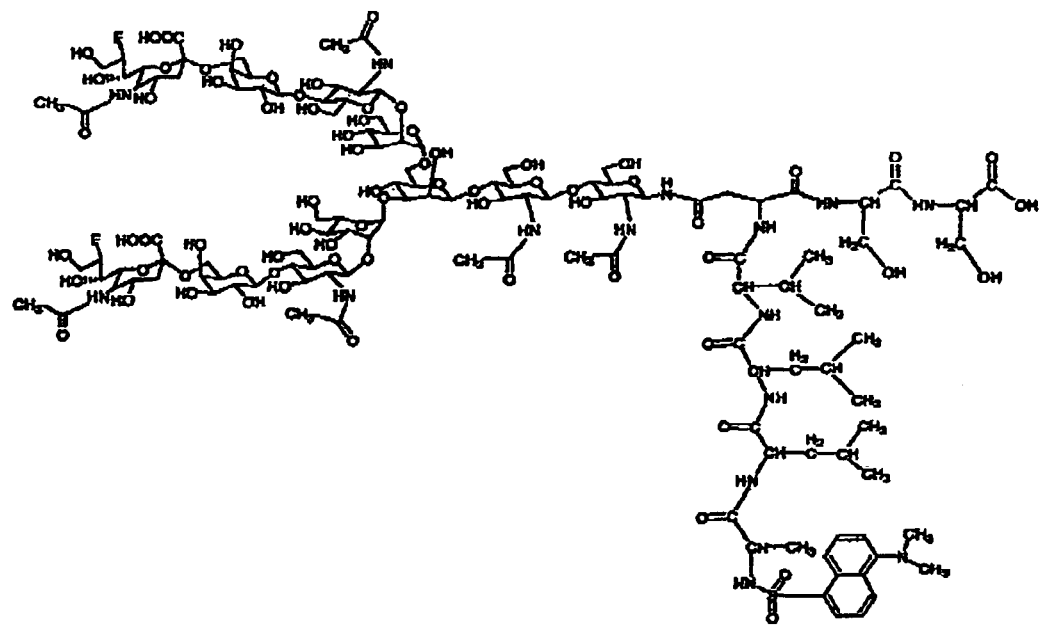

In columns 51 and 52 (EXAMPLE 2), should read:
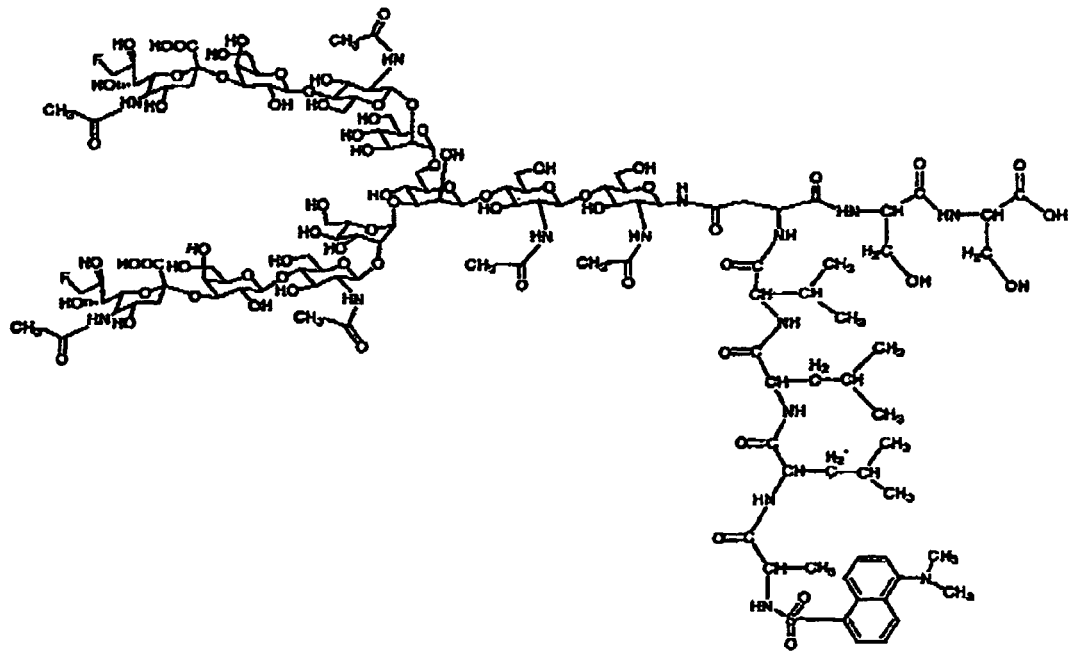
In columns 53 and 54 (EXAMPLE 2), should read:
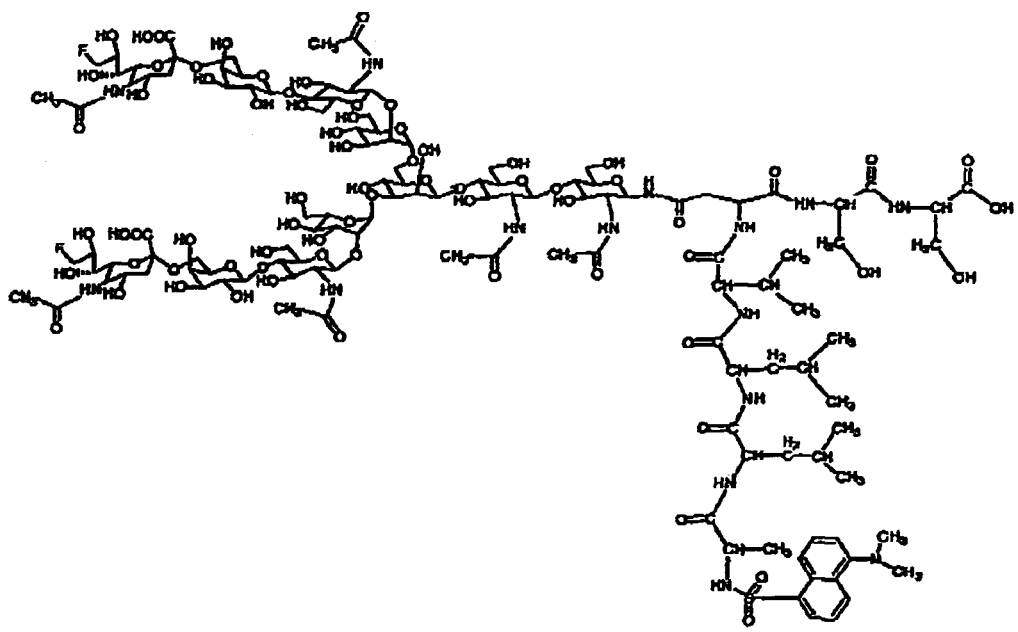

CERTIFICATE OF CORRECTION (continued)  Page 5 of 8
U.S. Pat. No. 8,063,202 B2

In columns 55 and 56 (EXAMPLE 2), should read:

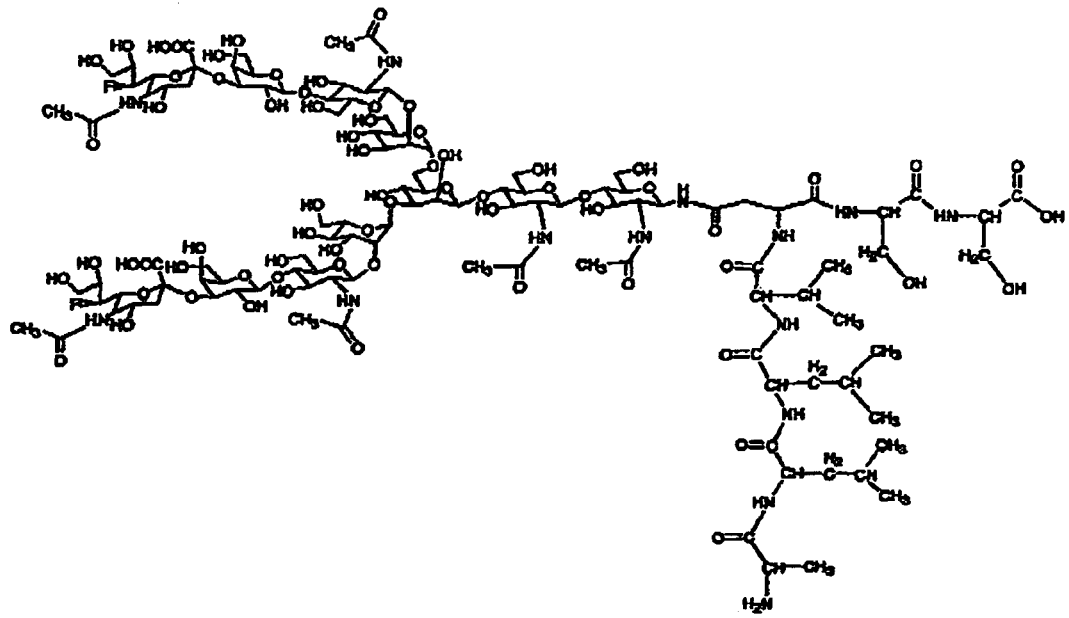

In columns 57 and 58 (EXAMPLE 2), should read:

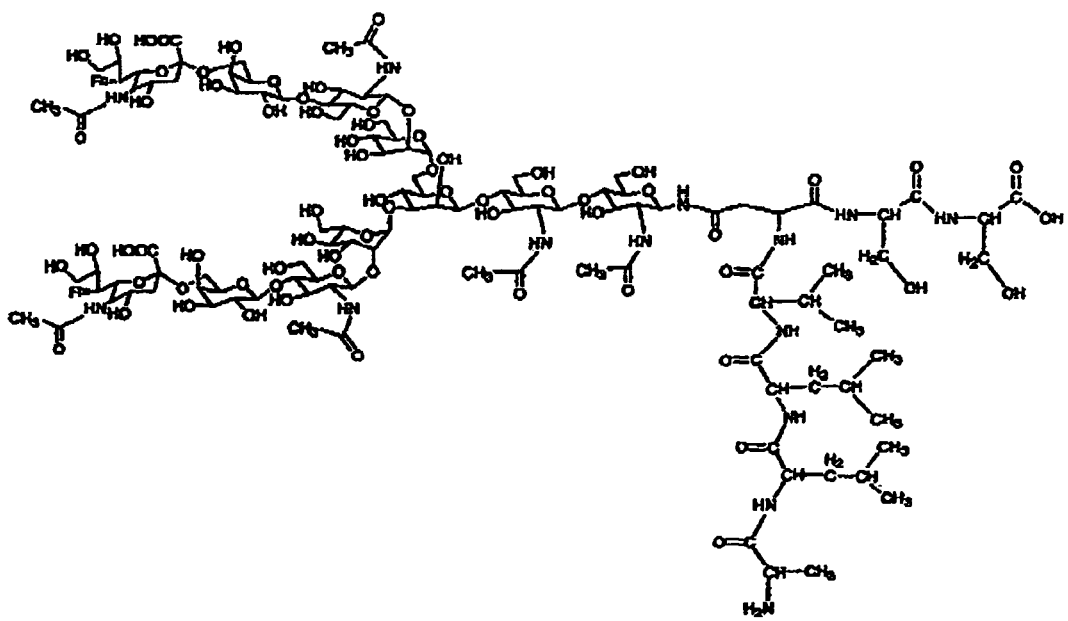

CERTIFICATE OF CORRECTION (continued) Page 6 of 8
U.S. Pat. No. 8,063,202 B2

In columns 59 and 60 (EXAMPLE 2), should read:

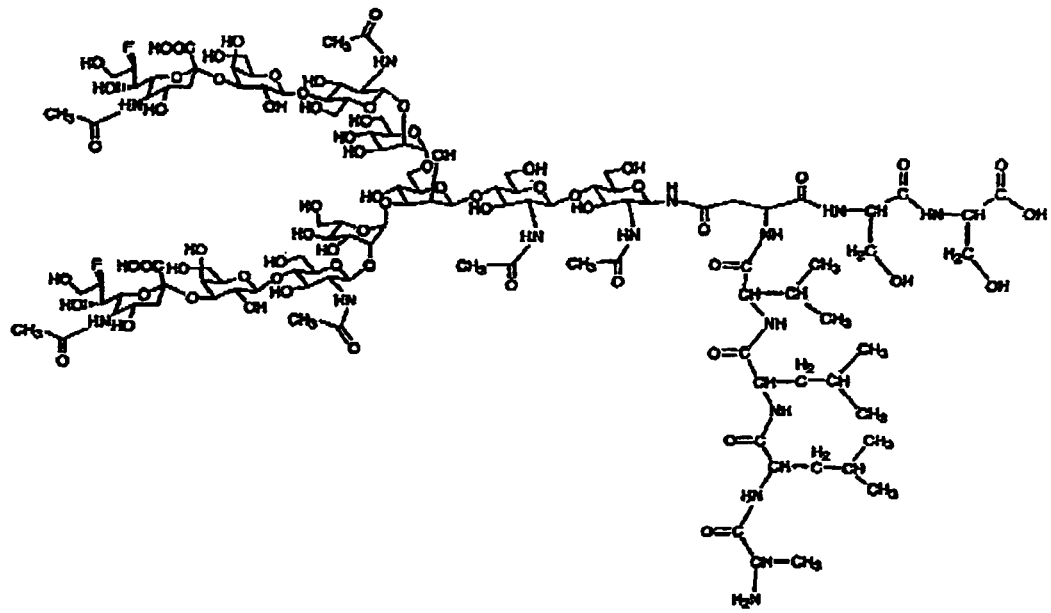

In columns 61 and 62 (EXAMPLE 2), should read:

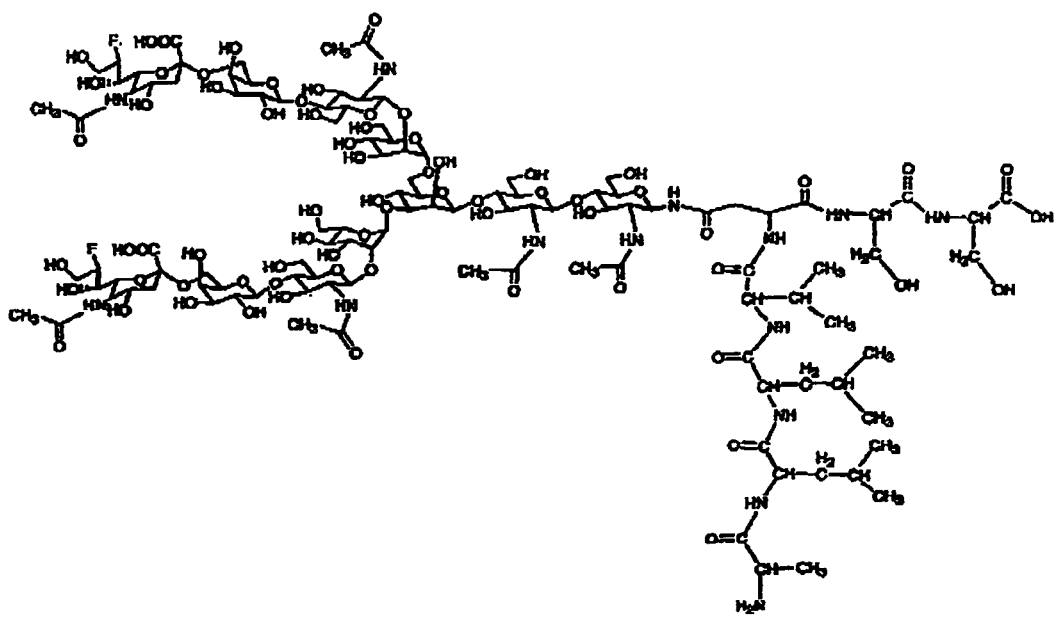

CERTIFICATE OF CORRECTION (continued) Page 7 of 8
U.S. Pat. No. 8,063,202 B2

In columns 63 and 64 (EXAMPLE 2), should read:

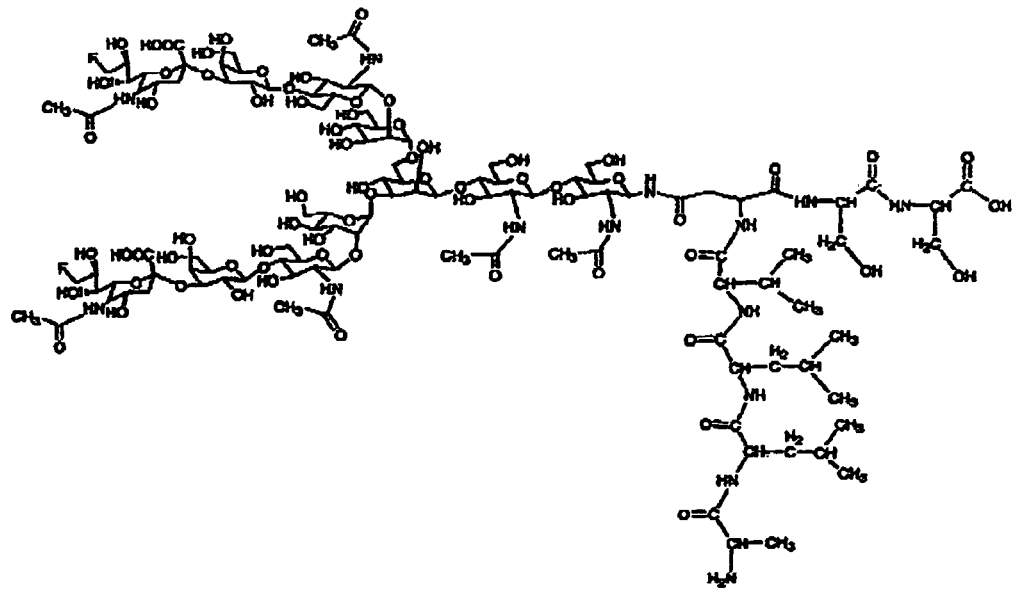

In columns 65 and 66 (EXAMPLE 2), should read:

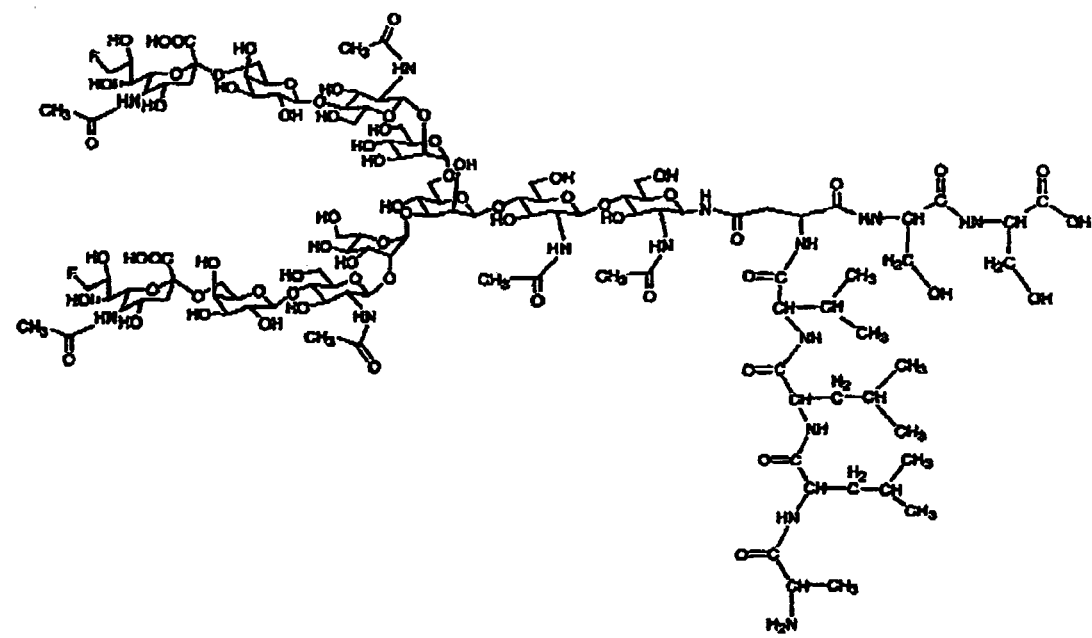

CERTIFICATE OF CORRECTION (continued)
U.S. Pat. No. 8,063,202 B2

In columns 67-70 (EXAMPLE 2), should read:

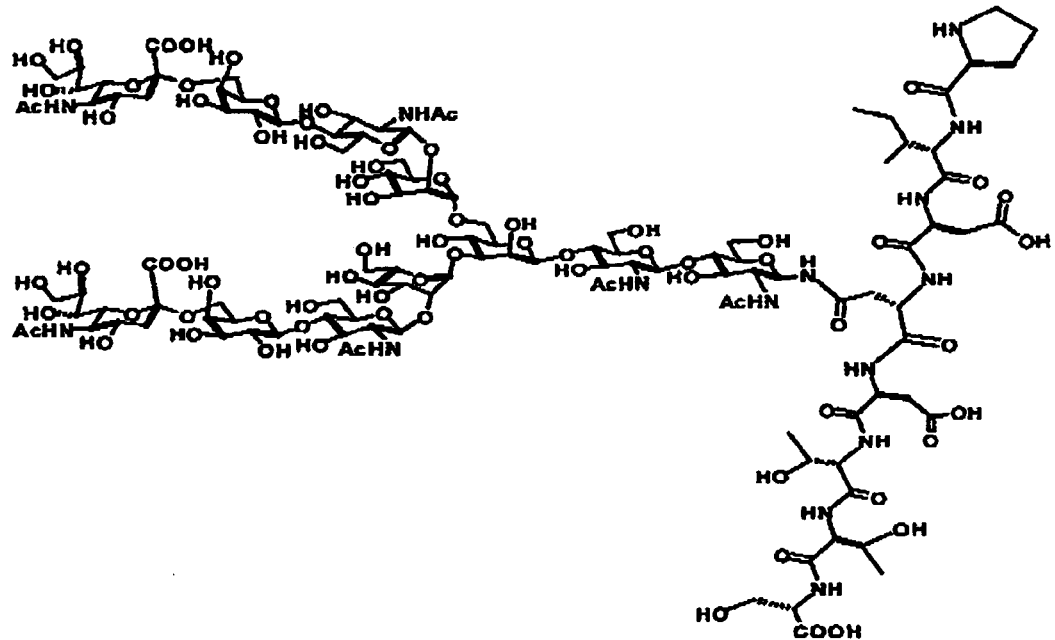

In the Claims:

In Claim 1, column 69, line 63, "a terminal and thereof" should read:

--a terminal end thereof,--